US010307471B2

(12) United States Patent
Okuda et al.

(10) Patent No.: US 10,307,471 B2
(45) Date of Patent: Jun. 4, 2019

(54) IMMUNITY INDUCER FOR SACCHARIDE ANTIGENS

(71) Applicant: NATIONAL INSTITUTE OF ADVANCED INDUSTRIAL SCIENCE AND TECHNOLOGY, Tokyo (JP)

(72) Inventors: Tetsuya Okuda, Sapporo (JP); Hiroki Shimizu, Sapporo (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 10 days.

(21) Appl. No.: 14/888,353

(22) PCT Filed: May 2, 2014

(86) PCT No.: PCT/JP2014/002401
§ 371 (c)(1),
(2) Date: Oct. 30, 2015

(87) PCT Pub. No.: WO2014/178195
PCT Pub. Date: Nov. 6, 2014

(65) Prior Publication Data
US 2016/0074522 A1 Mar. 17, 2016

(30) Foreign Application Priority Data

May 2, 2013 (JP) .................................. 2013-096860

(51) Int. Cl.
*A61K 39/00* (2006.01)
*A61K 31/702* (2006.01)
*C08B 37/00* (2006.01)
*A61K 31/7028* (2006.01)
*A61K 39/39* (2006.01)
*C07K 16/18* (2006.01)
*C07H 15/06* (2006.01)
*C07H 15/10* (2006.01)
*A61K 47/54* (2017.01)

(52) U.S. Cl.
CPC ........ *A61K 39/0011* (2013.01); *A61K 31/702* (2013.01); *A61K 31/7028* (2013.01); *A61K 39/39* (2013.01); *A61K 47/543* (2017.08); *C07H 15/06* (2013.01); *C07H 15/10* (2013.01); *C07K 16/18* (2013.01); *C08B 37/00* (2013.01); *A61K 2039/55511* (2013.01); *A61K 2039/6018* (2013.01); *A61K 2039/627* (2013.01); *C07K 2317/92* (2013.01); *C07K 2317/94* (2013.01)

(58) Field of Classification Search
None
See application file for complete search history.

(56) References Cited

U.S. PATENT DOCUMENTS

2002/0032158 A1 3/2002 Tomiyama et al.

FOREIGN PATENT DOCUMENTS

| EP | 0 165 811 A2 | 12/1985 |
|---|---|---|
| EP | 0 988 860 A1 | 3/2000 |
| JP | 61-63700 A | 4/1986 |
| JP | 3-275694 A | 12/1991 |
| JP | 3-279394 A | 12/1991 |
| JP | 3495740 B2 | 2/2004 |
| JP | 2008-013497 A | 1/2008 |
| JP | 2008-514686 A | 5/2008 |
| JP | 2011-524417 A | 9/2011 |
| WO | 03/009812 A2 | 2/2003 |
| WO | 2006/027685 A2 | 3/2006 |
| WO | 2006/037979 A2 | 4/2006 |
| WO | 2010/005598 A1 | 1/2010 |

OTHER PUBLICATIONS

Cerundolo, V., Silk, J. D., Masri, S. H., & Salio, M. (2009). Harnessing invariant NKT cells in vaccination strategies. Nature Reviews Immunology, 9(1), 28-38.*
Kinjo, Y., Pei, B., Bufali, S., Raju, R., Richardson, S. K., Imamura, M., . . . & Wong, C. H. (2008). Natural Sphingomonas glycolipids vary greatly in their ability to activate natural killer T cells. Chemistry & biology, 15(7), 654-664.*
Bremer, E. G., Schlessinger, J., & Hakomori, S. I. (1986). Ganglioside-mediated modulation of cell growth. Specific effects of GM3 on tyrosine phosphorylation of the epidermal growth factor receptor. Journal of Biological Chemistry, 261(5), 2434-2440. (Year: 1986).*
S. Bachan, et al., "Synthesis, gp120 binding and anti-HIV activity of fatty acid esters of 1,1-linked disaccharides", Bioorganic & Medical Chemistry, Pergamon, GB, vol. 19, No. 16, 2011, pp. 4803-4811. Cited in Extended (Supplementary) European Search Report dated Dec. 6, 2016.

(Continued)

*Primary Examiner* — Shaojia A Jiang
*Assistant Examiner* — Dale R Miller
(74) *Attorney, Agent, or Firm* — Westerman, Hattori, Daniels & Adrian, LLP

(57) ABSTRACT

The present invention provides an immunity inducer and an immunity inducing method using same. The immunity inducer has an immunopotentiation effect on any target oligosaccharide antigen, in particular oligosaccharide antigens included in mammal-derived glycoprotein N-linked sugar chains; is capable of providing a monoclonal antibody having high specificity to and affinity with target oligosaccharide antigens; and has as an effective component thereof a glycolipid including a target oligosaccharide antigen (R) and indicated by general formula (2), or a salt thereof. General formula (2): $R-Z-Y-CH(NH-CO-(CH_2)_{n1}-CH_3)-CH_2)_{n2}-CH_3$ (in the formula, R indicates a straight-chain or branched oligosaccharide comprising 2-30 of at least one type of monosaccharide. Z indicates a single bond, O, S or NH, a linker bound to thiomethyl, amino methylated sugar alcohol. Y indicates $-(CH_2)_m-$. n1 indicates an integer of 2-40, n2 indicates an integer of 1-27, and m indicates an integer of 1-30).

16 Claims, 6 Drawing Sheets

(56) References Cited

OTHER PUBLICATIONS

Extended (Supplementary) European Search Report dated Dec. 6, 2016, issued in counterpart European Patent Application No. 14791926.0. (10 pages).
Notification of Transmittal of Translation of the International Preliminary Report on Patentability (Forms PCT/IB/326) issued in counterpart International Application No. PCT/JP2014/002401 dated Nov. 12, 2015, with Forms PCT/IB/373, PCT/IB/338 and PCT/ISA/237. (10 pages).
Shimamura et al., "Induction of promotive rather than suppressive immune responses from a novel NKT cell repertoire Valpha19 NKT cell with alpha-mannosyl ceramide analogues consisting of the immunosuppressant ISP-I as the sphingosine unit", European Journal of Medicinal Chemistry, 2006, vol. 41, pp. 569-576, cited in ISR (8 pages).
Milkereit et al., "Complex effect of ethyl branching on the supramolecular structure of a long chain neoglycolipid", Colloids and Surfaces A: Physicochem. Eng. Aspects, 2005, vol. 268, pp. 155-161, cited in ISR (7 pages).
Blackburn et al., "Carbohydrate-specific Cell Adhesion Is Mediated by Immobilized Glycolipids", The Journal of Biological Chemistry, 1983, vol. 258, No. 2, p. 1180-1188, cited in ISR (9 pages).
Morita et al., "Structure-Activity Relationship of alpha-Galactosylceramides against B16-Bearing Mice", J. Med. Chem., 1995, vol. 38, pp. 2176-2187, cited in ISR and Specification (12 pages).
Ishihara et al., "alpha-Glycosylceramides Enhance t he Antitumor Cytotoxicity of Hepatic Lymphocytes Obtained from Cancer Patients by Activating CD3•CD56• NK Cells in Vitro", The Journal of Immunology, 2000, vol. 165, pp. 1659-1664, cited in ISR (12 pages).
Okuda et al., "Sialyl-ka Tosa o Kenshutsu suru Tameno Shinki Monoclonal Kotai no Kaihatsu", Dai 32 Kai The Japanese Society of Carbohydrate Research Nenkai, Jul. 25, 2013, vol. 32, pp. 141-143, cited in ISR (3 pages). With English abstract.
International Search Report dated Aug. 5, 2014, issued in counterpart Application No. PCT/JP2014/002401 (3 pages).
Narimatsu et al., "A strategy for discovery of cancer glycobiomarkers in serum using newly developed technologies for glycoproteomics", The FEBS Journal, 2009, vol. 277, pp. 95-105, cited in the specification (11 pages).
Nakagawa et al., "Glycomic Analysis of Alpha-Fetoprotein L3 in Hepatoma Cell Lines and Hepatocellular Carcinoma Patients", Journal of Proteome Research, 2008, vol. 7, pp. 2222-2233, cited in the specification (11 pages).
Saldova et al., "Ovarian cancer is associated with changes in glycosylation in both acute-phase proteins and IgG", Glycobiology, 2007, vol. 17, No. 12, pp. 1344-1356, cited in the specification (13 pages).
Kuno et al., "LecT-Hepa: A triplex lectin-antibody sandwich immunoassay for estimating the progression dynamics of liver fibrosis assisted by a bedside clinical chemistry analyzer and an automated pretreatment machine", Clinica Chimica Acta, 2011, vol. 412 pp. 1767-1772, cited in the specification (6 pages).
Kuno et al., "A serum "sweet-doughnut" protein facilitates fibrosis evaluation and therapy assessment in patients with viral hepatitis", Scientific Reports, Jan. 15, 2013, Rep. 3, 1065, pp. 1-9, cited in the specification (9 pages).
Ohtsubo et al., "Pathway to diabetes through attenuation of pancreatic beta cell glycosylation and glucose transport", NIH Public Access Author Manuscript, 2011, vol. 17, No. 9, pp. 1067-1075, cited in the specification (17 pages).
Murakami et al., "Convenient preparation and characterization of a monoclonal antibody for the N-linked sugar chain of a glycoprotein using a microbial endoglycosidase", Archives Biochemistry and Biophysics, 2008, 477, pp. 299-304, Cited in Specification (6 pages).
Ozawa et al., "Generation and Characterization of Mouse Monoclonal Antibodies Specific for N-Linked Neutral Oligosaccharides of Glycoproteins", Archives of Biochemistry and Biophysics, Jun. 1, 1997, vol. 342, No. 1, pp. 48-57, cited in the specification (10 pages).
Stein et al., "The Immune Response to an Isomaltohexosyl-Protein Conjugate, a Thymus-Dependent Analogue of alpha($1 \to 6$) Dextran", The Journal of Immunology, Mar. 3, 1982, vol. 128, No. 3, pp. 1350-1354, Cited in Specification (5 pages).
Matsuda et al., "Variable Region cDNA Sequences and Antigen Binding Specificity of Mouse Monoclonal Antibodies to Isomaltosyl Oligosaccharides Coupled to Proteins", The Journal of Immunology, Feb. 1, 1989, vol. 142, No. 3, pp. 863-870, Cited in the specification (8 pages).
Nashed et al., "Binding Characteristics of IgA 16.4.123E, a Monoclonal Antibody with Specificity for the Nonreducing Terminal Epitope of alpha-($1 \to 6$)-Dextrans", The Journal of Biological Chemistry, Nov. 25, 1990, vol. 265, No. 33, pp. 20699-20707, Cited in the specification (9 pages).
Rothenberg et al., "Biotinylated diaminopyridine: An approach to tagging oligosaccharides and exploring their biology", Proc. Natl. Acad. Sci. USA, Dec. 1993, vol. 90, pp. 11939-11943, Cited in Specification (5 pages).
Costa-Nogueria et al., "Synthesis and expression of CDw75 antigen in human colorectal cancer", BMC Cancer 2009, 9, 431, Cited in the specification (10 pages).
Suzuki, "Sialobiology of Influenza Molecular Mechanism of Host Range Variation of Influenza Viruses", Biol. Pharm. Bull. 28(3), Mar. 2005, pp. 399-408, Cited in the specification (10 pages).
Heimburg-Molinaro et al., "Cancer Vaccines and Carbohydrate Epitopes", Vaccine. Nov. 8, 2011, 29(48), 8802-8826, Cited in the specification (57 pages).
Takahashi et al., "Induction of Pluripotent Stem Cells from Mouse Embryonic and Adult Fibroblast Cultures by Defined Factors", Cell. 126, Aug. 25, 2006, pp. 663-676, Cited in the specification (14 pages).
Muramatsu et al., "Carbohydrate antigens expressed on stem cells and early embryonic cells", Glycoconjugate Journal, 2004, 21, pp. 41-45, Cited in the specification (5 pages).
Yanagisawa, "Stem Cell Glycolipids", Neurochem. Res., 36, 2011, pp. 1623-1635, Cited in the specification (13 pages).
Goff, R. D. et al, "Effects of Lipid Chain Lengths in alpha-Galactosylceramides on Cytokine Release by Natual Killer T Cells", Journal of the American Chemical Society, Oct. 27, 2004, vol. 126, No. 42, pp. 13602-13603; cited in European Office Action.
Office Action dated Jul. 27, 2017, issued in counterpart European Application No. 14791926.0. (6 pages).

\* cited by examiner

A

B

IMMUNITY INDUCER FOR SACCHARIDE ANTIGENS

TECHNICAL FIELD

The present invention relates to a method of enhancing immunogenicity of a carbohydrate antigen and a carrier compound for the method. The present invention also relate to a novel glycolipid compound obtained by bonding a carbohydrate antigen and a carrier compound, a method of immunity enhancement using the glycolipid compound, a method for producing an antibody that recognizes a carbohydrate antigen, particularly, a method for producing a monoclonal antibody.

BACKGROUND ARTS

Reflecting cell strains, development and differentiation stages, pathologic conditions, a sugar chain having each characteristic structure is expressed in mammalian cells. Sugar chains exist in a cell surface layer and a serum in the form of a complex carbohydrate such as a glycoprotein and a glycolipid, and an effective utilization as a biomarker has been examined from the properties in the same manner as a protein and nucleic acid. In recent years, it begins to find out that sugar chains has an important function in vivo, and researches relating to the function have been advanced.

However, a functional analysis has scarcely progressed since techniques relating to structural identification and detection of a sugar chain are not sufficiently established as compared to protein and nucleic acid. If an antibody capable of distinguishing and detecting a partial structure of a sugar chain, which characterizes a sugar chain structure of a complex carbohydrate, could be easily developed, a sugar chain analysis by ELISA, a western blot method, etc., which are generally employed in a protein analysis, is possible, and research developments relating to functional clarification and industrial applications of sugar chains are considered to be accelerated.

Among sugar chain structures of complex carbohydrates, particularly, an N-linked sugar chain structure contained in a glycoprotein becomes various cancer diagnosis markers or diagnosis markers for serious diseases in many cases; therefore, expectation of development of an antibody that can recognize an N-linked sugar chain structure is significant.

For example, a change in an N-linked sugar chain structure of a glycoprotein in liver cancer has been known for a use as a diagnosis marker so far (Non Patent Literature 1). A typical example thereof is an N-linked sugar chain of α-fetoprotein (AFP). An increase of a serum value of AFP has been utilized as a diagnostic index of liver cancer for a long time; however, there was a defect such that only liver cancer cannot be precisely diagnosed since the serum value of AFP increases also in hepatitis and hepatic cirrhosis. It was recently found that an N-linked sugar chain structure of an AFP protein is chained specifically in liver cancer (Non Patent Literature 2), and AFP-L3 containing such a sugar chain structure is focused as a highly precise diagnosis marker for liver cancer. Regarding ovarian cancer, immunoglobulins and acute-phase proteins, which contain core fucose type and sLe$^x$ type N-linked sugar chains, have been found as novel marker candidates (Non Patent Literature 3).

In addition, an N-linked sugar chain started finding to be useful as a marker of hepatic fibrosis (previous stage of hepatic cirrhosis) which is a previous symptom of hepatic cirrhosis. An N-linked sugar chain of an α1-acid glycoprotein (AGP) existing in the serum has a characteristic structure correlating to the onset of hepatic fibrosis, and LecT-Hepa has been developed as a marker that diagnoses the onset of hepatic fibrosis (Non Patent Literature 4). What is more, by FastLec-Hepa that has been improved so as to be able to detect at high sensitivity and with simplicity, a change specific to hepatic fibrosis, which is found in an N-linked sugar chain of an M2BP glycoprotein in the blood, is detected (Non Patent Literature 5).

Other than the above, abnormality of an N-linked sugar chain structure of a glucose transporter protein, which is expressed in the pancreas by diabetes, and the like, has been proposed to be a cause of developing the pathologic condition (Non Patent Literature 6).

From the background as described above, an expectation of a technique of easily preparing an antibody that can recognize a sugar chain structure of a complex carbohydrate, particularly, an N-linked sugar chain structure in a glycoprotein has more increased; however, when an oligosaccharide chain constituting a specific partial structure of a sugar chain part in a complex carbohydrate is used as an immunogen, it is very hard to obtain a practical and useful antibody. The greatest reason is because, in the immune system of a mammalian body utilized as a host producing an antibody, development of the immune system which recognizes an oligosaccharide chain as an antigen is insufficient. In particular, production of an antibody which recognizes "an N-linked sugar chain-derived oligosaccharide chain in a glycoprotein" has been known to be difficult (Non Patent Literatures 7 and 8), and an effective antibody is not hardly developed even to the present date.

On the other hand, when a peptide is an immunogen, there is a technique of utilizing an immunity induction system by antigen presentation by use of an MHC molecule and enhancing the immunogenicity. In the method, any peptide is bound to a carrier protein such as KLH and BSA to form an immunity inducer, thereby enhancing an interaction with the MHC molecule through a carrier protein, and an objective antigen can be a thymus-dependent antigen. When the objective antigen can be a thymus-dependent antigen, a B cell that is an antibody producing cell is capable of production of a useful antibody with high specificity and broad application by undergoing processes such as class switching, affinity maturation, and memory of antibody production due to interaction with a helper T cell.

Also when an oligosaccharide chain is an immunogen, there is a report that a conjugate (artificial glycoprotein) with a carrier protein such as KLH and BSA, which are used to the peptide, was prepared and immunized to produce an IgG antibody recognizing a target carbohydrate antigen (Non Patent Literatures 9 and 10). However, the oligosaccharide chain in the report is an examination of using a polymer of α1,6 glucose (derived product of isomaltose) prepared by dextran derived from microorganisms, which is not an examination of using a mammalian complex carbohydrate-derived oligosaccharide chain, at the same time, the affinity of the obtained monoclonal antibody is low as an association constant of approximately $10^2$ M$^{-1}$ to $10^5$ M$^{-1}$ (Non Patent Literature 11), and the examination was not sufficient as a production method of development of a monoclonal antibody. Also from this result, even when the same conjugation method in peptide immunization is directly applied in the case of a mammalian cell-derived oligosaccharide chain, a possibility of functioning as a thymus-dependent antigen is low, an antibody finally showing sufficient affinity and specificity is thinly estimated and, thus, this technique could not be a practical option for a person skilled in the art.

Therefore, a research of a carrier compound as an alternative to the technique has been activated.

A method of inducing immunity by using, as an immunogen, a material obtained by reductively bonding an oligosaccharide chain to an amino group in biotinylated aminopyridine and subsequently polyvalently bonding biotin to avidin that is a ligand (Non Patent Literature 12) has been known so far, and although immunity is induced using the above described isomaltose derived product (heptasaccharide) as an oligosaccharide chain, immunity enhancement ability is low and development of an effective monoclonal antibody to a target oligosaccharide chain is not attained.

In addition, regarding "Galβ1,4GlcNAcβ1,2Man", "a β-GlcNAc residue in a nonreducing end" and "Siaα2,6Galβ1,4GlcNAc (CDw75)", which are oligosaccharide antigens in N-linked sugar chains of typical glycoproteins, a method of inducing immunity by using phosphatidyl ethanolamine as a carrier compound and using a compound obtained by reductively bonding an oligosaccharide chain to the amino group as an immunogen (Non Patent Literatures 7 and 8) has been reported. However, affinity and specificity are insufficient in monoclonal antibodies obtained by these immunity inducing methods, a practical antibody therefore cannot be considered to be provided and the immunity inducing methods are not generally used techniques of selectively inducing an antibody to any sugar chain. What is more, in these immunity inducing methods, since a reductive amination method of cleaving the reducing end sugar of an oligosaccharide chain is utilized as a production method in conjugating a carrier compound and the oligosaccharide chain, an immunity inducer cannot be synthesized with keeping the structure of the oligosaccharide chain. Therefore, the methods have a defect such that a spacer is essential in order to prevent cleavage and a complicated synthesis process of previously bonding sugar or hydroxybenzaldehyde for a spacer to an oligosaccharide chain is required.

In addition, a method of using magnetic metallic nano particles that are obtained by bonding to a sugar chain ligand with an adjuvant through a linker (Patent Literature 1) has been proposed, but preparation of nano particles is not easy, and a process of bonding a sugar chain ligand and an adjuvant to the nano particles at a constant ratio is also not easy. It is proposed that, to a Globo-H carbohydrate specific to breast cancer, a carrier protein that is a diphtheria toxin cross-reacting substance is bound to the reducing side of the Globo-H carbohydrate through aminoalkyl and p-nitrophenyl ester to form a cancer vaccine (Patent Literature 2), which however is not a generally applicable technique that can apply to a general carbohydrate antigen.

According to the above description, desired was development of a carrier compound which becomes an excellent immunity inducer applicable to widely general oligosaccharide antigens, in particular, a glycoprotein N-linked sugar chain-derived oligosaccharide chain that is hardly produced and is capable of induction of an anti-carbohydrate antigen monoclonal antibody with high specificity and affinity. In addition, a production method capable of easily bonding a carrier compound and an oligosaccharide chain with keeping the structure of the target oligosaccharide antigen was also desired.

CITATION LIST

Patent Literatures

Patent Literature 1: JP 2008-514686 W
Patent Literature 2: JP 2011-524417 W
Patent Literature 3: JP 3495740 B2
Patent Literature 4: JP 61-63700 A
Patent Literature 5: JP 2008-13497 A Non Patent Literatures Non Patent Literature 1: Narimatsu H., et al. (2010) FEBS J. 277, 95-105.
Non Patent Literature 2: Nakagawa T., et al. (2008) J. Proteome Res. 7, 2222-2233.
Non Patent Literature 3: Saldova R., et al. (2007) Glycobiology. 17, 1344-1356.
Non Patent Literature 4: Kuno A., et al. (2011) Clin. Chim. Acta. 412,1767-1772.
Non Patent Literature 5: Kuno A., et al. (2013) Sci. Rep. 3, 1065.
Non Patent Literature 6: Ohtsubo K., et al. (2011) Nat. Med. 17, 1067-1075.
Non Patent Literature 7: Ozawa H., et al. (1997) Arch. Biochem. Biophys. 342,48-57.
Non Patent Literature 8: Murakami D., et al. (2008) Arch. Biochem. Biophys. 477, 299-304.
Non Patent Literature 9: Stein K E., et al. (1982) J. Immunol. 128, 1350-1354.
Non Patent Literature 10: Matsuda T. and Kabat E A. (1989) J. Immunol. 142,863-870.
Non Patent Literature 11: Nashed E M., et al. (1990) J. Biol. Chem. 265, 20699-20707.
Non Patent Literature 12: Rothenberg B E., et al. (1993) Proc. Natl. Acad. Sci. USA. 90, 11939-11943.
Non Patent Literature 13: Morita M., et al. (1995) J. Med. Chem. 38, 2176-2187.
Non Patent Literature 14: Costa-Nogueira C., et al. (2009) BMC Cancer. 9, 431.
Non Patent Literature 15: Suzuki Y. (2005) Biol. Pharm. Bull. 28, 399-408.
Non Patent Literature 16: Heimburg-Molinaro J., et al. (2011) Vaccine. 29, 8802-8826.
Non Patent Literature 17: Takahashi K. and Yamanaka S. (2006) Cell. 126, 663-676.
Non Patent Literature 18: Muramatsu T. and Muramatsu H. (2004) Glycoconj. J. 21,41-45.
Non Patent Literature 19: Yanagisawa M. (2011) Neurochem. Res. 36, 1623-1635.

SUMMARY OF INVENTION

Technical Problem

The present invention provides a carrier compound having an immunopotentiation effect on any carbohydrate antigen, in particular, an oligosaccharide antigen contained in an N-linked sugar chain in a glycoprotein, and capable of providing an anti-carbohydrate antigen monoclonal antibody with high specificity and affinity to a target carbohydrate antigen. The invention also provides a method for producing an immunity inducer by simply and easily conjugating a carrier compound and an oligosaccharide chain with keeping the structure of the target oligosaccharide antigen.

Solution to Problem

The present invention focused on lipid structures of a sponge-derived α-galactosylceramide that are known for an immunostimulatory action (Non Patent Literature 13) and various glycosphingolipids which are analogs of the ceramide while searching a carrier compound capable of enhancing immunogenicity of a carbohydrate antigen by bonding to various target oligosaccharide antigens, in particular, an oligosaccharide antigen contained in a glycoprotein N-linked sugar chain. These various glycosphingolipids have been known for antigen presentation through a CD1 molecule on a dendritic cell to activate NKT cells, and widely known as an adjuvant in addition to an immunotherapeutic agent utilizing the immunostimulatory action (Patent Literatures 2 and 3); however, there is no example of using a lipid moiety of the α-galactosylceramide or an analog thereof as a carrier compound for the purpose of enhancing immunogenicity of a carbohydrate antigen.

The present inventors conceived of bonding a lipid structure of α-galactosylceramide to be a bonding moiety with a CD1 molecule to a carbohydrate antigen and examined various lipid structures; as a result, they found that a carrier compound (artificial lipid) having a lipid structure of the general formula (1) having a saturated alkyl group without existing a group containing an oxygen atom such as —OH and an unsaturated bonding group in an alkyl group in the amino group side, which is not a naturally exiting lipid structure, has the largest immunogenicity enhancement action. What is more, the immunogenicity enhancement action was also able to be verified to have very high practicability capable of applying not only to a specific carbohydrate antigen, but also to any carbohydrate antigen including various oligosaccharide antigens included in N-linked sugar chain-derived oligosaccharide antigens.

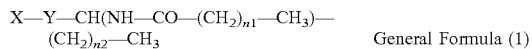
General Formula (1)

(In the formula, X represents —H, —OH, —SH, —NH$_2$, halogen or a hydrazide group, Y represents a spacer sequence such as —(CH$_2$)$_m$ (m represents an integer from 1 to 30, preferably an integer from 1 to 3), n1 represents an integer from 2 to 40, n2 represents an integer from 1 to 27, preferably an integer from 2 to 13.)

Any oligosaccharide chain to be the object of the present invention can be synthesized in both organic synthesis and an enzyme synthesis method, and when a hydroxyl group other than a reducing end of an oligosaccharide chain is protected and reacted with the carrier compound of the formula (1), the oligosaccharide chain and the carrier compound can be conjugated with keeping the oligosaccharide chain structure.

The obtained conjugate of the oligosaccharide antigen and the carrier compound (artificial glycolipid) can be expressed by the following general formula (2).

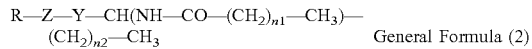
General Formula (2)

(In the formula, R represents an oligosaccharide to be a carbohydrate antigen, Z represents a single bond, or O, S, or NH, Y, n1 and n2 are defined in the same manner as the general formula (1).)

A mouse is immunized with a conjugate (artificial glycolipid) of various oligosaccharide antigens and a carrier compound of the general formula (1) as an immunity inducer in a general method and the serum antibody titer to a target oligosaccharide chain was evaluated to thus confirmed that any oligosaccharide antigen can induce production of an antibody recognizing the target oligosaccharide chain. Furthermore, when a structure of a preferable carrier compound was examined using a serum antibody titer to a target oligosaccharide chain (CDw75) as the index and a monoclonal antibody was produced using a conjugate (artificial glycolipid) (a3-1/CDw75-C12L) of the target oligosaccharide chain and a carrier compound having a sufficiently long alkyl chain (HOCH$_2$CH(NH—CO—(CH$_2$)$_{22}$—CH$_3$)—(CH$_2$)$_9$—CH$_3$:C12L), it was found that the carrier compound (C12L) also has a significant immunogenicity enhancement action and an activity as a thymus-dependent antigen (production inducing ability of IgG antibody).

According to the above description, it was verified that a carrier compound of the general formula (1) enhances immunogenicity of a target oligosaccharide antigen as an immunity inducer obtained by conjugating with any oligosaccharide antigen including an N-linked sugar chain-derived oligosaccharide antigen of a glycoprotein, and can impart an activity as a thymus-dependent antigen. By appropriately selecting a spacer sequence, a further increase of the activity and simplicity of bonding between an oligosaccharide chain and a carrier compound are also expected.

In addition, it was found in a carrier compound of the general formula (1) that an immunity inducing ability tends to more increase as an alkyl chain length in a fatty acid moiety is elongated and also discovered at the same time that when the chain length is, on the contrary, too long, a problem such as solubility is caused to decrease a synthesis efficiency by an enzyme method, thereby identifying the range of the carrier compound with the optimum size.

According to obtaining the above described findings, the present invention is accomplished.

That is, the present invention includes the following.

[1] The present invention relates to an invention according to an immunity inducing method described below.

[1-1] An immunity inducing method antigen-specific to a target oligosaccharide antigen R in a mammal, including a process of immunizing a mammal using an immunity inducer including an artificial glycolipid which includes the target oligosaccharide antigen R and is expressed by the general formula (2) or a salt thereof as an effective component:

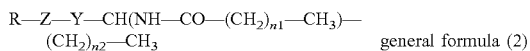
general formula (2)

(wherein R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —(CH$_2$)$_m$—, n1 represents an integer from 2 to 40, n2 represents an integer from 1 to 27, and m represents an integer from 1 to 30).

[1-2] Here, the target oligosaccharide antigen R may be any target oligosaccharide antigen, preferably a mammal-derived oligosaccharide antigen, and more preferably an oligosaccharide antigen contained in a N-linked sugar chain of a glycoprotein, and the oligosaccharide antigen contained in a N-linked sugar chain is selected from sialylated carbohydrate antigens, asialo carbohydrate antigens (non-sialylated carbohydrates) or fucosylated carbohydrate antigens.

Preferable examples of the sialylated carbohydrate antigens include "Siaα2,6Galβ1,4GlcNAc: CDw75", "Siaα2,3Galβ1,4GlcNAc: 3'-Sialyl-LacNAc", "Siaα2,3Galβ1,4(Fucα1,3) GlcNAc: Sialyl-Lewis$^x$", "Siaα2,3Galβ1,3(Fucα1,4)GlcNAc: Sialyl-Lewis$^a$", "Siaα2,3Galβ1,3(Fucα1,4) (Siaα2,6)GlcNAc: Disialyl-Lewis$^a$", "Siaα2,3Galβ1,4 (Fucα1,3)GlcNAc(6SO$_4$): 6-sulfo-Sialyl-Lewis$^x$", "Siaα2,3Gal (6SO$_4$)β1,4 (Fucα1,3)GlcNAc: 6'-sulfo-Sialyl-Lewis$^x$", "Siaα2,3Galβ1,4GlcNAcβ1,3Galβ1,4 (Fucα1,3)GlcNAc: VIM-2 antigen", "Siaα2,6GalNAcβ1,4GlcNAc", "Siaα2,3Galβ1,4(Fucα1,3)GlcNAcβ1,3Galβ1,4 (Fucα1,3)GlcNAc: Sialyl-Lewis$^x$-i", "Siaα2,3Galβ1,4GlcNAcβ1,3(Siaα2,3Galβ1,4GlcNAcβ1,6)Gal: Sialyl-I"; preferable examples of the asialo carbohydrate antigens (non-sialylated carbohydrates) include "Galβ1,4GlcNAc: LacNAc", "GlcNAcβ1,4Man", "GlcNAcβ1,6Man", "Galβ1,4GlcNAcβ1,6Man", "GalNAcβ1,4GlcNAc", "GalNAcβ1,4GlcNAcβ1,2Man", "GalNAc(4SO$_4$)β1,4GlcNAc", "Galβ1,4(Fucα1,3)GlcNAc: Lewis$^{x}$", "Galβ1,3(Fucα1,4)GlcNAc: Lewis$^{a}$", "Fucα1,2Galβ1,3(Fucα1,4)GlcNAc: Lewis$^{b}$", "Fucα1,2Galβ1,4(Fucα1,3)GlcNAc: Lewis$^{y}$", "Fucα1,6GlcNAc", "GlcNAcβ1,4 (Fucα1,6)GlcNAc", "Manβ1,4GlcNAcβ1,4(Fucα1,6)GlcNAc", "Manα1,6(Manα1,3)Manβ1,4GlcNAcβ1,4 (Fucα1,6)GlcNAc", and "Galβ1,4GlcNAcβ1,3(Galβ1,4GlcNAcβ1,6)Gal: I-antigen"; and preferable examples of the fucosylated carbohydrate antigens include "Galβ1,4 (Fucα1,3)GlcNAc: Lewis$^{x}$", "Galβ1,3(Fucα1,4)GlcNAc: Lewis$^{a}$", "Fucα1,2Galβ1,3(Fucα1,4)GlcNAc: Lewis$^{b}$", "Fucα1,2Galβ1,4(Fucα1,3)GlcNAc: Lewis$^{y}$", "Fucα1,6GlcNAc", "GlcNAcβ1,4(Fucα1,6)GlcNAc", "Manβ1,4GlcNAcβ1,4(Fucα1,6)GlcNAc", "Manα1,6(Manα1,3)Manβ1,4GlcNAcβ1,4(Fucα1,6)GlcNAc", "Siaα2,3Galβ1,4(Fucα1,3)GlcNAc: Sialyl-Lewis$^{x}$", "Siaα2,3Galβ1,3(Fucα1,4)GlcNAc: Sialyl-Lewis$^{a}$", "Siaα2,3Galβ1,3(Fucα1,4)(Siaα2,6)GlcNAc: Disialyl-Lewis$^{a}$", "Siaα2,3Galβ1,4(Fucα1,3)GlcNAc(6SO$_4$): 6-sulfo-Sialyl-Lewis$_x$", "Siaα2,3Gal(6SO$_4$)β1,4(Fucα1,3)GlcNAc: 6'-sulfo-Sialyl-Lewis$^{x}$", "Siaα2,3Galβ1,4GlcNAcβ1,3Galβ1,4(Fucα1,3)GlcNAc: VIM-2 antigen", and "Siaα2,3Galβ1,4(Fucα1,3)GlcNAcβ1,3Galβ1,4 (Fucα1,3) GlcNAc: Sialyl-Lewis$^{x}$-i".

That is, a preferable case of R in the general formula (2) can be expressed as an oligosaccharide antigen contained in an N-linked sugar chain of a mammal-derived glycoprotein.

Furthermore, a preferable case of R in the general formula (2) can also be expressed as an oligosaccharide antigens selected from sialylated carbohydrate antigens including "Siaα2,6Galβ1,4GlcNAc: CDw75", "Siaα2,3Galβ1,4GlcNAc: 3'-Sialyl-LacNAc", "Siaα2,3Galβ1,3(Fucα1,4)GlcNAc: Sialyl-Lewis$^{x}$", "Siaα2,3Galβ1,3(Fucα1,4)(Siaα2,6)GlcNAc: Disialyl-Lewis$^{a}$", "Siaα2,3Galβ1,4(Fucα1,3)GlcNAc(6SO$_4$): 6-sulfo-Sialyl-Lewis$^{x}$", "Siaα2,3Gal(6SO$_4$)β1,4(Fucα1,3)GlcNAc: 6'-sulfo-Sialyl-Lewis$^{x}$", "Siaα2,3Galβ1,4GlcNAcβ1,3Galβ1,4(Fucα1,3)GlcNAc: VIM-2 antigen", "Siaα2,6GalNAcβ1,4GlcNAc", "Siaα2,3Galβ1,4(Fucα1,3)GlcNAcβ1,3Galβ1,4(Fucα1,3)GlcNAc: Sialyl-Lewis$^{x}$-i", and "Siaα2,3Galβ1,4GlcNAcβ1,3(Siaα2,3Galβ1,4GlcNAcβ1,6)Gal: Sialyl-I"; the asialo carbohydrate (non-sialylated carbohydrate) antigens including "Galβ1,4GlcNAc: LacNAc", "GlcNAcβ1,4Man", "GlcNAcβ1,6Man", "Galβ1,4GlcNAcβ1,6Man", "GalNAcβ1,4GlcNAc", "GalNAcβ1,4GlcNAcβ1,2Man", "GalNAc(4SO$_4$)β1,4GlcNAc", "Galβ1,4 (Fucα1,3)GlcNAc: Lewis$^{x}$", "Galβ1,3(Fucα1,4)GlcNAc: Lewis$^{a}$", "Fucα1,2Galβ1,3(Fucα1,4)GlcNAc: Lewis$^{b}$", "Fucα1,2Galβ1,4 (Fucα1,3)GlcNAc: Lewis$^{y}$", "Fucα1,6GlcNAc", "GlcNAcβ1,4 (Fucα1,6)GlcNAc", "Manβ1,4GlcNAcβ1,4(Fucα1,6) GlcNAc", and "Galβ1,4GlcNAcβ1,3(Galβ1,4GlcNAcβ1,6)Gal: I-antigen"; and fucosylated carbohydrate antigens including "Galβ1,4 (Fucα1,3)GlcNAc: Lewis$^{x}$", "Galβ1,3(Fucα1,4)GlcNAc: Lewis$^{a}$", "Fucα1,2Galβ1,3(Fucα1,4)GlcNAc: Lewis$^{b}$", "Fucα1,2Galβ1,4(Fucα1,3)GlcNAc: Lewis$^{y}$", "Fucα1,6GlcNAc", "GlcNAcβ1,4(Fucα1,6)GlcNAc", "Manβ1,4GlcNAcβ1,4 (Fucα1,6)GlcNAc", "Manα1,6(Manα1,3)Manβ1,4GlcNAcβ1,4 (Fucα1,6)GlcNAc", "Siaα2,3Galβ1,4(Fucα1,3)GlcNAc: Sialyl-Lewis$^{x}$", "Siaα2,3Galβ1,4 (Fucα1,3)GlcNAc: Sialyl-Lewis$^{a}$", "Siaα2,3Galβ1,3 (Fucα1,4) (Siaα2,6)GlcNAc: Disialyl-Lewis$^{a}$", "Siaα2,3Galβ1,4(Fucα1,3)GlcNAc(6SO$_4$): 6-sulfo-Sialyl-Lewis$^{x}$", "Siaα2,3Gal(6SO$_4$)β1,4(Fucα1,3)GlcNAc: 6'-sulfo-Sialyl-Lewis$^{x}$", "Siaα2,3Galβ1,4GlcNAcβ1,3Galβ1,4 (Fucα1,3) GlcNAc: VIM-2 antigen", and "Siaα2,3Galβ1,4(Fucα1,3) GlcNAcβ1,3Galβ1,4 (Fucα1,3)GlcNAc: Sialyl-Lewis$^{x}$-i".

[1-3] Here, Z is preferably a single bond or O, S or NH, but may be a linker bound to thiomethyl or an aminomethylated sugar alcohol.

The linker bound to thiomethyl is preferably selected from commercially available linkers such as BMPH (N-β-Maleimidopropionic acid hydrazide-TFA), KMUH (N-κ-Maleimidoundecanoic acid hydrazide-TFA), EMCH (N-[ε-Maleimidocaproic acid]hydrazide-TFA), MPBH (4-[4-N-Maleimidophenyl]butyric acid hydrazide-HCl) and PDPH (3-[2-Pyridyldithio]propionyl hydrazide) (manufactured by Thermo Fisher scientific Inc.), and an aminomethylated sugar alcohol is preferably selected from N-acetylglucosaminitol, N-acetylgalactosaminitol, mannitol and galactitol.

Preferable embodiments of n1 include 14 to 39, 16 to 31, 17 to 28, and 20 to 40, more preferable embodiments include 20 to 28 and 21 to 27, and the most preferable embodiment is 22 to 24.

n2 represents an integer from 1 to 27, preferable embodiments thereof include 2 to 15, 2 to 13, and 3 to 13, more preferable embodiments include 5 to 13 and 6 to 12, and the most preferable embodiment is 7 to 11.

m represents an integer from 1 to 30, is preferably an integer from 1 to 10, and more preferably an integer from 1 to 3.

[1-4] The invention according to the immunity inducing method of the present invention can be also described as follows.

An immunity inducing method which is antigen-specific to a target oligosaccharide antigen R including a process of synthesizing an artificial glycolipid expressed by the general formula (2) and obtained by conjugating a carrier compound expressed by the general formula (1) or a salt thereof to a target oligosaccharide antigen R containing a linear chain or branched oligosaccharide constituted with 2 to 30 of one type or plural types of monosaccharides and immunizing a mammal using an immunity inducer containing the glycolipid or a salt thereof as an effective component:

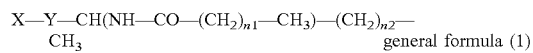
general formula (1)

(wherein X represents —H, —OH, —SH, —NH$_2$, halogen or a hydrazide group, Y represents —(CH$_2$)$_m$—, n1 represents an integer from 2 to 40, n2 represents an integer from 1 to 27, and m represents an integer from 1 to 30):

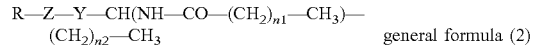
general formula (2)

(wherein R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —(CH$_2$)$_m$—, n1 represents an integer from 2 to 40, n2 represents an integer from 1 to 27, and m represents an integer from 1 to 30).

Here, preferable cases of the target oligosaccharide antigen R, Z and n1, n2 and m in the formula are the same as described above in [1-2] and [1-3].

[1-5] The invention according to the immunity inducing method of the present invention can be also described as follows.

An immunity inducing method which is antigen-specific to a target oligosaccharide antigen R in mammals including a process of administering an immunity inducer containing an artificial glycolipid expressed by the general formula (2) and obtained by conjugating a target oligosaccharide antigen R and a carrier compound expressed by the general formula (1) or a salt thereof as an effective component to a mammal:

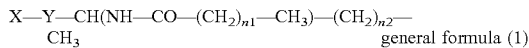
general formula (1)

(wherein X represents —H, —OH, —SH, —NH$_2$, halogen or a hydrazide group, Y represents —(CH$_2$)$_m$-, n1 represents an integer from 2 to 40, n2 represents an integer from 1 to 27, and m represents an integer from 1 to 30):

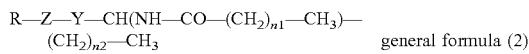
general formula (2)

(wherein R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —(CH$_2$)$_m$—, n1 represents an integer from 2 to 40, n2 represents an integer from 1 to 27, and m represents an integer from 1 to 30).

Here, preferable cases of the target oligosaccharide antigen R, Z and n1, n2 and m in the formula are the same as described above in [1-2] and [1-3].

[2] The present invention also relates to an invention according to an immunity inducer described below.

[2-1] An immunity inducer including an artificial glycolipid which includes the target oligosaccharide antigen R and is expressed by the general formula (2) described below or a salt thereof as an effective component:

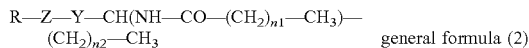
general formula (2)

(wherein R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —(CH$_2$)$_m$—, n1 represents an integer from 2 to 40, n2 represents an integer from 1 to 27, and m represents an integer from 1 to 30).

Here, preferable cases of the target oligosaccharide antigen R, Z and n1, n2 and m in the formula are the same as described above in [1-2] and [1-3].

The invention according to the immunity inducer of the present invention can be also expressed as follows.

[2-2] An artificial glycolipid containing a target oligosaccharide antigen R expressed by the following general formula (2) or a salt thereof, which is an artificial glycolipid or a salt thereof for a use in an immunity inducing method antigen-specific to the target oligosaccharide antigen R:

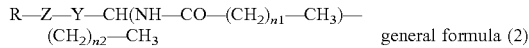
general formula (2)

(wherein R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —(CH$_2$)m-, n1 represents an integer from 2 to 40, n2 represents an integer from 1 to 27, and m represents an integer from 1 to 30).

Here, preferable cases of the target oligosaccharide antigen R, Z and n1, n2 and m in the formula are the same as described above in [1-2] and [1-3].

[2-3] A use of an artificial glycolipid containing a target oligosaccharide antigen R expressed by the following general formula (2) or a salt thereof, which is a use of an artificial glycolipid or a salt thereof for production of an immunity inducer to the target oligosaccharide antigen R:

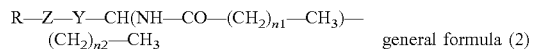
general formula (2)

(wherein R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —(CH$_2$)m-, n1 represents an integer from 2 to 40, n2 represents an integer from 1 to 27, and m represents an integer from 1 to 30).

Here, preferable cases of the target oligosaccharide antigen R, Z and n1, n2 and m in the formula are the same as described above in [1-2] and [1-3].

[3] The present invention also relates to an invention according to the vaccine described below.

[3-1] A vaccine including an artificial glycolipid which is expressed by the general formula (2) described below and includes the target oligosaccharide antigen R or a salt thereof as an effective component:

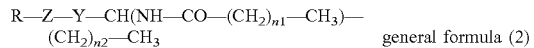
general formula (2)

(wherein R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —(CH$_2$)$_m$—, n1 represents an integer from 2 to 40, n2 represents an integer from 1 to 27, and m represents an integer from 1 to 30).

Here, the vaccine is a vaccine having an action causing immunity induction which is antigen-specific to a target oligosaccharide antigen R, and preferable cases of the target oligosaccharide antigen R, Z and n1, n2 and m in the formula are the same as described above in [1-2] and [1-3]. The invention relating to the vaccine according to the present invention can be also described as follows.

[3-2] An artificial glycolipid or a salt thereof containing a target oligosaccharide antigen R expressed by the following general formula (2), which is an artificial glycolipid or a salt thereof for a use in a vaccine inoculation method to the target oligosaccharide antigen R:

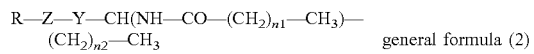
general formula (2)

(wherein R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —(CH$_2$)$_m$—, n1 represents an integer from 2 to 40, n2 represents an integer from 1 to 27, and m represents an integer from 1 to 30).

Here, preferable cases of the target oligosaccharide antigen R, Z and n1, n2 and m in the formula are the same as described in [1-2] and [1-3].

[3-3] A use of an artificial glycolipid containing a target oligosaccharide antigen R expressed by the following general formula (2) or a salt thereof, which is a use of an artificial glycolipid or a salt thereof for production of a vaccine:

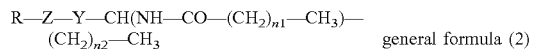
general formula (2)

(wherein R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —$(CH_2)_m$—, n1 represents an integer from 2 to 40, n2 represents an integer from 1 to 27, and m represents an integer from 1 to 30).

Here, preferable cases of the target oligosaccharide antigen R, Z and n1, n2 and m in the formula are the same as described above in [1-2] and [1-3].

[4] The present invention also relates to an invention according to a novel artificial glycolipid expressed by the following general formula (2) or a salt thereof itself among the artificial glycolipids each obtained by conjugating a target oligosaccharide antigen R and a carrier compound or salts thereof, which are used in the inventions relating to [1] the immunity inducing method, [2] the immunity inducer or [3] the vaccine:

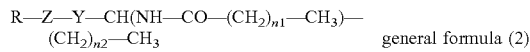
general formula (2)

(wherein R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —$(CH_2)_m$—, n1 represents an integer from 20 to 40, n2 represents an integer from 1 to 27, and m represents an integer from 1 to 30).

Here, n1 in the formula is corresponded to a fatty acid having 22 or more carbon atoms, which is classified into a very long chain fatty acid, and n1 is an integer of 20 or more and from 20 to 40, preferably from 20 to 28, more preferably from 21 to 27, and the most preferably 22 to 24.

Here, preferable cases of the target oligosaccharide antigen R, Z and n2 and m in the formula are the same as described above in [1-2] and [1-3].

[5] The invention according to an artificial glycolipid or a salt thereof of the present invention can be also expressed as "the artificial glycolipid or a salt thereof described in [4], which has immunity inducing activity to the target oligosaccharide antigen R, and also expressed as "the artificial glycolipid described in [4] or a salt thereof for immunity induction to the oligosaccharide R".

[6] The present invention also relates to a carrier compound itself containing a novel artificial lipid expressed by the following general formula (1) or a salt thereof among the carrier compound or a salt thereof, which has an activity causing an immunity inducing activity to a target oligosaccharide antigen R, by using in the state of conjugating to the target oligosaccharide antigen R in the immunity inducing method according to [1] described above.

That is, the invention according to the novel artificial lipid or a salt thereof of the present invention can be also expressed as follows.

An artificial lipid expressed by the following general formula (1) or a salt thereof;

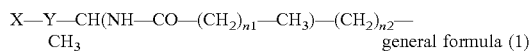
general formula (1)

(wherein X represents —H, —OH, —SH, —$NH_2$, halogen or a hydrazide group, Y represents —$(CH_2)_m$—, n1 represents an integer from 20 to 40, n2 represents an integer from 1 to 27, and m represents an integer from 1 to 30).

Here, preferable cases of the target oligosaccharide antigen R, Z and, n2 and m are the same as described above in [1-2] and [1-3], and preferable cases of n1 are the same as described above in [4].

[7] An invention according to the artificial lipid or a salt thereof of the present invention is characterized for a specific application, and can be expressed as "a carrier compound containing an artificial lipid expressed by the following general formula (1) or a salt thereof", "a carrier compound containing an artificial lipid expressed by the following general formula (1) or a salt thereof and having an activity which causes an immunity inducing activity to a target oligosaccharide antigen R by bonding to the reducing end side of the target oligosaccharide antigen R", "an artificial lipid expressed by the following general formula (1) or a salt thereof, which is an artificial lipid or a salt thereof for a use in a method of causing an immunity inducing activity to a target oligosaccharide antigen R by bonding to the reducing end side of the target oligosaccharide antigen R as a carrier compound in the immunity inducing method to the target oligosaccharide antigen R", "a use of an artificial lipid expressed by the following general formula (1) or a salt thereof for production of an immunity inducer to a target oligosaccharide antigen R, wherein the immunity inducer is obtained by bonding the artificial lipid or a salt thereof to the reducing end side of the target oligosaccharide antigen R", and so on.

Advantageous Effects of Invention

By a use of the carrier compound of the present invention, even an oligosaccharide antigen contained in an N-linked sugar chain of a glycoprotein, which is recognized to have a difficulty in immunity induction, enables its immunogenicity to be significantly enhanced. Particularly when a carrier compound having a very long chain lipid is used (a3-1), as compared to a case of giving simple lipid modification (a2), the carrier compound has an immunogenicity enhancing action as much as a serum antibody titer to an oligosaccharide antigen being an immunogen is approximately 12 times and a serum antibody titer to a glycoprotein (Fetuin) containing an objective sugar chain is approximately 8 times (FIG. 3).

A monoclonal antibody reacting with CDw75 by immunizing with an immunity inducer containing a CDw75 oligosaccharide chain is produced also in the conventional technique (Non Patent Literature 8); however, a specific anti-CDw75 antibody is not obtained in a rigorous sense, and when various experimental data on a CDw75 reactive antibody (241-5-2 antibody) described in the literature is compared to data in preparation of the anti-CDw75 antibody obtained in the present invention, an appearance ratio of positive hybridoma cells that produce a target antibody after immunity induction was as high as approximately 13 times. Furthermore, affinity to an epitope of the finally obtained monoclonal antibody was as high as approximately 3,000 times.

The immunogenicity enhancing effect by the carrier compound of the present invention made it possible to develop a monoclonal antibody having high specificity and affinity to an objective carbohydrate epitope and its producing hybridoma cell from a host animal after immunity.

The immunity inducer of the present invention is confirmed to have an ability capable of provoking production of an IgG-class antibody produced by class switching in a mouse immunized with the immunity inducer, and has an activity as a thymus-dependent antigen. The activity is not confirmed in conventional techniques using an immunity inducer containing phosphatidyl ethanolamine as a carrier compound (Non Patent Literatures 7 and 8).

There was a report that, in the case of trying production of an antibody to a microorganism-derived oligosaccharide chain, an IgG antibody was produced by immunization with a conjugate with a carrier compound such as KLH, BSA, biotin and avidin, although its affinity was low (Non Patent Literatures 9, 10 and 12); however, the present invention can produce an antibody having high affinity by inducing immunity accompanied by class switching in an oligosaccharide antigen that is a mammal-derived oligosaccharide chain and contained in an N-linked sugar chain of a glycoprotein for the first time.

As described above, the immunity inducer of the present invention is recognized as a thymus-dependent antigen in an immunity system and thus can undergo enhancement processes of specificity and affinity of an antibody such as class switching and maturity of affinity and, therefore, an antibody having high specificity and affinity can be obtained.

According to the method of conjugating a carrier compound and a target oligosaccharide chain in the present invention, an immunity inducer can be produced by bonding a carrier compound and a target oligosaccharide chain with keeping the structure of the oligosaccharide chain.

Since a target oligosaccharide chain is generally conjugated by a reductive amination method in the case of the carrier compound used in the conventional techniques (Non Patent Literatures 7 to 12), the sugar chain is cleaved at a bonding site (sugar in the reducing side) with a carrier compound and an immunity inducer cannot be synthesized with keeping the structure of the target oligosaccharide chain.

In the case of the carrier compound capable of enhancing immunogenicity of any oligosaccharide chain, which is provided by the present invention, effective formulation of an "oligosaccharide chain-carrier compound" conjugate as an immunity inducer is possible, and development of a monoclonal antibody which recognizes a sugar chain epitope, a vaccine which targets the sugar chain, and the like, are facilitated.

DESCRIPTION OF EMBODIMENTS

Figure 1:
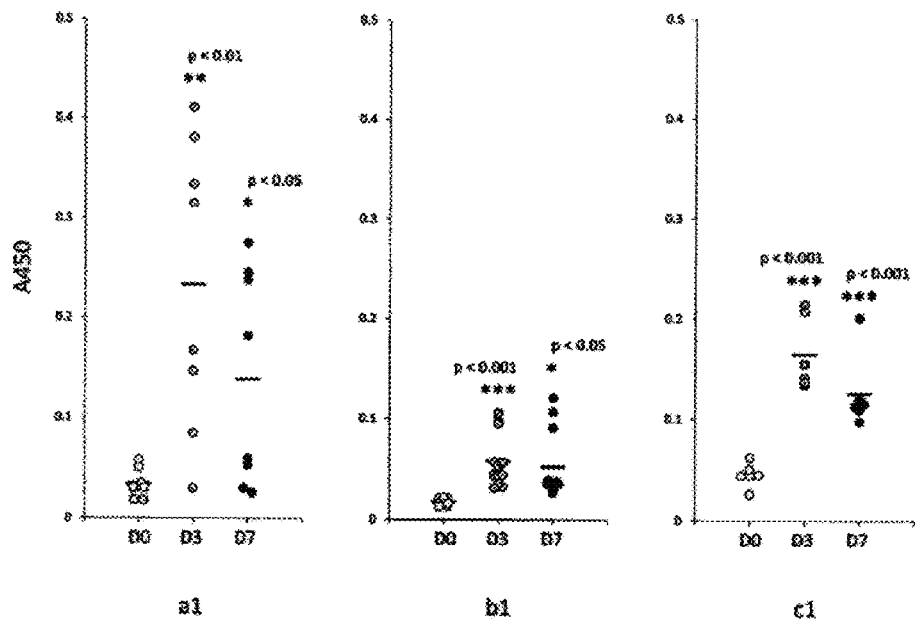
FIG. 1 illustrates serum antibody titers to an immunogen after immunity induction: a serum antibody titer to an immunogen after immunizing a mouse using each of compounds a1, b1 and c1 as an immunity inducer was measured by ELISA. White circles denote antibody titers in unimmunized mouse serums (D0), gray circles denote antibody titers in mouse serums after 3 days from the final immunization (D3), black circles denote antibody titers in mouse serums after 7 days from the final immunization (D7); and the antibody titers in mouse serums were individually plotted in the graphs (n=6 to 12). It was confirmed that, as compared to the serum antibody titers in unimmunized mice, each of the serum antibody titers of D3 and D7 significantly increased by a Student's t test. ($*p<0.05$, $p<0.01$, $*p<0.001$)

1. Objective Carbohydrate Antigen in the Present Invention (1-1) Regarding Target Oligosaccharide Antigen When referring to "oligosaccharide antigen" or simply "carbohydrate antigen" in the present invention, it means the oligosaccharide chain itself or an oligosaccharide chain having a stimulating activity of an antibody producing cell in a modified product thereof. The immunity inducing method of the present invention is capable of enhancing immunogenicity to any oligosaccharide antigen as an object, and a typical target "oligosaccharide antigen" in the present invention is an oligosaccharide antigen existing as the entire or a part of a sugar chain structure in a sugar chain region, which is contained in complex carbohydrates such as secreted glycoproteins of various organisms and glycoproteins or glycolipids that constitutes a cell membrane, and constituted with 2 to 30 saccharides, preferably 2 to 16 saccharides, and more preferably 2 to 6 saccharides. That is, the "oligosaccharide antigen (R)" of the present invention is constituted with "a linear chain or branched oligosaccharide having a sugar chain structure contained in a complex carbohydrate and constituted with one or plural types of 2 to 30 monosaccharides". In particular, an oligosaccharide antigen having a sugar chain structure contained in an N-linked sugar chain shown in a mammalian cell-derived glycoprotein is preferable.

That is, the carbohydrate antigen (R) to be the object in the present invention can be expressed as a linear chain or branched molecule containing, as a constitutional element, one or plural types of monosaccharides selected from sialic acid (N-acetylneuraminic acid, N-glycolylneuraminic acid, α-ketodeoxynononic acid), galactose, glucose, N-acetylglucosamine, N-acetylgalactosamine, glucosamine, galactosamine, mannose, fucose, xylose, glucuronic acid, iduronic acid, inositol, erythrose, erythronic acid, erythruronic acid, erythraric acid, erythritol, threose, threonic acid, threuronic acid, threaric acid, threitol, ribose, ribonic acid, riburonic acid, ribaric acid, ribitol, arabinose, arabinonic acid, arabinuronic acid, arabinaric acid, arabinitol, xylonic acid, xyluronic acid, xylaric acid, xylitol, lyxose, lyxonic acid, lyxuronic acid, allose, allonic acid, alluronic acid, allaric acid, allitol, altrose, altronic acid, altruronic acid, altraric acid, altritol, gluconic acid, glucaric acid, glucitol, mannonic acid, mannuronic acid, mannaric acid, mannitol, gulose, gulonic acid, guluronic acid, idose, idonic acid, idaric acid, iditol, galactonic acid, galacturonic acid, galactaric acid, galactitol, talose, talonic acid, taluronic acid, dihydroxyacetone, erythrulose, ribulose, psicose, fructose, sorbose, tagatose, sedoheptulose, coriose, deoxyribose, rhamnose, fuculose, alomethylose, quinovose, antiarose, talomethylose, digitalose, digitoxose, cymarose, tyvelose, abequose, paratose, colitose, ascarylose, and sulfated, acetylated, phosphorylated or methylated sugars of these monosaccharides, preferably sialic acid, galactose, glucose, N-acetylglucosamine, N-acetylgalactosamine, glucosamine, galactosamin, mannose, fucose, xylose, glucuronic acid, iduronic acid, inositol, and sulfated, acetylated or methylated sugars of these monosaccharides, and the number of monosaccharides which constitute R is 2 to 30, preferably 2 to 16, and more preferably 2 to 6.

Cell membrane surfaces of various mammal cells, plant cells, yeasts and bacteria are covered with various complex carbohydrates derived from glycoprotein, glycolipid, and the like, which constitute the cell membranes, and in the case of having a complex carbohydrate characteristic to a derived cell among the various cell-derived complex carbohydrates, such a complex carbohydrate becomes a discrimination marker of each cell as an oligosaccharide antigen. For example, in case of a pathogenic bacterium, the pathogenic bacterium becomes a biomarker for a diagnostic or pharmaceutical target. For example, O antigens of eubacterium have been known.

(1-2) Regarding Mammal Cell-derived Oligosaccharide Antigen

There are a large number of reports that complex carbohydrates each having a complex sugar chain constituted with a structure characteristic to a cell surface are expressed in mammalian cells reflecting a pathologic condition particularly such as cancer cells and severe diseases, and these complex sugar chains also become diagnostic markers and biomarkers for pharmaceutical targets. For example, CA19-9 (Sialyl-Lewis$^a$) has been known as a marker of digestive cancer.

Therefore, an oligosaccharide antigen mainly contained in mammalian cell-derived complex carbohydrate is used as an object in the present invention.

Typical sugar chain structure of such known mammalian cell-derived oligosaccharide antigens are classified into the following (A) to (D).

Examples include Siaα2,6Galβ1,4GlcNAc, Siaα2,3Galβ1,4GlcNAc, Galβ1,4GlcNAc, Galβ1,3GlcNAc, Siaα2,3Galβ1,4(Fucα1,3)GlcNAc, Galβ1,4(Fucα1,3)GlcNAc, Siaα2,3Galβ1,3(Fucα1,4)GlcNAc, Siaα2,3Galβ1,3GlcNAc, Galβ1,3(Fucα1,4)GlcNAc, Siaα2,3Galβ1,3(Siaα2,6)GlcNAc, Siaα2,3Galβ1,3(Fucα1,4)(Siaα2,6)GlcNAc, Fucα1,2Galβ1,3(Fucα1,4) GlcNAc, Fucα1,2Galβ1,4GlcNAc, Fucα1,2Galβ1,4(Fucα1,3)GlcNAc, Fucα1,6GlcNAc, GlcNAcβ1,4(Fucα1,6)GlcNAc, Manβ1,4GlcNAcβ1,4(Fucα1,6)GlcNAc, Manα1,6(Manα1,3)Manβ1,4GlcNAcβ1,4(Fucα1,6)GlcNAc, Manα1,6(GlcNAcβ1,4)(Manα1,3)Manβ1,4GlcNAcβ1,4GlcNAc, Manα1,6(GlcNAcβ1,4)(Manα1,3)Manβ1,4GlcNAcβ1,4(Fucα1,6)GlcNAc, GlcNAcβ1,4GlcNAc, Manβ1,4GlcNAcβ1,4GlcNAc, GlcNAcβ1,2Man, GlcNAcβ1,4Man, GlcNAcβ1,6Man, Galβ1,3GlcNAcβ1,2Man, Galβ1,3GlcNAcβ1,4Man, Galβ1,3GlcNAcβ1,6Man, Galβ1,4GlcNAcβ1,2Man, Galβ1,4GlcNAcβ1,4Man, Galβ1,4GlcNAcβ1,6Man, Siaα2,3Galβ1,4GlcNAcβ1,2Man, Siaα2,3Galβ1,4GlcNAcβ1,4Man, Siaα2,3Galβ1,4GlcNAcβ1,6Man, Siaα2,3Galβ1,3GlcNAcβ1,2Man, Siaα2,3Galβ1,3GlcNAcβ1,4Man, Siaα2,3Galβ1,3GlcNAcβ1,6Man, Siaα2,6Galβ1,4GlcNAcβ1,2Man, Siaα2,6Galβ1,4GlcNAcβ1,4Man, Siaα2,6Galβ1,4GlcNAcβ1,6Man, GalNAcβ1,4GlcNAc, GalNAcβ1,4GlcNAcβ1,2Man, GalNAc(4SO$_4$)β1,4GlcNAc, GalNAc(4SO$_4$)β1,4GlcNAcβ1,2Man, GalNAc(4SO$_4$)β1,4GlcNAcβ1,4Man, GalNAc(4SO$_4$)β1,4GlcNAcβ1,6Man, GlcNAcβ1,3Galβ1,4GlcNAc, GlcA(3SO$_4$)β1,3Galβ1,4GlcNAc, Siaα2,3Galβ1,4(Fucα1,3)GlcNAc(6SO$_4$), Siaα2,3Galβ1,4GlcNAc(6SO$_4$), Galβ1,4GlcNAc(6SO$_4$), Galβ1,4(Fucα1,3)GlcNAc(6SO$_4$), Siaα2,3Gal(6SO$_4$)β1,4(Fucα1,3)GlcNAc, Siaα2,3Gal(6SO$_4$)β1,4GlcNAc, Gal(6SO$_4$)β1,4GlcNAc, Gal(6SO$_4$)β1,4GlcNAc(6SO$_4$), Galβ1,4GlcNAcβ1,3Gal, GlcNAcβ1,3Galβ1,4GlcNAc, Galβ1,4GlcNAc(6SO$_4$)β1,3Gal, GlcNAc(6SO$_4$)β1,3Galβ1,4GlcNAc, Gal(6SO$_4$)β1,4GlcNAc(6SO$_4$)β1,3Gal, GlcNAc(6SO$_4$)β1,3Gal(6SO$_4$)β1,4GlcNAc, Siaα2,3Galβ1,4GlcNAcβ1,3Galβ1,4(Fucα1,3)GlcNAc, Fucα1,2Galβ1,3GlcNAc, Galα1,3(Fucα1,2)Galβ1,3GlcNAc, Galα1,3(Fucα1,2)Galβ1,4GlcNAc, GalNAcα1,3(Fucα1,2)Galβ1,3GlcNAc, GalNAcα1,3(Fucα1,2)Galβ1,4GlcNAc, Fucα1,2Galβ1,4(Fucα1,3)GlcNAcβ1,3Gal, Gal(3SO$_4$)β1,4GlcNAc, Gal(3SO$_4$)β1,4(Fucα1,3)GlcNAc, Gal(3SO$_4$)β1,3GlcNAc, Gal(3SO$_4$)β1,3(Fucα1,4)GlcNAc, Gal(3SO$_4$)β1,4GlcNAc(6SO$_4$), Gal(3SO$_4$)β1,4(Fucα1,3)GlcNAc(6SO$_4$), Siaα2,8Siaα2,8Sia, Siaα2,6GalNAcβ1,4GlcNAc, Siaα2,3Galβ1,4(Fucα1,3)GlcNAcβ1,3Galβ1,4(Fucα1,3)GlcNAc, Galβ1,4GlcNAcβ1,3(Galβ1,4GlcNAcβ1,6)Gal, and Siaα2,3Galβ1,4GlcNAcβ1,3(Siaα2,3Galβ1,4GlcNAcβ1,6)Gal.

(B) O-linked Sugar Chains (Glycoproteins)

Examples include Siaα2,3Galβ1,3GalNAc, Galβ1,3GalNAc, Siaα2,3Galβ1,3(GlcNAcβ1,6)GalNAc, GalNAcα1,3GalNAc, GlcNAcβ1,3(Siaα2,6)GalNAc, GalNAcα1,6GalNAc, GlcNAcβ1,6GalNAc, Fucα1,2GalNAc, Galβ1,3(GlcNAcβ1,6)GalNAc, Siaα2,6GalNAc, Siaα2,6(GlcNAcβ1,6)GalNAc, Siaα2,3Galβ1,3(Siaα2,6)GalNAc, Galβ1,4GalNAc, Siaα2,3Galβ1,4GalNAc, GlcNAcα1,4Gal, GlcNAcα1,4Galβ1,4GlcNAc, GlcNAcα1,4Galβ1,4GalNAc, GlcNAcα1,4Galβ1,4(GlcNAcα1,4Galβ1,4GlcNAcβ1,6)GalNAc, Siaα2,3Galβ1,4(Fucα1,3)GlcNAc(6SO$_4$)β1,6GalNAc, Gal(3SO$_4$)β1,4GlcNAcβ1,6(Siaα2,3Galβ1,3)GalNAc, Siaα2,3Galβ1,4(Fucα1,3)GlcNAc(6SO$_4$)β1,3Galβ1,3GalNAc, Siaα2,3Galβ1,4(Fucα1,3)GlcNAc(6SO$_4$)β1,3Galβ1,3(Siaα2,3Galβ1,4(Fucα1,3)GlcNAc(6SO$_4$)β1,6)GalNAc, Siaα2,3Gal(6SO$_4$)β1,4GlcNAcβ1,3Galβ1,3GalNAc, Gal(3SO$_4$)β1,3GalNAc(6SO$_4$), Siaα2,3Galβ1,3GalNAc(6SO$_4$), Gal(3SO$_4$β1,3(Siaα2,6)GalNAc, and Gal(3SO$_4$)β1,3GalNAc.

Examples include Galβ1,4Xyl, Galβ1,3Galβ1,4Xyl, GlcAβ1,3Galβ1,3Galβ1,4Xyl, GalNAcβ1,4IdoAα1,3Galβ1,3Galβ1,4Xyl, GalNAcβ1,4GlcAβ1,3Galβ1,3Galβ1,4Xyl, GlcNAcα1,4GlcAβ1,3Galβ1,3Galβ1,4Xyl, GlcAβ1,3GalNAcβ1,4GlcA, GalNAcβ1,4GlcAβ1,3GalNAc, GlcAβ1,3GalNAc(4SO$_4$)β1,4GlcA, GalNAc(4SO$_4$)β1,4GlcAβ1,3GalNAc, GlcAβ1,3GalNAc(6SO$_4$)β1,4GlcA, GalNAc(6SO$_4$)β1,4GlcAβ1,3GalNAc, GlcA(2SO$_4$β1,3(6SO$_4$)GalNAcβ1,4GlcA, GalNAc(6SO$_4$)β1,4GlcA(2SO$_4$)β1,3GalNAc, GlcAβ1,3GalNAc(4,6SO$_4$)β1,4GlcA, GalNAc(4,6SO$_4$)β1,4GlcAβ1,3GalNAc, GalNAc(4,6SO$_4$)β1,4GlcA(2SO$_4$)β1,3GalNAc(6SO$_4$), IdoAα1,3GalNAcβ1,4IdoA, GalNAcβ1,4IdoAα1,3GalNAc, IdoAα1,3GalNAc(4SO$_4$)β1,4IdoA, GalNAc(4SO$_4$)β1,4IdoAα1,3GalNAc, GlcAβ1,4GlcNAcα1,4GlcA, GlcNAcα1,4GlcAβ1,4GlcNAc, GlcA(2SO$_4$)β1,4GlcNAcα1,4GlcA, GlcNAcα1,4GlcA(2SO$_4$)β1,4GlcNAc, IdoA(2SO$_4$)α1,4GlcNAcα1,4GlcA, GlcNAcα1,4IdoA(2SO$_4$)α1,4GlcNAc, GlcA(2SO$_4$)β1,4GlcNSO$_3$α1,4GlcA, GlcNSO$_3$α1,4GlcA(2SO$_4$)β1,4GlcNAc, IdoA(2SO$_4$)α1,4GlcNSO$_3$Hα1,4GlcA, GlcNSO$_3$α1,4IdoA(2SO$_4$)α1,4GlcNAc, GlcAβ1,4GlcNα1,4GlcA, GlcAβ1,4GlcNSO$_3$α1,4GlcA, GlcNSO$_3$α1,4GlcAβ1,4GlcNAc, IdoAα1,4GlcNSO$_3$α1,4GlcA, GlcNSO$_3$α1,4IdoAα1,4GlcNAc, GlcAβ1,4GlcNSO$_3$(6SO$_4$)α1,4GlcA, GlcNSO$_3$(6SO$_4$)α1,4GlcAβ1,4GlcNAc, IdoAα1,4GlcNSO$_3$(6SO$_4$)α1,4GlcA, GlcNSO$_3$(6SO$_4$)α1,4IdoAα1,4GlcNAc, IdoA(2SO$_4$)α1,4GlcNSO$_3$(6SO$_4$)α1,4GlcA, GlcNSO$_3$(6SO$_4$)α1,4IdoA(2SO$_4$)α1,4GlcNAc, IdoAα1,4GlcNSO$_3$α1,4IdoA, GlcAβ1,3GlcNAcβ1,4GlcA, GlcNAcβ1,4GlcAβ1,3GlcNAc, IdoAα1,4GlcNSO$_3$, IdoAα1,4GlcNSO$_3$(6SO$_4$), IdoA(2SO$_4$)α1,4GlcNSO$_3$, IdoA(2SO$_4$)α1,4GlcNSO$_3$(6SO$_4$), IdoA(2SO$_4$)α1,4GlcNSO$_3$(3SO$_4$), GlcAβ1,4GlcNSO$_3$, GlcAβ1,4GlcNSO$_3$(6SO$_4$), GlcA(2SO$_4$)β1,4GlcNAc, GlcA(2SO$_4$)β1,4GlcNSO$_3$(3SO$_4$), GlcAβ1,4GlcNSO$_3$(3,6SO$_4$), and GlcAβ1,4GlcNSO$_3$(3SO$_4$).

(D) Glycolipid Type Sugar Chains

Examples include Galα1,3Galβ1,4Glc, GalNAcβ1,3Galα1,3Galβ1,4Glc, Galβ1,3GalNAcβ1,3Galα1,3Galβ1,4Glc, Galα1,4Galβ1,4Glc, GalNAcα1,3Galα1,4Galβ1,4Glc, GalNAcα1,3GalNAcβ1,3Galα1,4Galβ1,4Glc, Galβ1, 3GalNAcβ1,3Galα1,4Galβ1,4Glc, Galα1,4Galβ1,4GlcNAcβ1,3Galβ1,4Glc, GlcNAcβ1,3Galβ1,4Glc, Galβ1,4GlcNAcβ1,3Galβ1,4Glc, Galβ1,4Glc, Siaα2,3Galβ1,4Glc, Siaα2,8Siaα2,3Galβ1,4Glc, Siaα2,8Siaα2,8Siaα2,3Galβ1,4Glc, GalNAcβ1,4Galβ1,4Glc, GalNAcβ1,4(Siaα2,3)Galβ1,4Glc, Galβ1,3GalNAcβ1,4Galβ1,4Glc, Galβ1,3GalNAcβ1,4(Siaα2,3)Galβ1,4Glc, Siaα2,3Galβ1,3GalNAcβ1,4Galβ1,4Glc, Siaα2,3Galβ1,3GalNAcβ1,4(Siaα2,3)Galβ1,4Glc, Siaα2,3Galβ1,3(Siaα2,6)GalNAcβ1,4Galβ1,4Glc, Siaα2,3Galβ1,3(Siaα2,6)GalNAcβ1,4(Siaα2,3)Galβ1,4Glc, Siaα2,3Galβ1,3GalNAcβ1,4(Siaα2,8Siaα2,3)Galβ1,4Glc, Siaα2,3Galβ1,3(Siaα2,6)GalNAcβ1,4(Siaα2,8Siaα2,3) Galβ1,4Glc, Siaα2,8Siaα2,3Galβ1,3GalNAcβ1,4(Siaα2,8Siaα2,3)Galβ1,4Glc, Siaα2,3Galβ1,3GalNAcβ1,3Galα1,4Galβ1,4Glc, Siaα2,3Galβ1,3(Siaα2,6)GalNAcβ1,3Galα1,4Galβ1,4Glc, Siaα2,3Galβ1,3GlcNAcβ1,3Galβ1,4Glc, Siaα2,3Galβ1,3(Siaα2,6)GlcNAcβ1,3Galβ1,4Glc, Galβ1,3GlcNAcβ1,3Galβ1,4Glc, Siaα2,3Galβ1,4GlcNAcβ1,3Galβ1,4Glc, Siaα2,8Siaα2,3Galβ1,4GlcNAcβ1,3Galβ1,4Glc, Siaα2,3Galβ1,3(Fucα1,4)GlcNAcβ1,3Galβ1,4Glc, Gal(3SO₄)β1,4Glc, GalNAcβ1,4Gal(3SO₄)β1,4Glc, GalNAc(3SO₄)β1,4Galβ1,4Glc, GalNAc(3SO₄)β1,4Gal(3SO₄)β1,4Glc, Gal(3SO₄)β1,3GalNAcβ1,4Gal(3SO₄)β1,4Glc, Gal(3SO₄)β1,3GalNAcβ1,4(Siaα2,3)Galβ1,4Glc, GalNAc(3SO₄)β1,3Galα1,4Galβ1,4Glc, Gal(3SO₄)β1,3GalNAcβ1,3Galα1,4Galβ1,4Glc, GalNAc(3SO₄)β1,3Galα1,3Galβ1,4Glc, Gal(3SO₄)β1,3GalNAcβ1,3Galα1,3Galβ1,4Glc, Siaα2,3Galβ1,4(Fucα1,3)GlcNAcβ1,3Galβ1,4(Fucα1,3)GlcNAcβ1,3Galβ1,4Glc, Siaα2,3Galβ1,4(Fucα1,3)GlcNAcβ1,3Galβ1,4GlcNAcβ1,3Galβ1,4Glc, Fucα1,2Galβ1,3GalNAcβ1,3Galα1,4Galβ1,4Glc, and Siaα2,3Gal.

In general, among these mammalian oligosaccharide antigens, immunity induction to a glycolipid type oligosaccharide antigen is considered to be comparatively easy. Also in a sugar chain structure, a glycolipid type oligosaccharide has a distinctive characteristic of containing a lactose structure (Galβ1,4Glc) in the reducing end, except for the GM4-type oligosaccharide (Siaα2,3Gal). Such a structure is not present in N-linked sugar chains, O-linked sugar chains, proteoglycan type sugar chains.

The immunity inducing method of the present invention can apply to any oligosaccharide antigen contained in N-linked sugar chains, O-linked sugar chains, proteoglycan type sugar chains and glycolipid type sugar chains and shows an immunogen enhancement activity; however, the object in the present invention is "an oligosaccharide antigen contained in an N-linked sugar chain" having low immunogenicity, to which an effective antibody cannot be provided, even though focused as a diagnostic marker for mainly severe diseases such as highly malignant cancers. In addition, when referring to "an oligosaccharide antigen contained in an N-linked sugar chain" in the present invention, it means an oligosaccharide antigen constituted with an N-linked sugar chain or a partial structure thereof in a mammal-derived glycoprotein.

Such "an oligosaccharide antigen contained in an N-linked sugar chain" is roughly classified into the following three types of sialylated carbohydrate (a), asialo carbohydrate (b) and fucosylated carbohydrate (c) (Essentials of Glycobiology, Cold Spring Harbor Laboratory Press, 1999).

(1-3) Regarding "Oligosaccharide Antigen Contained in N-linked Sugar Chain"

(a) N-linked Sugar Chains Classified into Sialylated Carbohydrate

Examples include Siaα2,6Galβ1,4GlcNAc, Siaα2,3Galβ1,4GlcNAc, Siaα2,3Galβ1,4(Fucα1,3)GlcNAc, Siaα2,3Galβ1,3(Fucα1,4)GlcNAc, Siaα2,3Galβ1,3GlcNAc, Siaα2,3Galβ1,3(Siaα2,6)GlcNAc, Siaα2,3Galβ1,3(Fucα1,4)(Siaα2,6)GlcNAc, Siaα2,3Galβ1,4GlcNAcβ1,2Man, Siaα2,3Galβ1,4GlcNAcβ1,4Man, Siaα2,3Galβ1,4GlcNAcβ1,6Man, Siaα2,3Galβ1,3GlcNAcβ1,2Man, Siaα2,3Galβ1,3GlcNAcβ1,4Man, Siaα2,3Galβ1,3GlcNAcβ1,6Man, Siaα2,6Galβ1,4GlcNAcβ1,2Man, Siaα2,6Galβ1,4GlcNAcβ1,4Man, Siaα2,6Galβ1,4GlcNAcβ1,6Man, Siaα2,3Galβ1,4(Fucα1,3)GlcNAc(6SO₄), Siaα2,3Galβ1,4GlcNAc(6SO₄), Siaα2,3Galβ1(6SO₄)β1,4GlcNAc, Siaα2,3Gal(6SO₄)β1,4(Fucα1,3)GlcNAc, Siaα2,3Galβ1,4GlcNAcβ1,3Galβ1,4(Fucα1,3)GlcNAc, Siaα2,8Siaα2,8Sia, Siaα2,6GalNAcβ1,4GlcNAc, Siaα2,3Galβ1,4(Fucα1,3)GlcNAcβ1,3Galβ1,4(Fucα1,3)GlcNAc, and Siaα2,3Galβ1,4GlcNAcβ1,3(Siaα2,3Galβ1,4GlcNAcβ1,6)Gal.

Among them, examples of particularly typical and useful sialylated carbohydrates include "Siaα2,6Galβ1,4GlcNAc: CDw75", "Siaα2,3Galβ1,4GlcNAc: 3'-Sialyl-LacNAc", "Siaα2,3Galβ1,3(Fucα1,4)GlcNAc: Sialyl-Lewis$^x$", "Siaα2,3Galβ1,3(Fucα1,4)(Siaα2,6)GlcNAc: Disialyl-Lewis$^a$", "Siaα2,3Galβ1,4(Fucα1,3)GlcNAc(6SO₄): 6-sulfo-Sialyl-Lewis$^x$", "Siaα2,3Gal(6SO₄)β1,4(Fucα1,3)GlcNAc: 6'-sulfo-Sialyl-Lewis$^x$", "Siaα2,3Galβ1,4GlcNAcβ1,3Galβ1,4(Fucα1,3)GlcNAc: VIM-2 antigen", "Siaα2,6GalNAcβ1,4GlcNAc", "Siaα2,3Galβ1,4(Fucα1,3)GlcNAcβ1,3Galβ1,4(Fucα1,3)GlcNAc: Sialyl-Lewis$^x$-i" and "Siaα2,3Galβ1,4GlcNAcβ1,3(Siaα2,3Galβ1,4GlcNAcβ1,6)Gal: Sialyl-I".

(b) N-linked Sugar Chains Classified into Asialo Carbohydrates (Non-sialylated Carbohydrates)

Examples include Galβ1,4GlcNAc, Galβ1,3GlcNAc, Galβ1,4 (Fucα1,3) GlcNAc, Galβ1,3 (Fucα1,4)GlcNAc, Fucα1,2Galβ1,3(Fucα1,4)GlcNAc, Fucα1,2Galβ1,4GlcNAc, Fucα1,2Galβ1,4(Fucα1,3)GlcNAc, Fucα1,6GlcNAc, GlcNAcβ1,4 (Fucα1,6)GlcNAc, Manβ1,4GlcNAcβ1,4 (Fucα1,6)GlcNAc, Manα1,6(Manα1,3)Manβ1,4GlcNAcβ1,4 (Fucα1,6)GlcNAc, Manα1,6 (GlcNAcβ1,4)(Manα1,3)Manβ1,4GlcNAcβ1,4 (Fucα1,6)GlcNAc, Manα1,6(GlcNAcβ3,4) (Manα1,3)Manβ1,4GlcNAcβ1,4GlcNAc, GlcNAcβ1,4GlcNAc, Manβ1,4GlcNAcβ1,4GlcNAc, GlcNAcβ1,2Man, GlcNAcβ1,4Man, GlcNAcβ1,6Man, Galβ1,3GlcNAcβ1,2Man, Galβ1,3GlcNAcβ1,4Man, Galβ1,3GlcNAcβ1,6Man, Galβ1,4GlcNAcβ1,2Man, Galβ1,4GlcNAcβ1,4Man, Galβ1,4GlcNAcβ1,6Man, GalNAcβ1,4GlcNAc, GalNAcβ1,4GlcNAcβ1,2Man, GalNAc(4SO₄)β1,4GlcNAc, GalNAc(4SO₄)β1,4GlcNAcβ1,2Man, GalNAc(4SO₄)β1,4GlcNAcβ1,4Man, GalNAc(4SO₄)β1,4GlcNAcβ1,6Man, GlcAβ1,3Galβ1,4GlcNAc, GlcA(3SO₄)β1,3Galβ1,4GlcNAc, Galβ1,4GlcNAc(6SO₄), Galβ1,4 (Fucα1,3)GlcNAc(6SO₄), Gal(6SO₄)β1,4GlcNAc, Gal(6SO₄)β1,4GlcNAc(6SO₄), Galβ1,4GlcNAcβ1,3Gal, GlcNAcβ1,3Galβ1,4GlcNAc, Galβ1,4GlcNAc(6SO₄)β1,3Gal, GlcNAc(6SO₄)β1,3Galβ1,4GlcNAc, Gal(6SO₄)β1,4GlcNAc(6SO₄)β1,3Gal, GlcNAc(6SO₄)β1,3Gal(6SO₄)β1,4GlcNAc, Fucα1,2Galβ1,3GlcNAc, Galα1,3(Fucα1,2)Galβ1,3GlcNAc, Galα1,3(Fucα1,2)Galβ1,4GlcNAc, GalNAcα1,3(Fucα1,2)Galβ1,3GlcNAc, GalNAcα1,3(Fucα1,2)Galβ1,4GlcNAc, Fucα1,2Galβ1,4(Fucα1,3)GlcNAcβ1,3Gal, Gal(3SO₄)β1,4GlcNAc, Gal(3SO₄)β1,4(Fucα1,3)GlcNAc, Gal(3SO₄)β1,3GlcNAc, Gal(3SO₄)β1,3(Fucα1,4)GlcNAc, Gal(3SO₄)β1,4GlcNAc(6SO₄), Gal(3SO₄)β1,4(Fucα1,3)GlcNAc(6SO₄) and Galβ1,4GlcNAcβ1,3(Galβ1,4GlcNAcβ1,6)Gal.

Among them, examples of particularly typical and useful asialo carbohydrates (non-sialylated carbohydrates) include "Galβ1,4GlcNAc: LacNAc", "GlcNAcβ1,4Man", "GlcNAcβ1,6Man", "Galβ1,4GlcNAcβ1,6Man", "GalNAcβ1,4GlcNAc", "GalNAcβ1,4GlcNAcβ1,2Man", "GalNAc(4SO$_4$)β1,4GlcNAc", "Galβ1,4 (Fucα1,3)Glc-NAc: Lewis$^x$", "Galβ1,3 (Fucα1,4)GlcNAc: Lewis$^a$", "Fucα1,2Galβ1,3(Fucα1,4)GlcNAc: Lewis$^b$", "Fucα1,2Galβ1,4(Fucα1,3) GlcNAc: Lewis$^y$", "Fucα1,6GlcNAc", "GlcNAcβ1,4 (Fucα1,6)GlcNAc", "Manβ1,4GlcNAcβ1,4 (Fucα1,6)GlcNAc", "Manα1,6(Manα1,3)Manβ1,4GlcNAcβ1,4 (Fucα1,6)GlcNAc" and "Galβ1,4GlcNAcβ1,3(Galβ1,4GlcNAcβ1,6)Gal: I-antigen".

(c) N-linked Sugar Chains Classified into Fucosylated Carbohydrates

Examples include Siaα2,3Galβ1,4(Fucα1,3)GlcNAc, Galβ1,4(Fucα1,3)GlcNAc, Siaα2,3Galβ1,3 (Fucα1,4)GlcNAc, Galβ1,3(Fucα1,4)GlcNAc, Siaα2,3Galβ1,3(Fucα1,4) (Siaα2,6)GlcNAc, Fucα1,2Galβ1,3 (Fucα1,4) GlcNAc, Fucα1,2Galβ1,4GlcNAc, Fucα1,2Galβ1,4 (Fucα1,3)GlcNAc, Fucα1,6GlcNAc, GlcNAcβ1,4(Fucα1,6)GlcNAc, Manβ1,4GlcNAcβ1,4 (Fucα1,6)GlcNAc, Manα1,6(Manα1,3)Manβ1,4GlcNAcβ1,4 (Fucα1,6)GlcNAc, Manα1,6(GlcNAcβ1,4)(Manα1,3)Manβ1,4GlcNAcβ1,4 (Fucα1,6)GlcNAc, Siaα2,3Galβ1,4(Fucα1,3)GlcNAc (6SO$_4$), Galβ1,4(Fucα1,3)GlcNAc(6SO$_4$), Siaα2,3Gal (6SO$_4$)β1,4(Fucα1,3)GlcNAc, Siaα2,3Galβ1,4GlcNAcβ1,3Galβ1,4(Fucα1,3)GlcNAc, Fucα1,2Galβ1,3GlcNAc, Galα1,3(Fucα1,2)Galβ1,3GlcNAc, Galα1,3(Fucα1,2)Galβ1,4GlcNAc, GalNAcα1,3(Fucα1,2)Galβ1,3GlcNAc, GalNAcα1,3(Fucα1,2)Galβ1,4GlcNAc, Fucα1,2Galβ1,4(Fucα1,3)GlcNAcβ1,3Gal, Gal(3SO$_4$)β1,4(Fucα1,3)GlcNAc, Gal(3SO$_4$)β1,3(Fucα1,4)GlcNAc, and Gal(3SO$_4$)β1,4(Fucα1,3)GlcNAc(6SO$_4$).

Among them, examples of particularly typical and useful fucosylated carbohydrate antigens include "Galβ1,4(Fucα1,3)GlcNAc: Lewis$^x$", "Galβ1,3(Fucα1,4GlcNAc: Lewis$^a$", "Fucα1,2Galβ13(Fucα1,4)GlcNAc: Lewis$^b$", "Fucα1,2Galβ1,4(Fucα1,3) GlcNAc: Lewis$^y$", "Fucα1,6GlcNAc", "GlcNAcβ1,4(Fucα1,6)GlcNAc", "Manβ1,4GlcNAcβ1,4 (Fucα1,6)GlcNAc", "Manα1,6(Manα1,3)Manβ1,4GlcNAcβ1,4 (Fucα1,6)GlcNAc", "Siaα2,3Galβ1,4(Fucα1,3)GlcNAc: Sialyl-Lewis$^x$", "Siaα2,3Galβ1,3 (Fucα1,4)GlcNAc: Sialyl-Lewis$^a$", "Siaα2,3Galβ1,3 (Fucα1,4) (Siaα2,6)GlcNAc: Disialyl-Lewis$^a$", "Siaα2,3Galβ1,4(Fucα1,3)GlcNAc(6SO$_4$): 6-sulfo-Sialyl-Lewis$^x$", "Siaα2,3Gal(6SO$_4$)β1,4(Fucα1,3)GlcNAc: 6'-sulfo-Sialyl-Lewis$^x$", "Siaα2,3Galβ1,4GlcNAcβ1,3Galβ1,4 (Fucα1,3) GlcNAc: VIM-2 antigen", and "Siaα2,3Galβ1,4(Fucα1,3)GlcNAcβ1,3Galβ1,4(Fucα1,3) GlcNAc: Sialyl-Lewis$^x$-i".

(1-4) Regarding Typical Oligosaccharide Antigens in the Present Invention

An immunity inducing method using the carrier compound of the present invention is a technique capable of attaining a monoclonal antibody which recognizes with specifically and high affinity not only to various complex carbohydrates that are biomarkers for diagnostic and pharmaceutical targets, but also to any newly discovered complex carbohydrate.

These optional oligosaccharide chains may be purified from a derived cell membrane fraction in a general method, and can also be synthesized by applying a known organic synthesis method or enzyme synthesis method if a sugar chain structure is found.

Here, in the embodiment of the present invention, when plural types of typical oligosaccharide antigens are selected from 3 types of oligosaccharide antigen groups contained in typical N-linked sugar chains, respectively, to apply the immunity inducing method of the present invention, it could be confirmed to cause antigen-specific immunity induction in a case of applying to any of the oligosaccharide antigens as an object. Specifically, the present invention was applied to the sugar chain structures of "6'-Sialyl-LacNAc(Siaα2,6Galβ1,4GlcNAc): CDw75", "3'-Sialyl-LacNAc(Siaα2,3Galβ1,4GlcNAc)" and "Sialyl-Lewis$^x$(Siaα2,3Galβ1,4(Fucα1,3)GlcNAc)" which are typical sialylated carbohydrate, "LacNAc(Galβ1,4GlcNAc)", "Lewis$^x$(Galβ1,4(Fucα1,3)GlcNAc)" which are typical asialo carbohydrates, and "Sialyl-Lewis$^x$(Siaα2,3Galβ1,4(Fucα1,3) GlcNAc)" and "Lewis$^x$(Galβ1,4(Fucα1,3)GlcNAc)" which are typical fucosylated carbohydrates as the objective oligosaccharide antigens (R) of the present invention. Accordingly, the immunity inducing method of the present invention can be applicable to general "oligosaccharide antigens contained in N-linked sugar chains". Furthermore, from the viewpoint that immunity can be enhanced also by oligosaccharide antigens contained in N-linked sugar chains", the present invention is also recognized as a technique applicable to any oligosaccharide antigen including other oligosaccharide antigens which are considered to facilitate immunity induction.

(1-4-1) Regarding Oligosaccharide "6'-Sialyl-LacNAc (Siaα2,6Galβ1,4GlcNAc)" (CDw75)

The sugar chain structure of a typical oligosaccharide antigen "CDw75" is expressed by the following general formula (3) of "6'-Sialyl-LacNAc(Siaα2,6Galβ1,4GlcNAc)" (CDw75).

[Chemical Formula 1]

General Formula (3)

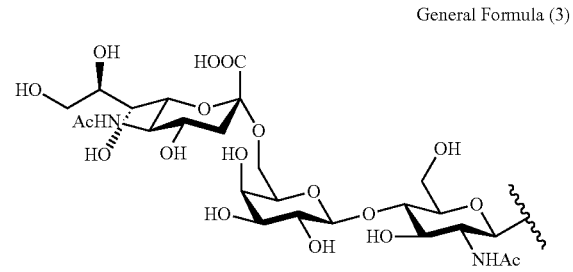

"CDw75" is a typical sialylated carbohydrate existing as a nonreducing end structure of an N-linked sugar chain produced by mammalian cells, and has been focused as a tumor marker (CDw75) to be a diagnostic index for determination of malignancy of gastric cancer and colon cancer and also as a molecular target for cancer treatments (Non Patent Literature 14). "CDw75" was reported as an infection receptor of human influenza virus (Non Patent Literature 15) and has been thus expected as a target for an influenza treatment.

While CDw75 (Siaα2,6Galβ1,4GlcNAc) is a carbohydrate antigen that is scarcely expressed in the normal human stomach and colon tissues, intensive expression is observed when these tissues turn cancerous, and application as a diagnostic marker for cancer is thus examined (Non Patent Literature 14).

On the other hand, CDw75 is recognized as the main N-linked sugar chain structure in a glycoprotein existing in a mammalian serum. Since CDw75 exists in the same way in a mouse body, immunity induction is hardly caused as compared to a microorganism derived carbohydrate and, in particular, production of an antibody which recognizes "a carbohydrate antigen contained in an N-linked sugar chain of a glycoprotein" is considered to be difficult.

(1-4-2) Regarding "3'-Sialyl-LacNAc (Siaα2,3Galβ1,4GlcNAc)"

The sugar chain structure of the typical oligosaccharide antigen, "3'-Sialyl-LacNAc (Siaα2,3Galβ1,4GlcNAc)" is expressed by the following general formula (4).

[Chemical Formula 2]

General Formula (4)

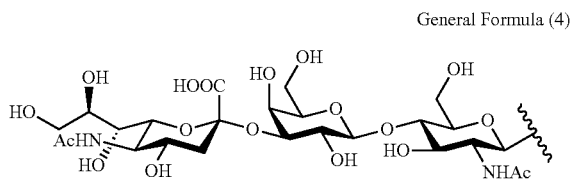

"3'-Sialyl-LacNAc" is also a typical sialylated carbohydrate existing as a nonreducing end structure of an N-linked protein produced by mammalian cells. Among influenza viruses, a type infected with birds (avian influenza virus) has been known to take this sugar chain structure as an infection receptor (Non Patent Literature 15).

(1-4-3) Regarding "LacNAc (Galβ1,4GlcNAc)"

The sugar chain structure of the oligosaccharide antigen, "LacNAc (Galβ1,4GlcNAc)" is expressed by the following general formula (5).

[Chemical Formula 3]

General Formula (5)

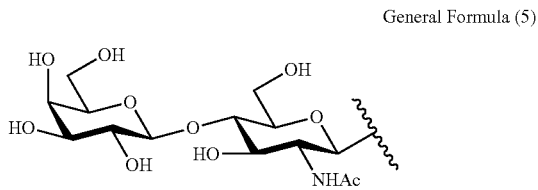

"LacNAc" is a typical asialo carbohydrate (non-sialylated carbohydrate) forming a nonreducing end structure and an internal structure of an N-linked protein, an O-linked sugar chain and an oligosaccharide chain, which are expressed in mammalian cells, in the same manner as "3'-Sialyl-LacNAc". "LacNAc" becomes a precursor structure of various sugar chain structures.

(1-4-4) Regarding "Sialyl-Lewis$^x$ (Siaα2,3Galβ1,4(Fucα1,3)GlcNAc)"

The sugar chain structure of the oligosaccharide antigen "Sialyl-Lewis$^x$ (Siaα2,3Galβ1,4(Fucα1,3)GlcNAc)" is expressed by the following general formula (6).

[Chemical Formula 4]

General Formula (6)

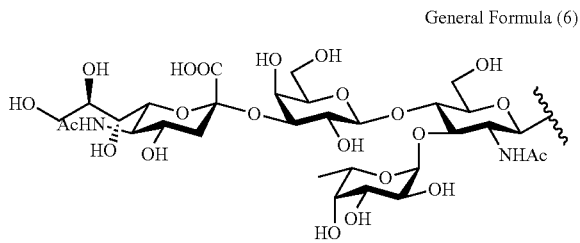

"Sialyl-Lewis$^x$ (Siaα2,3Galβ1,4(Fucα1,3)GlcNAc)" is a structure shown in an N-linked sugar chain or an O-linked sugar chain of a glycoprotein, which is produced by mammalian cells. This sugar chain is a ligand of an adhesive molecule protein (E-selectin) expressed in a site of inflammation (Non Patent Literature 16). Lymphocytes are recruited to a site of inflammation by cell adhesions through the interaction between Sialyl-Lewis$^x$ and E-selectin in a healthy subject. On the other hand, a part of metastatic cancer cells expresses Sialyl-Lewis$^x$, and this cell adhesion mechanism is utilized in metastasizing to another organ. Therefore, development of a therapeutic agent targeting Sialyl-Lewis$^x$ has been expected and Sialyl-Lewis$^x$ has been already used in diagnostic applications as a tumor marker for a breast cancer diagnosis (Patent Literature 4, Non Patent Literature 16). The carbohydrate antigen is a carbohydrate antigen contained in a glycoprotein which is expressed in a large amount specifically in a human promyelocytic leukemia cell line of a human leukemia cell (HL60) (Kobzdej M M., et al., Blood, 100, 4485-4494, 2002). A Sialyl-Lewis$^x$-containing glycoprotein can be easily prepared by HL60 cells.

(1-4-5) Regarding "Lewis$^x$ (Galβ1,4(Fucα1,3)GlcNAc)"

The sugar chain structure of the oligosaccharide antigen, "Lewis$^x$ (Galβ1,4(Fucα1,3)GlcNAc)" is expressed by the following general formula (7).

[Chemical Formula 5]

General Formula (7)

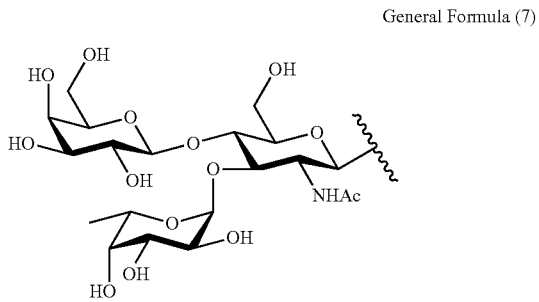

"Lewis$^x$ (Galβ1,4(Fucα1,3)GlcNAc)" is a carbohydrate antigen known as CD15 or SSEA-1 for another name. It is a structure shown in an N-linked sugar chain or an O-linked sugar chain in a glycoprotein such as α1-acid glycoprotein (AGP), which is produced by mammalian cells, and is a precursor of the above described Sialyl-Lewis$^x$. SSEA-1 is famous for an antigen generally used as a marker of stem cells/iPS cells in a mouse (Non Patent Literatures 17 and 18). Also as a tumor marker, SSEA-1 is expected to be used in applications as markers of bladder cancer and cancer stem cells (Non Patent Literatures 16 and 19).

2. Carrier Compound of the Present Invention

The carrier compound of the present invention is a novel lipid molecule expressed by the following general formula (1), which is similar to a lipid structure of α-galactosylceramide to be a bonding site with a CD1 molecule known for activation action of NKT cells. The carrier compound is in common with a lipid structure of a natural glycosphingolipid such as α-galactosylceramide in the point that one chain bonding to the carbonyl group side of a bonding structure "—CH(NH—CO)—" with a sugar is an unsubstituted saturated alkyl group; however, they can be definitely distinguished in the point that, while an alkyl group in the amino group side is a saturated alkyl group in the carrier compound of the present invention, an alkyl group bound to the amino group side is necessarily modified with a group containing oxygen such as an —OH group and an =O group in the case of a natural glycosphingolipid. What is more, in the case of a mammal-derived glycosphingolipid containing an oligosaccharide being a di- or polysaccharide, there is also a difference such as necessarily containing an unsaturated bond with an —OH group in an alkyl group bound to the amino group side. Therefore, the carrier compound of the present invention can be also regarded as "an artificial lipid or a salt thereof" similar to a natural lipid.

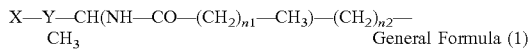
General Formula (1)

Here, in the formula, X represents —H, —OH, —SH, —NH$_2$, or a functional group capable of reacting with a reducing end hydroxyl group of a carbohydrate antigen, for example, halogen (—Br, —I, —Cl, —F), a hydrazide group, or the like.

Y represents a spacer sequence.

The spacer sequence Y in the present invention is expressed by "—(CH$_2$)$_m$—". m represents an integer from 1 to 30, preferably an integer from 1 to 10, and more preferably an integer from 1 to 3. A longer methylene chain is easily bound to a ligand (a receptor protein and an antibody on a lymphocyte) and an effect of increasing immunogenicity can be expected; however, a too long methylene chain causes low solubility to a polar solvent and has difficulty in handling and, therefore, a preferable numerical value range was set as a range for easy handling. A spacer sequence can also be introduced through a functional group X.

n1 represents an integer from 2 to 40, examples of a preferable embodiment include an integer from 14 to 39, 16 to 31, 17 to 28, and 20 to 40, examples of a more preferable embodiment includes an integer from 20 to 28 and 21 to 27, and the most preferable embodiment is an integer from 22 to 24. As the number of n1 is larger, that is, as a length of an alkyl chain in a fatty acid moiety becomes longer, immunity inducing ability tends to increase; however, an immunopotentiation effect can be obtained even when n1 is 2 to 10. In addition, a fatty acid having 22 or more carbon atoms (n1=20 or more) among long chain fatty acids is called a very long fatty acid, properties as a fatty acid are known to be different from properties of a general long chain fatty acid having a shorter length, and there is a difference in that cell membrane signal transmission is easily activated also in immune cells (Kihara A., J. Biochem., 152,387-395, 2012). The immunity inducing ability has been confirmed to be exceptionally enhanced in the case of a very long fatty acid having 22 or more carbon atoms (n1=20 or more) also in a fatty acid moiety in the carrier compound of the present invention. The upper limit is set within a preferable numerical value range in the present invention but is a preliminarily set numerical value from the viewpoints of easiness of synthesis and difficulty in handling, not from the viewpoint of immunity inducing ability. That is, since extremely high immunogenicity can be secured when n1 is 20 or more, a preferable numerical value range including a numerical value range for easiness of synthesis and handling is from 20 to 28 and from 21 to 27, and the most preferable numerical value range is from 22 to 24, as described above.

n2 represents an integer from 1 to 27, examples of a preferable embodiment include an integer from 2 to 15, 2 to 13, and 3 to 13, examples of a more preferable embodiment include an integer from 5 to 13 and 6 to 12, and the most preferable embodiment is an integer from 7 to 11. When n2 is less than 5, immunity inducing ability tends to decrease, and when n2 exceeds 9, although there are defects such that solubility to an aqueous solvent is reduced and synthesis efficiency by an enzyme method is lowered, immunity inducing ability has no problems.

In addition, the compound of the general formula (1) can be a pharmaceutically acceptable nontoxic salt. A salt of the compound of the general formula (1) may be an acid addition salt, and examples thereof include salts with inorganic acids (such as hydrochloric acid, sulfuric acid, nitric acid, and phosphoric acid), or salts with organic acids (such as acetic acid, propionic acid, maleic acid, oleic acid, palmitic acid, citric acid, succinic acid, tartaric acid, fumaric acid, glutamic acid, pantothenic acid, laurylsulfonic acid, methanesulfonic acid and phthalic acid). The carrier compound may be a solvate (for example, hydrate).

3. Immunity Inducer Containing Conjugate (Artificial Glycolipid) of Target Carbohydrate Antigen and Carrier Compound, and Production Method Thereof (3-1) Immunity Inducer of the Present Invention The conjugate of a target carbohydrate oligosaccharide antigen and a carrier compound of the present invention can be expressed by the following general formula (2).

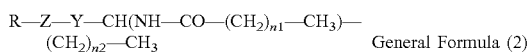
General Formula (2)

Here, in the formula, R is any oligosaccharide to be a carbohydrate antigen, and is a linear chain or branched molecule containing as a constitutional element one or plural types of monosaccharides selected from sialic acid (N-acetylneuraminic acid, N-glycolylneuraminic acid, α-ketodeoxynononic acid), galactose, glucose, N-acetylglucosamine, N-acetylgalactosamine, glucosamine, galactosamine, mannose, fucose, xylose, glucuronic acid, iduronic acid, inositol, erythrose, erythronic acid, erythruronic acid, erythraric acid, erythritol, threose, threonic acid, threuronic acid, threaric acid, threitol, ribose, ribonic acid, riburonic acid, ribaric acid, ribitol, arabinose, arabinonic acid, arabinuronic acid, arabinaric acid, arabinitol, xylose, xylonic acid, xyluronic acid, xylaric acid, xylitol, lyxose, lyxonic acid, lyxuronic acid, allose, allonic acid, alluronic acid, allaric acid, allitol, altrose, altronic acid, altruronic acid, altraric acid, altritol, gluconic acid, glucaric acid, glucitol, mannonic acid, mannuronic acid, mannaric acid, mannitol, gulose, gulonic acid, guluronic acid, idose, idonic acid, idaric acid, iditol, galactonic acid, galacturonic acid, galactaric acid, galactitol, talose, talonic acid, taluronic acid, altraric acid, altritol, dihydroxyacetone, erythrulose, ribulose, psicose, fructose, sorbose, tagatose, sedoheptulose, coriose, deoxyribose, rhamnose, fuculose, alomethylose, quinovose, antiarose, talomethylose, digitalose, digitoxose, cymarose, tyvelose, abequose, paratose, colitose, ascarylose, and sulfated, acetylated, phosphorylated or methylated sugars of these monosaccharides, preferably sialic acid, galactose, glucose, N-acetylglucosamine, N-acetylgalactosamine, glucosamine, galactosamin, mannose, fucose, xylose, glucuronic acid, iduronic acid, inositol, and sulfated, acetylated or methylated sugars of these monosaccharides, and the number of monosaccharides which constitute R is 2 to 30, preferably 2 to 16, and more preferably 2 to 6.

As described above in 1.(1), among these carbohydrate antigens, a mammalian cell-derived oligosaccharide antigen is mainly an object in the present invention and "an oligosaccharide antigen contained in an N-linked sugar chain" shown in glycoprotein of mammalian cells is particularly preferable. As a typical "oligosaccharide antigen contained in an N-linked sugar chain", examples of (a) sialylated carbohydrates include "Siaα2,6Galβ1,4GlcNAc: CDw75", "Siaα2,3Galβ1,4GlcNAc: 3'-Sialyl-LacNAc", "Siaα2,3Galβ1,4(Fucα1,3) GlcNAc: Sialyl-Lewis$^x$", "Siaα2, 3Galβ1,3(Fucα1,4)GlcNAc: Sialyl-Lewis$^a$", "Siaα2, 3Galβ1,3(Fucα1,4)(Siaα2,6)GlcNAc: Disialyl-Lewis$^a$", "Siaα2,3Galβ1,4(Fucα1,3)GlcNAc(6SO$_4$): 6-sulfo-Sialyl-Lewis$^x$", "Siaα2,3Gal(6SO$_4$)β1,4(Fucα1,3)GlcNAc: 6'-sulfo-Sialyl-Lewis$^x$", "Siaα2,3Galβ1,4GlcNAcβ1, 3Galβ1,4 (Fucα1,3)GlcNAc: VIM-2 antigen", "Siaα2, 6GalNAcβ1,4GlcNAc", "Siaα2,3Galβ1,4(Fucα1,3) GlcNAcβ1,3Galβ1,4 (Fucα1,3)GlcNAc: Sialyl-Lewis$^x$-i", and "Siaα2,3Galβ1,4GlcNAcβ1,3(Siaα2,3Galβ1, 4GlcNAcβ1,6)Gal: Sialyl-I"; examples of (b) asialo carbohydrates (non-sialylated carbohydrates) include "Galβ1, 4GlcNAc: LacNAc", "GlcNAcβ1,4Man", "GlcNAcβ1, 6Man", "Galβ1,4GlcNAcβ1,6Man", "GalNAcβ1, 4GlcNAc", "GalNAcβ1,4GlcNAcβ1,2Man", "GalNAc (4SO$_4$)β1,4GlcNAc", "Galβ1,4(Fucα1,3)GlcNAc: Lewis$^x$", "Galβ1,3(Fucα1,4)GlcNAc: Lewis$^a$", "Fucα1, 2Galβ1,3(Fucα1,4)GlcNAc: Lewis$^b$", "Fucα1,2Galβ1,4 (Fucα1,3GlcNAc: Lewis$^y$", "Fucα1,6GlcNAc", "GlcNAcβ1,4(Fucα1,6)GlcNAc", "Manβ1,4GlcNAcβ1,4 (Fucα1,6)GlcNAc", "Manα1,6(Manα1,3)Manβ1, 4GlcNAcβ1,4(Fucα1,6)GlcNAc", and "Galβ1,4GlcNAcβ1, 3(Galβ1,4GlcNAcβ1,6)Gal: I-antigen"; and examples of (c) fucosylated carbohydrate antigens include "Galβ1,4(Fucα1, 3)GlcNAc: Lewis$^x$", "Galβ1,3(Fucα1,4)GlcNAc: Lewis$^a$", "Fucα1,2Galβ1,3(Fucα1,4)GlcNAc: Lewis$^b$", "Fucα1, 2Galβ1,4 (Fucα1,3)GlcNAc: Lewis$^y$", "Fucα1,6GlcNAc", "GlcNAcβ1,4(Fucα1,6)GlcNAc", "Manβ1,4GlcNAcβ1,4 (Fucα1,6)GlcNAc", "Manα1,6(Manα1,3)Manβ1, 4GlcNAcβ1,4(Fucα1,6)GlcNAc", "Siaα2,3Galβ1,4(Fucα1, 3)GlcNAc: Sialyl-Lewis$^x$", "Siaα2,3Galβ1,4(Fucα1,3) GlcNAc: Sialyl-Lewis$^a$", "Siaα2,3Galβ1,3(Fucα1,4) (Siaα2,6)GlcNAc: Disialyl-Lewis$^a$", "Siaα2,3Galβ1,4 (Fucα1,3)GlcNAc(6SO$_4$): 6-sulfo-Sialyl-Lewis$^x$", "Siaα2, 3Gal(6SO$_4$)β1,4(Fucα1,3)GlcNAc: 6'-sulfo-Sialyl-Lewis$^x$", "Siaα2,3Galβ1,4GlcNAcβ1,3Galβ1,4(Fucα1,3) GlcNAc: VIM-2 antigen", and "Siaα2,3Galβ1,4(Fucα1,3) GlcNAcβ1,3Galβ1,4(Fucα1,3)GlcNAc: Sialyl-Lewis$^x$-i". In addition, effects of immunity induction are testified using typical (a) of "CDw75", "3'-Sialyl-LacNAc" and "Sialyl-Lewis$^x$", (b) of "LacNAc" and "Lewis$^x$", (c) of "Sialyl-Lewis$^x$" and "Lewis$^x$", respectively, among these three types of oligosaccharide antigens in examples of the present invention.

Z represents a single bond, or O, S or NH. When a carrier compound having an SH group or an NH$_2$ group as a functional group, a spacer, and a target carbohydrate are conjugated, Z is S or NH, and even when S or NH is contained in the carrier compound, immunity induction to a carbohydrate antigen is not affected (Non Patent Literatures 7 and 12). Z may be also a linker bound to thiomethyl or an aminomethylated sugar alcohol.

A linker bound to thiomethyl can be selected from commercially available linkers including BMPH (N-β-Maleimidopropionic acid hydrazide-TFA), KMUH (N-κ-Maleimidoundecanoic acid hydrazide-TFA), EMCH (N-[ε-Maleimidocaproic acid]hydrazide-TFA), MPBH (4-[4-N-Maleimidophenyl]butyric acid hydrazide-HCl) and PDPH (3-[2-Pyridyldithio]propionyl hydrazide) (manufactured by Thermo Fisher scientific Inc.). When such a commercially available linker is used, a large amount of polar groups are contained and such a linker is thus easily handled even though it has a long methylene chain.

As described below, as a method for producing a conjugate (artificial glycolipid) which functions as an immunity inducer to a target oligosaccharide antigen R by conjugating the carrier compound with the target oligosaccharide antigen R in the present invention, when a known reductive amination method is employed, a carbohydrate is cleaved to contain a sugar alcohol. A sugar alcohol in that case is preferably selected from sugar alcohols such as N-acetylglucosaminitol, N-acetylgalactosaminitol, mannitol and galactitol, and an aminomethylated sugar alcohol is preferably selected from N-acetylglucosaminitol, N-acetylgalactosaminitol, mannitol and galactitol.

Note that a sugar or a compound containing a sugar is not included in Z. A case of particularly containing a disaccharide or polysaccharide results in elongating a sugar chain in a target oligosaccharide antigen, and antigenicity of the target oligosaccharide antigen itself is damaged such that new antigenicity is imparted, thus being not preferable.

Y represents a spacer sequence and is defined as "—(CH$_2$)$_m$— (m represents an integer from 1 to 30, preferably an integer from 1 to 10, more preferably an integer from 1 to 3)" in the same manner as the case of the general formula (1). When a methylene chain is elongated, the linker is more easily bound to a ligand (a receptor protein or an antibody on a lymphocyte) and an effect of enhancing immunogenicity can be expected, a too long methylene chain results in low solubility to a polar solvent and difficulty in handling, and a preferable numerical value range was thus set as a manageable range. A spacer sequence can be also introduced through a functional group X. In this case, commercially available linkers can be used and examples thereof include BMPH (N-β-Maleimidopropionic acid hydrazide-TFA), KMUH (N-κ-Maleimidoundecanoic acid hydrazide-TFA), EMCH (N-[ε-Maleimidocaproic acid]hydrazide-TFA), MPBH (4-[4-N-Maleimidophenyl]butyric acid hydrazide-HCl), and PDPH (3-[2-Pyridyldithio]propionyl hydrazide) (manufactured by Thermo Fisher scientific Inc.). Since these linkers contain a large amount of polar groups, they are easily handed even with a long methylene chain.

n1 and n2 are also defined in the same manner as the general formula (1).

Specifically, n1 corresponding to an alkyl chain length in a fatty acid moiety is an integer from 2 to 40, examples of a preferable embodiment include an integer from 14 to 39, 16 to 31, 17 to 28 and 20 to 40, more preferable embodiments include an integer from 20 to 28 and 21 to 27, and the most preferable embodiment is an integer from 22 to 24. Here, as the number of n1 is larger, immunity inducing ability tends to increase, and when the number of n1 is 20 or more (in the case of a very long fatty acid having 22 or more carbon atoms), immunity inducing ability is exceptionally enhanced. On the other hand, the upper limit in the preferable numerical value range is a preliminarily set numerical value from the viewpoints of easiness of synthesis and difficulty in handling. That is, a case in which n1 is an integer from 20 to 40 is a preferable numerical value range of securing high immunogenicity, easiness of synthesis and easiness of handling, more preferable ranges are 20 to 28 and 21 to 27, and the most preferable range is 22 to 24.

n2 corresponding to an alkyl chain length in the amino acid side represents an integer from 1 to 27, examples of a preferable embodiment include an integer from 2 to 15, 2 to 13, and 3 to 13, examples of a more preferable embodiment include an integer from 5 to 13 and 6 to 12, and the most preferable embodiment is an integer from 7 to 11. When n2 is less than 5, immunity inducing ability tends to decrease, and when n2 exceeds 9, although there are defects such that solubility to an aqueous solvent is reduced and synthesis efficiency by an enzyme method is lowered, immunity inducing ability has no problems.

Here, among compounds included in the artificial glycolipid constituted with the above described general formula (2) or a salt thereof, which is used as the immunity inducer of the present invention, a compound in which R represents Siaα2,3GalβGlc, Z=O, Y=—(CH$_2$)—, and n1=16 and n2=9 is a known substance (Patent Literature 5) as a GM3 analog that is expected for an antitumor activity as an inhibitor of an epidermal growth factor receptor (EGFR). However, an artificial glycolipid in the case of a preferable embodiment of n1=20 to 40 in the immunity inducer of the present invention can be clearly distinguished from a GM3 analog in the case of n1=16, which cannot be regarded as a very long chain fatty acid, in the point of the immunity inducing ability.

That is, among an artificial glycolipid obtained by conjugating a target oligosaccharide antigen R and a carrier compound or a salt thereof, which is used as the immunity inducer of the present invention, the invention also relates to a novel artificial glycolipid expressed by the following general formula (2) or a salt thereof:

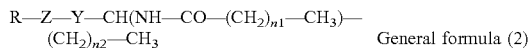

General formula (2)

(in the formula, R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —(CH$_2$)$_m$—, n1 represents an integer from 2 to 40, n2 represents an integer from 1 to 27, and m represents an integer from 1 to 30).

Z is preferably a single bond or O, S or NH, and may be a linker bound to thiomethyl or an aminomethylated sugar alcohol.

The linker bound to thiomethyl is preferably selected from commercially available linkers including BMPH (N-α-Maleimidopropionic acid hydrazide-TFA), KMUH (N-κ-Maleimidoundecanoic acid hydrazide-TFA), EMCH (N-[ε-Maleimidocaproic acid]hydrazide-TFA), MPBH (4-[4-N-Maleimidophenyl]butyric acid hydrazide-HCl), and PDPH (3-[2-Pyridyldithio]propionyl hydrazide) (manufactured by Thermo Fisher scientific Inc.), and the aminomethylated sugar alcohol is preferably selected from N-acetylglucosaminitol, N-acetylgalactosaminitol, mannitol and galactitol.

In addition, the compound of the general formula (2) can be a pharmaceutically acceptable nontoxic salt. A salt of the compound of the general formula (2) may be an acid addition salt, and examples thereof include salts with inorganic acids (such as hydrochloric acid, sulfuric acid, nitric acid, and phosphoric acid), or salts with organic acids (such as acetic acid, propionic acid, maleic acid, oleic acid, palmitic acid, citric acid, succinic acid, tartaric acid, fumaric acid, glutamic acid, pantothenic acid, laurylsulfonic acid, methanesulfonic acid and phthalic acid). The carrier compound may be a solvate (for example, hydrate).

Although a conjugate (artificial glycolipid) of the general formula (2) in the present invention has an action as an immunity inducer even solely, when immunization is actually carried out on an experimental animal, Lipid-A, LPS, *Salmonella minnesota* strain R595 treated with an acid, heat-killed bacteria, and the like, are preferably used in combination as adjuvants. Complete Freund's adjuvants (mixture of paraffin oil, Aracel A and heat-killed bacteria of tuberculosis bacteria), and the like, can also be used.

For immunization, favorably used is a liposome method of intravenously injecting liposome prepared by dissolving into a lipid such as cholesterol, phospholipid, diacylglycerol, monoacylglycerol, glycerol, fatty acid, glycocholic acid, taurocholic acid and a glycolipid without an adjuvant or with an adjuvant (method by Brodin, et al.; Eur J Immunol., 16, 951-956, 1986).

In addition, immunity inducing ability of the conjugate of the present invention is powerful and can be thus provided to in vitro immunization. In this case, although the conjugate of the general formula (2) may be dissolved solely into a cell culture liquid for lymphocyte culture to be acted on immune cells, the conjugate can be dissolved into a cell culture liquid at a high concentration by forming into liposome by the above described method by Brodin, et al., or a treatment such as adsorbing to a lipid-bound protein such as BSA. Therefore, the conjugate can be effectively acted on immune cells.

Accordingly, when referring to an immunity inducer in the present invention, the immunity inducer also include a compound of the general formula (2) itself, pharmaceutically acceptable nontoxic salts thereof, a composition with immunity inducing ability, which contains the compound of the general formula (2) as an effective component and further contains an adjuvant such as Lipid-A, and a liposome composition dissolved into a lipid.

(3-2) Production Method (3-2-1) Method of Bonding Carrier Compound (Artificial Lipid) to Oligosaccharide Antigen Directly or Through Spacer Sequence The carrier compound represented by the general formula (1) of the present invention can be directly bound to an oligosaccharide chain purified from a natural substance that is any target oligosaccharide chain or an oligosaccharide chain obtained through organic synthesis. As a method thereof, for example, a sugar donor obtained by protecting a hydroxyl group other than a reducing end in an oligosaccharide chain to introduce a leaving group (e.g., acetyl group, trichloroacetimidate group, hydroxyl group, thioalkyl group, and halogen) into the reducing end hydroxyl group is prepared and the sugar donor and the carrier compound of the general formula (1) are conjugated, or the prepared sugar donor and a part of the carrier compound of the general formula (1) are conjugated, thereafter elongating a sugar chain and constructing a carrier region by an enzyme reaction or a chemical reaction, and the carrier compound and the oligosaccharide can be thus conjugated with keeping the structure of the oligosaccharide chain.

According to the method, an oligosaccharide antigen can be bound to the carrier compound of the present invention even when the carbohydrate structure of the objective oligosaccharide antigen is not specified.

In addition, a method of protecting a hydroxyl group other than a reducing end in an oligosaccharide chain is described as follows.

(i) A protection process of reacting any oligosaccharide chain and a protecting reagent to protect a hydroxyl group other than a reducing end with a protecting group;

(ii) a substitution process of reacting the generated product in the above described process and a leaving group introduction reagent to substitute a hydroxyl group at the 1st position in the reducing end with a leaving group;

(iii) a process of reacting the generated product in the above described process and a reaction reagent in the presence of an activation agent to convert the reducing end; and (iv) a deprotection process of reacting the generated product in the above described process and a deprotecting reagent to deprotect a protecting group and obtaining a generated product having a converted reducing end in any oligosaccharide chain.

Here, as a protecting reagent used in the protection process, examples thereof include acetic anhydride/pyridine, and benzyl chloride/sodium hydroxide. As a leaving group introduction reagent used in the substitution process, examples thereof include anhydrous hydrobromic acid, alkylthiol (e.g., EtSH and PhSH)/lewis acid (e.g., TMSOTf and $BF_3$), acetic anhydride/pyridine and trichloroacetimidate. As an activating agent used in the conversion process, examples thereof include AgOTf when a leaving group is halogen, and MeOTf or lewis acid such as $BF_3$ when a leaving group is a thioalkyl group. As a reaction reagent used in the same process, examples thereof include 12-azidododecyl-1-ol, 3-azidopropyl-1-ol and p-methoxyphenol. As a deprotecting reagent used in the deprotection process, examples thereof include bases such as sodium methoxide and DBU for an acyl-based protecting group, and a contact reduction reaction in the presence of a metallic catalyst such as Pd and Pt and a Birch reduction reaction with sodium-ammonium for a benzyl protecting group.

(3-2-2) Method of Bonding Oligosaccharide Antigen to Carrier Compound (Artificial Lipid) Directly or Through Spacer Sequence <Production Method of Ceramide Analog>

(i) Synthesis Method of 2-Azidoalkyl Alcohol

A hydroxyl group at 1st position in alkyldiol (primary alcohol) is protected with a protecting reagent such as benzyl chloride and a side chain hydroxyl group (tertiary alcohol) is subsequently formed into a tosyl group by tosyl chloride, thereafter acting sodium azide to substitute the tosyl group with an azido group. When a fatty acid is continuously introduced, a reduction reaction of the side chain azido group is carried out and the fatty acid is condensed by an amidation reaction.

Examples of the fatty acid which can be used include butyric acid, valeric acid, hexanoic acid, heptanoic acid, octanoic acid, nonanoic acid, decanoic acid, undecanoic acid, dodecanoic acid, tridecanoic acid, myristic acid, pentadecanoic acid, palmitic acid, heptadecanoic acid, stearic acid, nonadecanoic acid, arachidic acid, heneicosanoic acid, behenic acid, tricosanoic acid, lignoceric acid, pentacosanoic acid, hexacosanoic acid, heptacosanoic acid, octacosanoic acid, nonacosanoic acid, melissic acid, henatriacontanoic acid, lacceroic acid, tritriacontanoic acid, tetratriacontanoic acid, pentatriacontanoic acid, hexatriacontanoic acid, heptariacontanoic acid, octatriacontanoic acid, nonatriacontanoic acid, tetracontanoic acid, hentetracontanoic acid, and dotetracontanoic acid.

Examples of alkyldiol which can be used include 1,2-pentanediol, 1,2-hexanediol, 1,2-heptanediol, 1,2-octanediol, 1,2-nonanediol, 1,2-decanediol, 1,2-undecanediol, 1,2-dodecandiol, 1,2-tridecanediol, 1,2-tetradecanediol, 1,2-pentadecanediol, and 1,2-hexadecanediol.

When a methylene chain with m=1 or more is introduced as Y (spacer sequence), 1,3-nonanediol, 1,4-heptanediol, or the like, can be used.

(ii) Introduction of Amino Group into X

A hydroxyl group at the 1st position is formed into a tosyl group by tosyl chloride, sodium azide is then acted to substitute the tosyl group with an azide group and the azide group is converted into an amino group by a reducing agent.

(iii) Introduction of Thiol Group into X

A hydroxyl group at the 1st position is substituted with a bromo group by phosphorus tribromide and reacted with hydrogen sulfide in the presence of alkali to thus introduce a thiol group.

(iv) Introduction of Hydrazide Group into X

An oxidant (such as potassium permanganate) is acted on a primary alcohol to convert into carboxylic acid, and thionyl chloride is subsequently acted to form into carboxylic acid chloride, thereafter acting hydrazine to thus convert into hydrazide.

(v) Introduction of Halogen into X

A halogenating agent (such as phosphorus tribromide, hydrogen iodide, thionyl chloride and DAST) is acted on a primary alcohol to form into a halogen.

<Introduction of Oligosaccharide Chain into Ceramide Analog>

(vi) When an amino group is contained in X, an oligosaccharide chain can be introduced by a reductive amination method. In this case, since a sugar in the reducing end cleaves, in order to keep a structure of a target oligosaccharide chain, an oligosaccharide containing an extra sugar to be a spacer is used, or hydroxylbenzaldehyde is bound to an oligosaccharide chain by the method described in Non Patent Literature 8 and then introduced.

(vii) When a thiol group is contained in X, an oligosaccharide chain can be introduced through a spacer having a functional group that reacts with a thiol group among the above described commercially available linkers.

(viii) When a hydrazide group is contained, an oligosaccharide chain can be introduced by reacting in a solvent such as PBS.

(viii) When a halogen group is contained, an oligosaccharide chain can be introduced by protecting a hydroxyl group other than the reducing end of the oligosaccharide chain and then reacting in a solvent.

(3-2-3) Method of Leading to Final Compound after Bonding Oligosaccharide Antigen and a Part of Carrier Compound First, a coupling reaction between only monosaccharide in the reducing end in an oligosaccharide chain structure and a 2-azidealkyl alcohol is carried out, then, a sugar chain is elongated in the nonreducing end of the monosaccharide by an enzyme reaction to synthesize a sugar chain structure to be the base of an objective oligosaccharide chain, thereafter condensing a fatty acid to a side chain amino group to thus produce a ceramide mimic glycolipid derivative.

Specifically, a method for producing a conjugate to be an effective component of the immunity inducer of the present invention, which contains the sugar chain structure "Siaα2, 6Galβ1,4GlcNAc (CDw75)" as a model, is described below.

After a sugar donor derived from N-acetyl-glucosamine (for example, 3,4,6-tri-O-acetyl-2-deoxy-2-(4,5-dichlorophthalimide)-D-glucopyranosyl bromide) and 2-azidealkyl alcohol $CH_3(CH_2)_{n2}CH(N_3)CH_2OH$ to be a receptor are coupled by a glycosylation reaction, a deprotection reaction of a hydroxyl group, a reducing reaction of a side chain azide group, and the like, are carried out to thus synthesize a glucosamine derivative having an amino group, GlcNAcβ1-$CH_2CH(NH_2)(CH_2)_{n2}CH_3$.

[Chemical Formula 6]

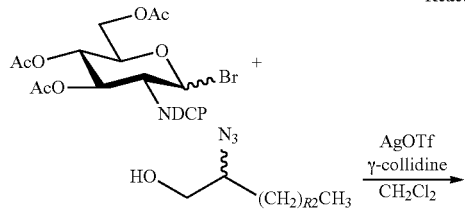

Reaction Formula (1)

-continued

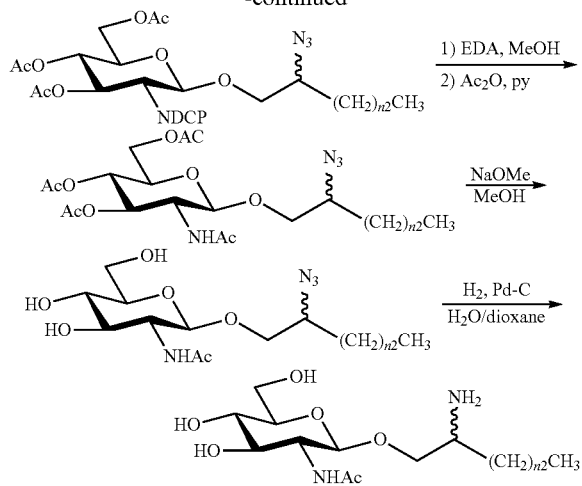

This glucosamine derivative intermediate is provided to an enzyme reaction using β1,4-galactosyltransferas and α2,6-sialyltransferase to elongate a sugar chain and converted into Siaα2,6Galβ1,4GlcNAcβ1-CH$_2$CH(NH$_2$)(CH$_2$)$_{n2}$CH$_3$.

Then, a side chain amide group in Siaα2,6Galβ1,4GlcNAcβ1-CH$_2$CH(NH$_2$)(CH$_2$)$_{n2}$CH$_3$ and a fatty acid are condensed by an amidation reaction to thus synthesize Siaα2,6Galβ1,4GlcNAcβ1-CH$_2$CH(NH—CO—(CH$_2$)$_{n1}$—CH$_3$)—(CH$_2$)$_{n2}$—CH$_3$.

[Chemical Formula 7]

Reaction Formula (3)

[Chemical Formula 8]

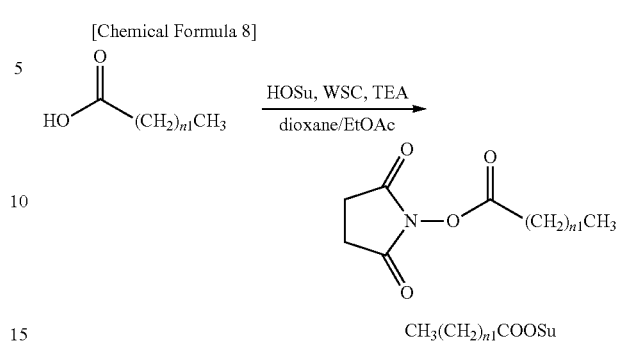

CH$_3$(CH$_2$)$_{n1}$COOSu

4. Immunization Method (4-1) Immunization Method

A known general method in this field can be applied for the method for producing a monoclonal antibody of the present invention (for example, Shepherd P. and Dean C., Monoclonal Antibodies, Oxford University Press, 2000). Specifically, a nonhuman mammal, for example, a rat, a mouse and a rabbit, preferably a mouse, is immunized using a conjugate (the general formula (2)) bound to a carrier compound (the general formula (1)) that is developed by the present inventors to a target oligosaccharide chain in a general method.

For immunization, favorably used is a liposome method of abdominally and intravenously injecting liposome pre- Reaction Formula (2)

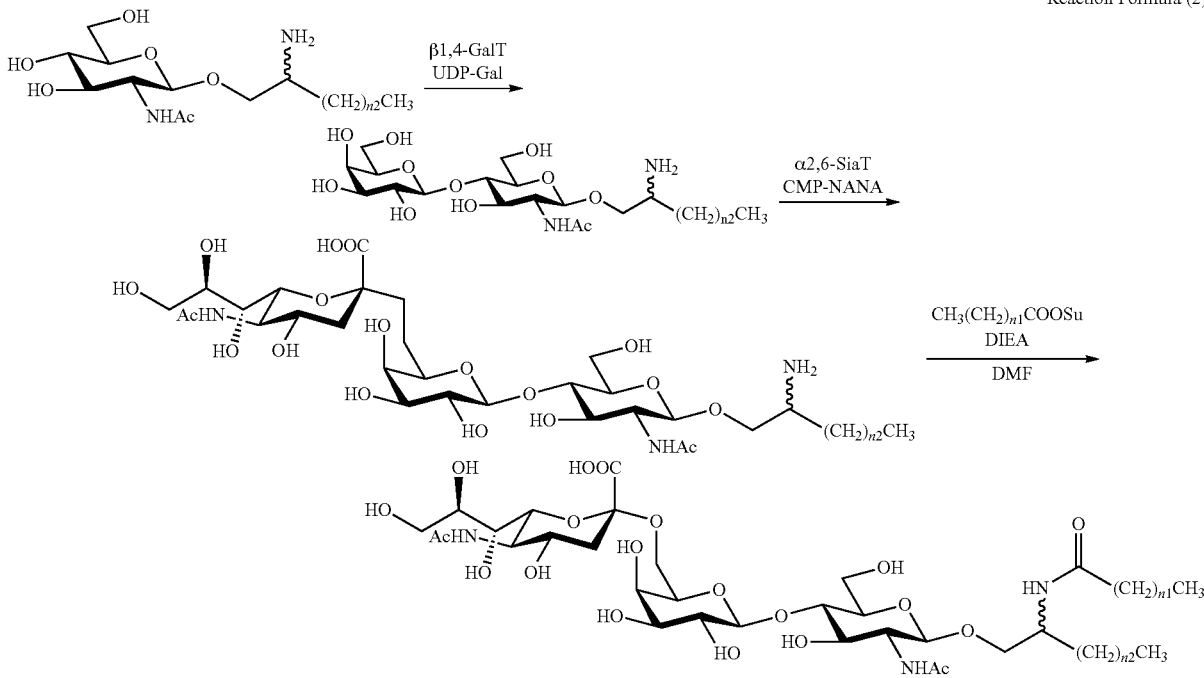

The fatty acid is condensed using N-hydroxysuccinimide and 1-ethyl-3-(3-dimethylaminopropyl)carbodiimide hydrochloride to convert into a succinimide ester and isolated. This fatty acid active ester product and alkyl glycoside are supplied to coupling.

pared by dissolving into a lipid such as cholesterol and phospholipid with an adjuvant (Lipid-A) (method by Brodin et al.; Eur. J. Immunol., 16, 951-956, 1986), and the like. Other than the above method, a method of adsorbing the conjugate (general formula (2)) to a *Salmonella minnesota* strain R595 treated with an acid and abdominally and intravenously injecting the conjugate (method by Galanos et al.; Eur. J. Biochem., 24, 116-122,1971) may be also used.

An administration amount of a fused carbohydrate antigen per one animal is from 0.05 to 0.2 mg under a use of an adjuvant. As the adjuvant, a *Salmonella minnesota* strain R595 treated with an acid, a complete Freund's adjuvant, and the like, can be used, but a liposome method containing Lipid-A is preferable. During administration, additional immunization can be also conducted. Immunization is carried out mainly by intravenous, subcutaneous and abdominal injections. In addition, an interval of immunization is not particularly limited, and immunization is conducted 1 to 10 times, preferably 2 to 5 times at intervals from several days to several weeks, preferably intervals from 2 to 5 weeks. Antibody producing cells are then collected after 1 to 60 days, preferably after 1 to 14 days from the final immunization day. Examples of the antibody producing cells include spleen cells, lymph node cells, and peripheral blood cells, and spleen cells or local lymph node cells are preferable.

(4-2) Selection Method of Hybridoma

By a general method, spleen cells are fused with myeloma cells and incubated with thymus feeder cells in a medium in the presence of IL-6, and a hybridoma is selected by HAT in an IMDM medium. A supernatant of grown clones is then screened using a target oligosaccharide chain. During screening, an immune tissue chemical analysis, or the like, may be employed, and a simple screening method by an enzyme immunoassay (such as ELISA) or western blot can be applied to the target oligosaccharide chain fixed to a substrate. Here, it is also a merit of the present invention that ELISA or a western blot method can be applied for selection of a target oligosaccharide chain antibody producing hybridoma.

In the present invention, an antibody titer of a culture supernatant is preferably evaluated by ELISA, and a hybridoma is selected using the antibody titer as an index. The antibody titer is evaluated as an activity of peroxidase that is a labeling enzyme of an anti-mouse immunoglobulin antibody used as a secondary antibody, for example. TMB is used as a chromogenic substrate of peroxidase, and an intensity of an absorbance at 450 nm after adding 2N-sulfuric acid after the reaction was evaluated.

First, a monoclonal antibody producing hybridoma cell recognizing a glycoprotein containing a glycolipid antigen to be an immunogen and a target oligosaccharide chain structure is selected, and a monoclonal antibody producing hybridoma having no reactivity to a sugar chain structure similar to the target sugar chain structure is then selected.

5. Test Method of Characteristics of Monoclonal Antibody Recognizing Target Oligosaccharide Chain of the Present Invention (5-1) Specificity Test

<ELISA>

Together with a protein (or lipid) having the target oligosaccharide antigen of the present invention, a protein (or lipid) having a similar oligosaccharide chain is immobilized to a substrate (ELISA plate) by evaporation and drying, and specificity is evaluated by ELISA method as an antibody titer (intensity of absorbance at 450 nm).

A commercially available sugar chain array may also be used.

<Western Blot Analysis>

A sample is separated by SDS-polyacrylamide gel electrophoresis, and electrically transcribed into a membrane such as PVDF using a blotting apparatus. The membrane after transcription is blocked with 1% skim milk-PBST, or the like, a primary antibody obtained by appropriately diluting with PBST permeates the membrane to be reacted.

After reacting at room temperature for 1 to 3 hours, the membrane is washed by shaking with a washing buffer such as PBST and a HRP labeling secondary antibody is reacted. After washing with PBST, a chemiluminescence substrate is reacted to detect an antibody reaction by an image analyzer.

<Sugar Chain Array Method>

An antibody obtained by appropriately diluting with PBST, or the like, is dropped into a "sugar chain array" in which a sugar chain is immobilized onto a substrate.

The antibody solution permeates the substrate surface by covering with a cover glass, or the like, and is incubated at room temperature for about 2 hours. After gently stirring and washing with PBST, or the like, a fluorescent labeling secondary antibody is reacted. A slide is dried after washing, and fluorescence on the slide is then detected using a scanner for a microarray.

<Competitive Inhibition Assay>

In the above decried ELISA, an oligosaccharide chain to be an antagonist is previously incubated with an antibody, and an antibody titer is then evaluated. By changing an amount of an adding antagonist, a concentration at which the antagonist inhibits an antigen antibody reaction is evaluated.

<Cell Fluorescent Staining Method>

A cell expressing a target oligosaccharide antigen is incubated with an antibody, and an antibody reaction is then labeled by a fluorescent labeling secondary antibody and detected by a fluorescence detection apparatus.

(5-2) Affinity

Figure 6:
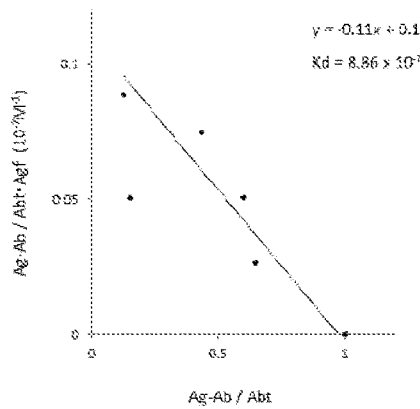
FIG. 6 illustrates affinity to an epitope of the developed monoclonal antibody FR9: A: As affinity to an epitope of the FR9 antibody, a dissociation constant (Kd value) using a glycoprotein (Fetuin) containing a CDw75 sugar chain was determined by ELISA method and scatchard plot. A value (Ag-Ab/Abt) obtained by dividing an amount of an antigen-antibody complex (Ag-Ab) by the total antibody amount (Abt) is plotted in the x axis, and a value (Ag-Ab/Abt•Agf) obtained by dividing (Ag-Ab/Abt) by the total free antigen amount (Agf) was plotted in the y axis. Since a gradient of an approximated curve of each plot ($y=-0.11x+0.11$) was −1/Kd, a Kd value (8.86×10$^{-7}$ M) was calculated from the gradient value. B: As affinity to an epitope of the FR9 antibody, detection sensitivities were measured using a glycoprotein containing CDw75 (Fetuin: white circle) and an immunogen (CDw75-C12L) as antigens by ELISA.
Figure 6:
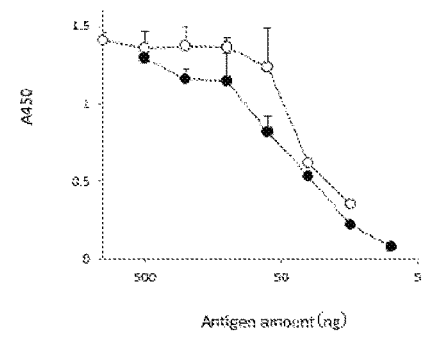

Affinity of an antibody to a target carbohydrate is determined in a calculation method by ELISA method (Friguet B., et al., J. Immunol. Methods, 77, 305-319, 1985). An antibody is prepared by diluting with PBS to have a concentration of $1 \times 10^{-7}$ M, or the like, and blended and incubated with an antigen that is processwisely diluted to have a concentration of 25 to $1.56 \times 10^{-7}$ M to thus form an antigen antibody complex product. A free antibody amount in this blended solution is calculated by ELISA using an antigen solid-phased plate and a Kd value (dissociation constant) was determined from the obtained value by a Scatchard plot (FIG. 6A). In addition, by ELISA method using a plate obtained by stepwisely diluting Fetuin and CDw75-C12L to form into a solid phase, how much level of an antigen amount the prepared antibody can detect is measured (FIG. 6B).

(5-3) Antibody Titer

Each immunogen was subcutaneously immunized on the first day, and additional immunization was abdominally conducted after two weeks. The blood was collected after 3 days and 7 days from the additional immunization to prepare serums. Antibody titers in the obtained serums were evaluated by ELISA. An immunogen and a glycoprotein containing an objective carbohydrate were used as solid-phased antigens by ELISA, and each was evaluated as an antibody titer to the immunogen and an antibody titer to the objective carbohydrate (FIGS. 1 to 4).

Figure 2:
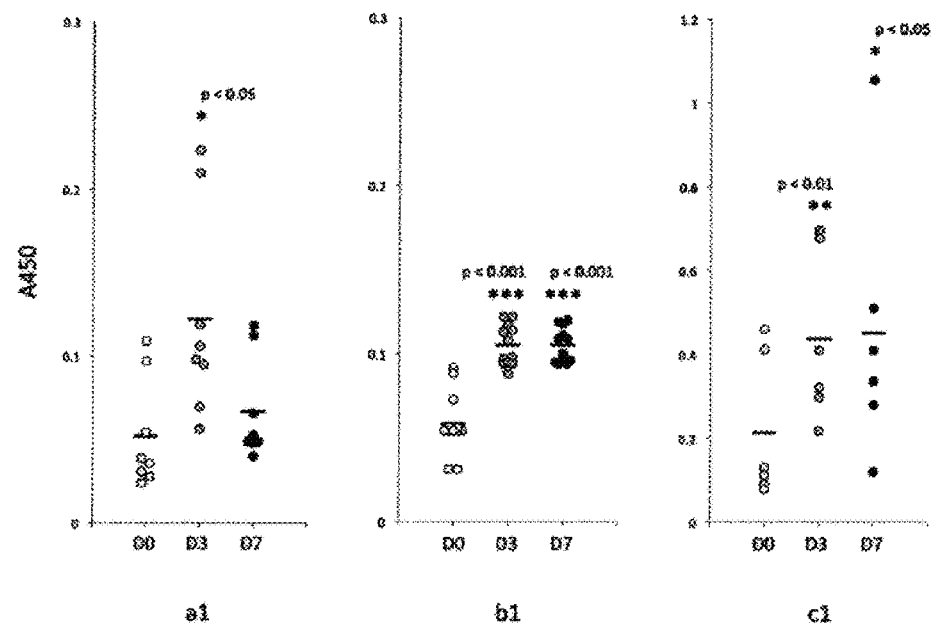
FIG. 2 illustrates serum antibody titers to a glycoprotein after immunity induction: a serum antibody titer to a glycoprotein (Fetuin) as an antigen having the same oligosaccharide chain structure as an immunogen after immunizing a mouse using each of compounds a1, b1 and c1 as an immunity inducer was measured by ELISA. In c1, Fetuin-a (Table 1) obtained by removing sialic acids in all bonding types by a sialidase treatment was used as an antigen. White circles denote antibody titers in unimmunized mouse serums (D0), gray circles denote antibody titers in mouse serums after 3 days from the final immunization (D3), black circles denote antibody titers in mouse serums after 7 days from the final immunization (D7); and the antibody titers in mouse serums were individually plotted in the graphs (n=6 to 12). It was confirmed that, as compared to the serum antibody titers in unimmunized mice, each of the serum antibody titers of D3 and D7 significantly increased by a Student's t test. ($*p<0.05$, $p<0.01$, $*p<0.001$)
Figure 3:
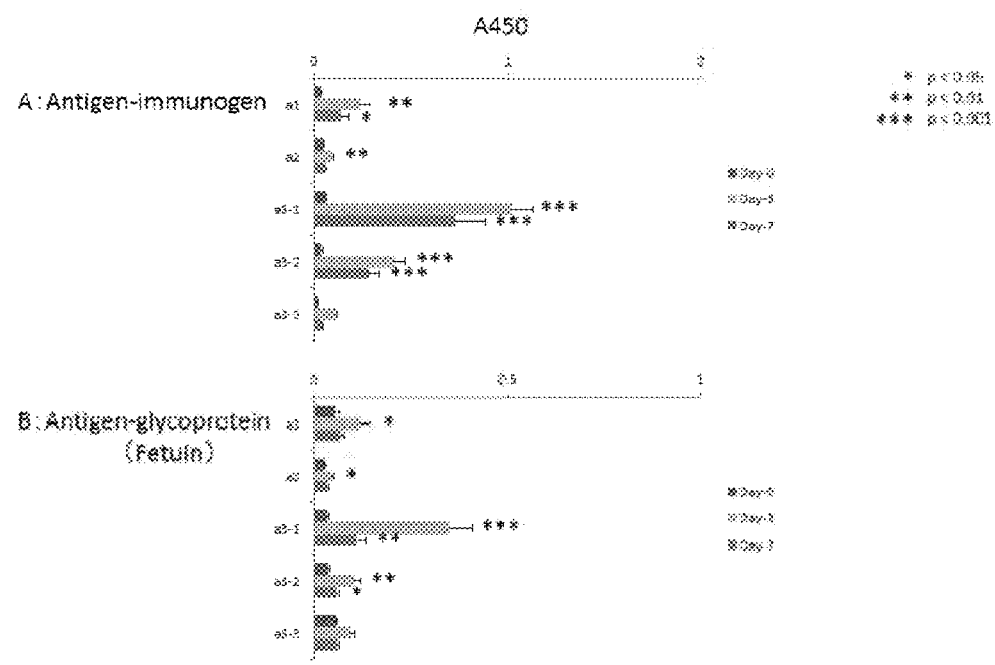
FIG. 3 illustrates serum antibody titers after immunity induction (IgM subclass): an antibody titer of immunoglobulin (IgM subclass) in a serum to a target sugar chain epitope after immunizing a mouse using each of compounds a1 to a3-3 as an immunity inducer was evaluated by ELISA. A: Evaluation using an immunogen as an antigen by ELISA. B: Evaluation using a glycoprotein (Fetuin) containing a target sugar chain epitope as an antigen by ELISA. Regarding Day-0, serum antibody titers before immunization; Day-3, serum antibody titers after 3 days from the final immunization; and Day-7, serum antibody titers after 7 days from the final immunization, respective antibody titers in mouse serums were shown in graphs. It was confirmed that, as compared to the serum antibody titers in unimmunized mice, each of the serum antibody titers of D3 and D7 significantly increased by a Student's t test. ($*p<0.05$, $p<0.01$, $*p<0.001$, n=5-10)
Figure 4:
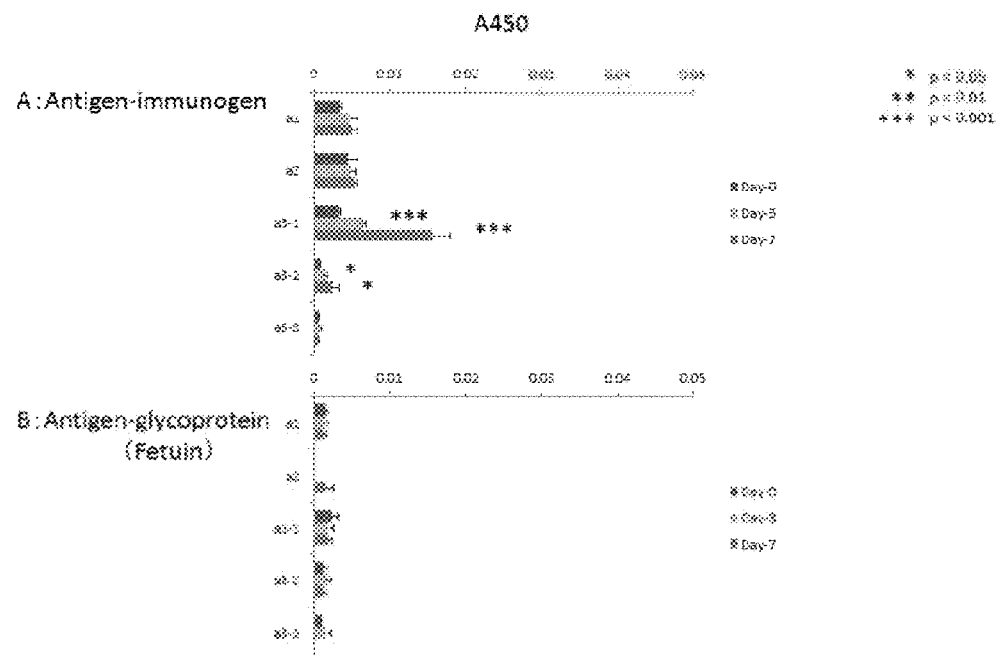
FIG. 4 illustrates serum antibody titers after immunity induction (IgG subclass): an antibody titer of immunoglobulin (IgG subclass) in a serum to a target sugar chain epitope after immunizing a mouse using each of compounds a1 to a3-3 as an immunity inducer was evaluated by ELISA. A: Evaluation using an immunogen as an antigen by ELISA. B: Evaluation using a glycoprotein (Fetuin) containing a target sugar chain epitope as an antigen by ELISA. Regarding Day-0, serum antibody titers before immunization; Day-3, serum antibody titers after 3 days from the final immunization; and Day-7, serum antibody titers after 7 days from the final immunization, respective antibody titers in mouse serums were shown in graphs. Insufficient class switching to IgG was presumed because of only primary additional immunization; however, it was confirmed that, as compared to the serum antibody titers in unimmunized mice, when an immunogen was used as an antigen, each of the serum antibody titers of D3 and D7 significantly increased by a Student's t test. ($*p<0.05$, $p<0.01$, $*p<0.001$, n=5-10)

In order to evaluate subclasses (IgM and IgG) of produced immunoglobulin, evaluation was conducted using antibodies specific to IgM and IgG as secondary antibodies. An antibody titer was evaluated as an activity of peroxidase that is a labeling enzyme of a secondary antibody. TMB was used as a chromogenic substrate of peroxidase, and an intensity of an absorbance at 450 nm after adding 2 N-sulfuric acid after the reaction was evaluated. FIGS. 1 to 3 illustrate antibody titers of IgM subclass, and FIG. 4 illustrates antibody titers of IgG subclass.

(5-4) Rhymus-dependent Antigen Activity

An increase of the antibody titer of the IgG class antibody to an antigen was evaluated as an index of an immunogen (immunity inducer of the present invention) rhymus-dependent activity in the above described (5-3).

6. Pharmaceutical Composition or Vaccine for Immunopotentiation Containing Immunity Inducer of the Present Invention A compound expressed by the general formula (2) to be the immunity inducer of the present invention or a salt thereof can be used as an effective component of a pharmaceutical composition for immunopotentiation, which can cause an effect of enhancing a target carbohydrate antigen-specific IgG antibody producing ability in a patient's body suffering from various malignant tumors and malignant diseases without an adjuvant, or with an adjuvant such as aluminum phosphate, aluminum chloride, aluminum salt, aluminum hydroxide, aluminum sulfide, Montanide ISA51, Montanide ISA720VG, MF59, and AS03, or in a state of a liposome prepared by dissolving into a lipid such as cholesterol, phospholipid, diacylglycerol, monoacylglycerol, glycerol, fatty acid, glycocholic acid, taurocholic acid and a glycolipid. A subject is mainly a human but is not limited to a human, and in addition to mammals including pet animals such as dog, monkey, cat and rabbit, domestic animals such as cow, horse and pig, experimental animals such as mouse and rat, the compound can be previously administered into birds as a vaccine for avian influenza that has a possibility to infect a human.

For example, in the case of a conjugate compound to a "Siaα2,6Galβ1,4GlcNAc (CDw75)" antigen, the compound can be used as an effective component of a pharmaceutical composition for a malignant tumor treatment or a pharmaceutical composition for prevention or treatment of influenza, and in the case of a conjugate compound to a "Siaα2,3Galβ1,4GlcNAc" antigen, the compound can be used as an effective component of a pharmaceutical composition for prevention or treatment of avian influenza.

The compound expressed by the general formula (2) or a salt thereof can be prescribed into an appropriate dosage form which is determined by a treatment method, an administration method and an administration purpose, specifically, formulations such as an injection, a suspending agent, an emulsifier, an ointment, cream, a tablet, a capsule, a granule, powder, a pill, a fine granule, a troche tablet, a rectal administration agent, an oleagenous suppository, and a water-soluble suppository.

These various formulations can be manufactured in a general method using a pharmaceutically acceptable carrier, and the like. Specifically, the following vehicles can be used: a solvent (e.g., water and physiological saline), and an extender and a filler (e.g., lactose, starch, crystalline cellulose, mannitol, maltose, calcium hydrogen phosphate, soft silicic anhydride and calcium carbonate); and the following auxiliary agents can be used: a solubilizer (e.g., ethanol and polysorbate agent), a binder (e.g., starch, polyvinylpyrrolidone, hydroxypropyl cellulose, ethyl cellulose, carboxymethyl cellulose and Gum arabic), a disintegrating agent (e.g., starch and carboxymethyl cellulose), a lubricant (e.g., magnesium stearate, talc and hydrogenated oil), a stabilizer (e.g., lactose, mannitol, maltose, polysorbates, macrogols and polyoxyethylene hydrogenated castor oil), a tonicity agent, a wetting agent, a lubricant agent, a dispersing agent, a buffer, and a solubilizing agent. According to necessity, an antioxidant, a preservative, a flavoring agent, a soothing agent, a stabilizer, a coloring agent, a sweetening agent, and the like, are contained as additives.

In addition, glycerin, dimethylacetoamide, 70% sodium lactate, surfactants, and basic substances (for example, ethylene diamine, ethanolamine, sodium carbonate, arginine, meglumine and trisaminomethane) can be also added to various formulations, if necessary.

In the present invention, the compound expressed by the general formula (2) or a salt thereof can be administered by an administration route such as intravenous administration, local administration by an injection, subcutaneous administration, intramuscular administration, sublingual administration, percutaneous absorption or intrarectal administration. Intravenous administration is the most preferable.

Each effective component in a therapeutic agent in the present invention can be continuously or intermittently administered according to an individual situation. A specific administration amount is changed due to, in addition to an objective disease and its severity, administration methods, various conditions of a patient, for example, age, weight, sex, sensitivity, administration time, and concomitant drugs. In general, an administration amount of the compound expressed by the general formula (2) is, for example, about 0.001 to 10 mg, preferably 0.01 to 1 mg to an adult human per one day in intravenous administration. The compound of the general formula (2) is preferably prescribed into a freeze-dried formulation, and freeze-dried formulation is preferably administered to a patient by dissolving into distilled water for injection right before administration.

An animal such as a mouse is immunized with the immunity inducer of the present invention to produce a target carbohydrate antigen-specific antiserum or monoclonal antibody, and the target carbohydrate antigen-specific antiserum or monoclonal antibody can be used as an effective component of a pharmaceutical composition for prevention or treatment of various diseases.

EXAMPLES

Hereinbelow, the present invention will be specifically explained in view of examples, and the present invention is however not limited thereto.

Other terms and concepts in the present invention are based on meanings of terms idiomatically used in the field, and various techniques used for implementation of the present invention can be easily and surely carried out based on known documents by a person skilled in the art except for techniques whose sources are particularly specified. In addition, various analyses were conducted in accordance with methods described in instruction manuals, catalogues, and the like, of used analytical instruments, agents and kits.

Note that contents described in technical documents, patent literatures and specifications of patent applications cited in the present specification are referred as the content described in the present invention.

<Structure of Carbohydrate Antigen Used in Evaluation of Serum Antibody Titer>

A carbohydrate structure of a compound used in the evaluation of a serum antibody titer by ELISA is shown in the following (Table 1).

In the table, each of a1, b1 and c1 is a sphingo sugar ceramide derivative that is a conjugate of oligosaccharide antigens respectively expressed by the general formula (3), (4) and (5), and a ceramide analog (CerA).

CerA shows a ceramide analog (HOCH$_2$CH(NH—CO—(CH$_2$)$_{16}$—CH$_3$)—(CH$_2$)$_9$—CH$_3$) that is a typical example of the carrier compound of the present invention, and is obtained by bonding to a reducing end of each carbohydrate though a hydroxyl group. Cer is a ceramide (natural substance), and each of LacCer, GM3, GM1, GD1a and Globoside is a glycolipid being a natural substance obtained by bonding a carbohydrate to ceramide. R shows a basic structure of Fetuin (Fetuin carbohydrate constituting the reducing side of a carbohydrate structure shown in the table and the core protein part). Each of Fetuin-a and Fetuin-b was prepared by selectively decomposing the carbohydrate structure of Fetuin with sialidase or α2,3-sialidase.

X—Y—CH(NH—CO—(CH$_2$)$_{n1}$—CH$_3$)—(CH$_2$)$_{n2}$—CH$_3$
(in the case of Y=—CH$_2$—) to "6'-Sialyl-LacNAc (CDw75)" which is one of sialylated carbohydrates expressed in mammalian cells and is focused as a tumor marker (CDw75) that is a diagnostic index for determination of malignancy of stomach cancer and colon cancer and also as a molecular target for a treatment of malignant tumor.

Production of Compound a1 (in the Case of n1=16 and n2=9 in the General Formula 1)

[Chemical Formula 9]

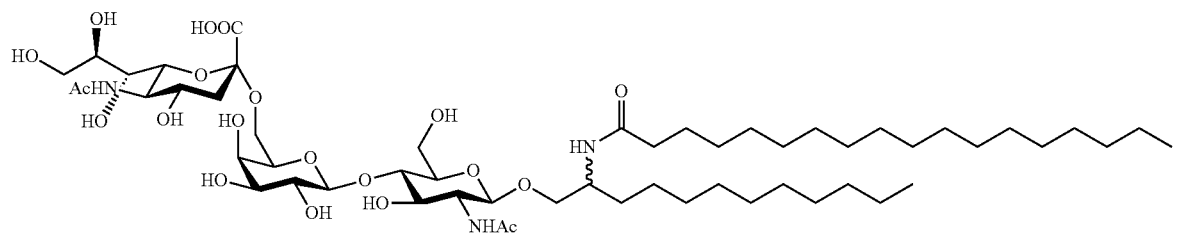

a1

In Table 1, HL60 indicates a glycoprotein fraction extracted from HL60 cells, and the main carbohydrate structure was shown in Table 1. The basic structure was expressed by R2. The main carbohydrate structure of glycoprotein AGP was also shown and the basic structure was expressed by R3. The main carbohydrate structure contained in HL60 is Siaα2,3Galβ1,4(Fucα1,3)GlcNAc (Sialyl-Lewis$^X$), and the main carbohydrate structures contained in AGP are Siaα2,6Galβ1,4GlcNAc (CDw75) and Galβ1,4(Fucα1,3)GlcNAc (Lewis$^X$).

TABLE 1

| Antigen | Structure |
|---|---|
| a1 | Siaα2,6Galβ1,4GlcNAcβ1-CerA |
| b1 | Siaα2,3-Galβ1,4GlcNAcβ1-CerA |
| c1 | Galβ1,4GlcNAcβ1-CerA |
| sLeX-C12L | Siaα2,3Galβ1,4(Fucα1,3)GlcNAcβ1-C12L |
| LeX-C12L | Galβ1,4(Fucα1,3)GlcNAcβ1-C12L |
| LacCer | Galβ1,4Glcβ1-Cer |
| GM3 | Siaα2,3Galβ1,4Glcβ1-Cer |
| GM1 | Galβ1,3GalNAcβ1,4(Siaα2,3)Galβ1,4Glcβ1-Cer |
| GD1a | Siaα2,3Galβ1,3GalNAcβ1,4(Siaα2,3)Galβ1,4Glcβ1-Cer |
| Fetuin | Siaα2,6(3)Galβ1,4GlcNAcβ1-R |
|  | Siaα2,3Galβ1,3GalNAcα1-R |
|  | Siaα2,3Galβ1,3(Siaα2,6)GalNAcα1-R |
| Fetuin-a | Galβ1,4GlcNAcβ1-R |
|  | Galβ1,3GalNAcα1-R |
| Fetuin-b | Siaα2,6Galβ1,4GlcNAcβ1-R |
|  | Galβ1,4GlcNAcβ1-R |
|  | Siaα2,3Galβ1,3GalNAcα1-R |
|  | Siaα2,3Galβ1,3(Siaα2,6)GalNAcα1-R |
| HL60 | Siaα2,3Galβ1,4(Fucα1,3)GlcNAcβ1-R2 |
| AGP | Galβ1,4(Fucα1,3)GlcNAcβ1-R3 |
|  | Siaα2,6(3)Galβ1,4GlcNAcβ1-R3 |
| Globoside | GalNAcβ1,3Galα1,4Galβ1,4Glcβ1-Cer |

Example 1

Production of Immunity Inducer of Present Invention (1-1) Production of Immunity Inducer Having Carbohydrate Structure of "6'-Sialyl-LacNAc (CDw75)"

As a target oligosaccharide chain of the present invention, produced is a conjugate (immunity inducer) obtained by fusing the carrier compound of the present invention, The compound a1 was synthesized according to the following reaction formula (4). Specifically, a sugar donor derived from N-acetyl-glucosamine (for example, 3,4,6-tri-O-acetyl-2-deoxy-2-(4,5-dichlorophthalimide)-D-glucopyranosyl bromide (Shimizu H., et al., Biosci. Biotech. Biochem., 60, 73-76, 1996) is synthesized) and 2-azidododecanol, CH$_3$(CH$_2$)$_9$CH(N$_3$)CH$_2$OH to be a receptor were coupled by a glycosylation reaction, and a deprotection reaction of a hydroxy group, a reduction reaction of a side chain azide group, and the like, were then carried out to synthesize a glucosamine derivative having an amino group, GlcNAc-CH$_2$CH(NH$_2$)(CH$_2$)$_9$CH$_3$. Although this intermediate was a racemic form since it had asymmetric carbon in the root of an amino group, the intermediate can be separated by purification by high performance liquid chromatography (HPLC) in this stage, and the synthesis was therefore carried out dividing into (S) form and (R) form hereinafter.

[Chemical Formula 10]

Reaction Formula (4)

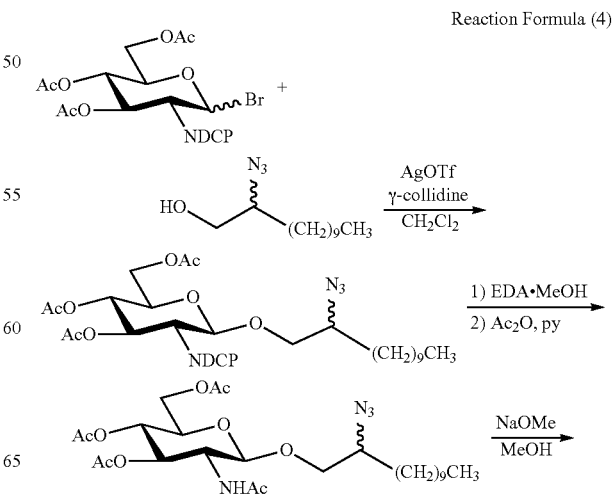

-continued

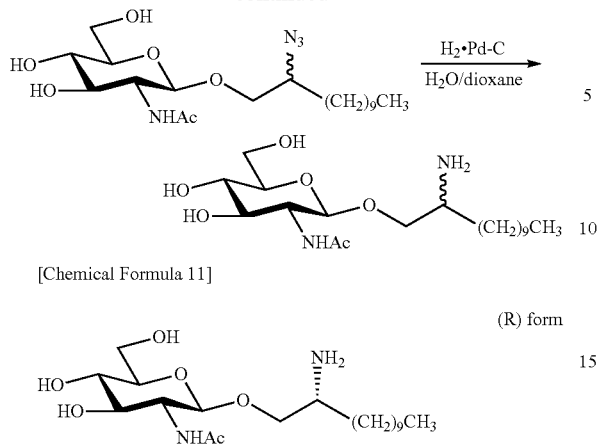

[Chemical Formula 11]

-continued

[Chemical Formula 12]

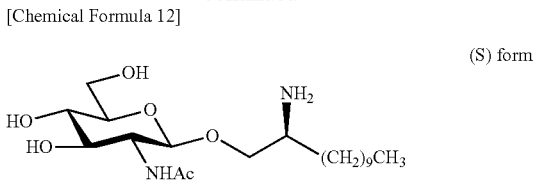

The obtained intermediate compound was supplied to an enzyme reaction using β1,4-galactosyltransferase according to the following reaction formula (5) and the sugar chain was elongated to convert the intermediate compound into LacNAc-CH$_2$CH(NH$_2$)(CH$_2$)$_9$CH$_3$, which was further supplied to an enzyme reaction using α2,6-sialyltransferase to lead to sialyl trisaccharide. Then, the side chain amino group in 6'-Sialyl-LacNAc-CH$_2$CH(NH$_2$)(CH$_2$)$_9$CH$_3$ and stearic acid were condensed by an amidation reaction to thus synthesize a sphingo sugar ceramide derivative a1.

Reaction Formula (5)

[Chemical Formula 13]

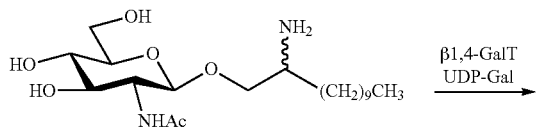

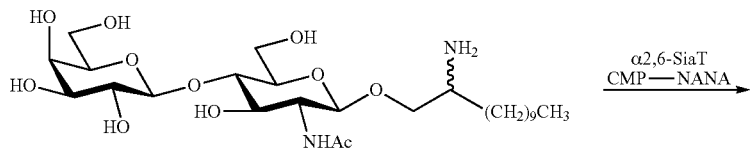

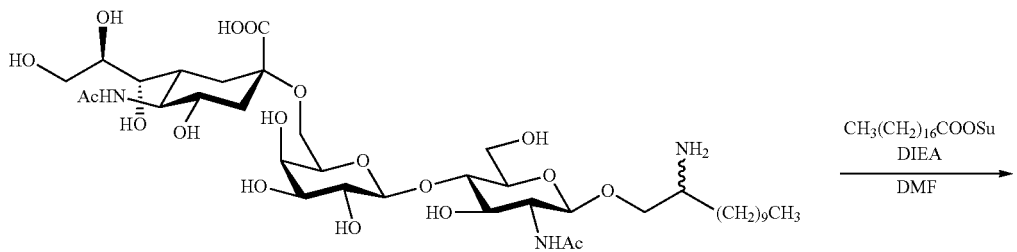

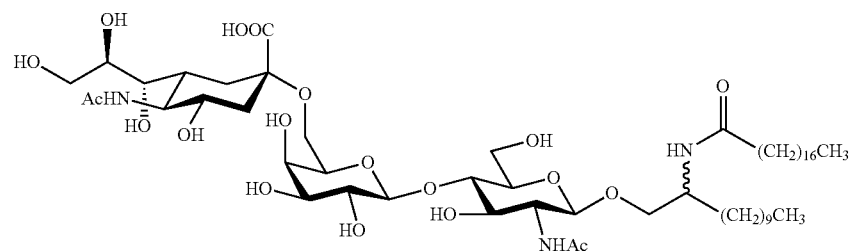

The compound a1 was purified by normal phase silica gel column chromatography (ethyl acetate:ethanol:water=6:2:1), and mass spectrometry by a $^1$H-NMR spectrum and MALDI-TOF was conducted to confirm the obtained compound.

(S) form: $^1$H NMR (400 MHz, CD$_3$OD): δ 4.46 (1H, d, J=8.0 Hz, H-1 Gal or Glc), 4.32 (1H, d, J=7.2 Hz, H-1 Gal or Glc), 4.04 (1H, bt, J=8.6 Hz, H-5 Gal), 2.77 (1H, dd, J=4.0, 12.4 Hz, H-3eq Sia (NeuAc)); MALDI-TOFMS: C$_{55}$HH$_{101}$N$_3$O$_{20}$ [M+Na]$^+$ calcd. (m/z) 1146.69, found. (m/z) 1146.49.

(R) form: $^1$H NMR (400 MHz, CD$_3$OD): δ 4.53 (1H, d, J=8.4 Hz, H-1 Gal or Glc), 4.32 (1H, d, J=7.2 Hz, H-1 Gal or Glc), 4.05 (1H, bt, J=8.8 Hz, H-5 Gal), 2.77 (1H, dd, J=4.0, 12.0 Hz, H-3eq Sia (NeuAc)); MALDI-TOFMS: C$_{55}$H$_{101}$N$_3$O$_{20}$ [M+Na]$^+$ calcd. (m/z) 1146.69, found. (m/z) 1146.55.

Production of Compound a2 (in the Case of n1=0 and n2=9 in the General Formula 1): Comparative Example

[Chemical Formula 14]

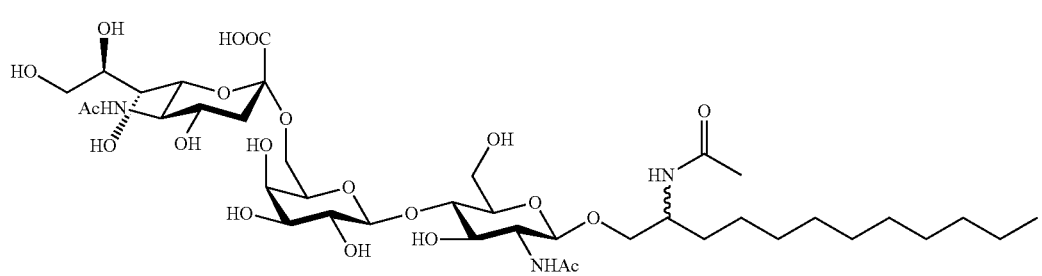

a2 a2 (S form) was synthesized in the same method as the above described compound a1 except for using acetic acid in place of stearic acid that is a fatty acid to be reacted with the side chain amino group.

The compound a2(S) was purified by normal phase silica gel column chromatography, and mass spectrometry by a $^1$H-NMR spectrum and MALDI-TOF was conducted to confirm the obtained compound.

(S) form: $^1$H NMR (400 MHz, CD$_3$OD): δ 4.46 (1H, d, J=8.4 Hz, H-1 Gal or Glc), 4.33 (1H, d, J=7.2 Hz, H-1 Gal or Glc), 4.04 (1H, bt, J=8.8 Hz, H-5 Gal), 2.77 (1H, dd, J=4.2,12.2 Hz, H-3eq Sia (NeuAc)), 2.00, 1.99 and 1.94 (3H×3, 3s, —NHC(=O)CH$_3$); MALDI-TOFMS: C$_{39}$H$_{69}$N$_3$O$_{20}$ [M+Na]$^+$ calcd. (m/z) 922.44, found. (m/z) 922.17.

Production of Compound a3-1 (in the Case of n1=22 and n2=9 in the General Formula 1)

[Chemical Formula 15]

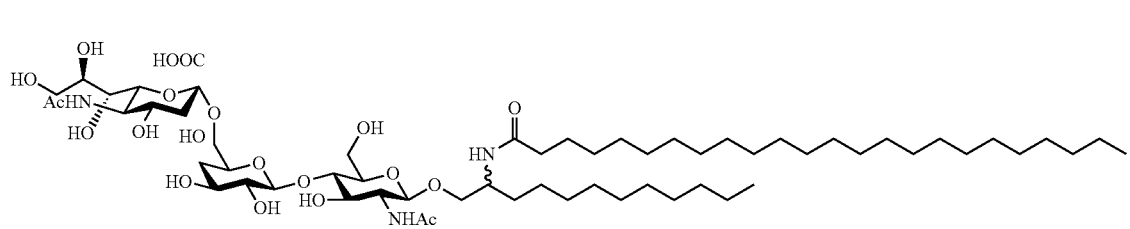

a3-1

An a3-1 (S) form was synthesized in the same method as the above described compound a1 except for using lignoceric acid in place of stearic acid that is a fatty acid to be reacted with the side chain amino group.

The compound a3-1(S) was purified by normal phase silica gel column chromatography (ethyl acetate:ethanol:water=6:2:1), and mass spectrometry by a $^1$H-NMR spectrum and MALDI-TOF was conducted to confirm the obtained compound.

$^1$H NMR (400 MHz, CD$_3$OD:CDCl$_3$=4:1): δ 4.44 (1H, d, J=8.0 Hz, H-1 Gal or Glc), 4.33 (1H, d, J=7.2 Hz, H-1 Gal or Glc), 2.77 (1H, dd, J=4.6, 12.2 Hz, H-3eq Sia (NeuAc)), 2.01 and 2.00 (3H×2,2s, —NHC(=O)CH$_3$)

MALDI-TOFMS: $C_{61}H_{113}N_3O_{20}$ [M+Na]$^+$ calcd. (m/z) 1230.78, found. (m/z) 1230.48.

Production of Compound a3-2 (in the Case of n1=22 and n2=5 in the General Formula 1)

[Chemical Formula 16]

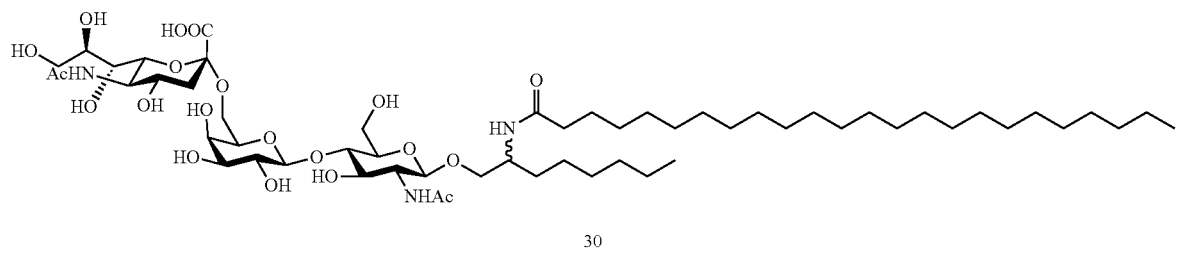

a3-2

The compound a3-2 was synthesized in the same method as the above described compound a3-1 except for using 2-azidooctanol, CH$_3$(CH$_2$)$_5$CH(N$_3$)CH$_2$OH, in place of 2-azidododecanol, CH$_3$(CH$_2$)$_9$CH(N$_3$)CH$_2$OH. Division of the (S) form and the (R) form was difficult in the intermediate of this compound and, therefore, synthesis was carried out directly with the racemic form. The compound a3-2 was purified by high performance liquid chromatography using a reversed phase column, and mass spectrometry by MALDI-TOF was conducted to confirm the obtained compound.

MALDI-TOFMS: $C_{57}H_{105}N_3O_{20}$ [M+Na]$^+$ calcd. (m/z) 1174.72. found. (m/z) 1174.78.

Production of Compound a3-3 (in the Case of n1=22, n2=13 in the General Formula 1)

[Chemical Formula 17]

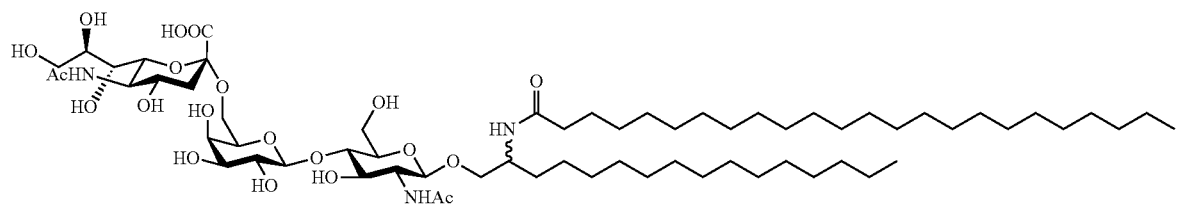

a3-3

The compound a3-3 was synthesized in the same method as the above described compound a3-1 except for using 2-azidohexadecanol, CH$_3$(CH$_2$)$_{16}$CH(N$_3$)CH$_2$OH, in place of 2-azidododecanol, CH$_3$(CH$_2$)CH(N$_3$)CH$_2$OH. Separation of the (S) form and the (R) form was difficult in the intermediate of this compound and, therefore, synthesis was carried out directly with the racemic form.

The compound a3-3 was purified by high performance liquid chromatography using a reversed phase column, and mass spectrometry by MALDI-TOF was conducted to confirm the obtained compound.

MALDI-TOFMS: $C_{65}H_{121}N_3O_2$ [M+Na]$^+$ calcd. (m/z) 1286.84. found. (m/z) 1287.26

(1-2) Production of Immunity Inducer Having Carbohydrate Structure, "Siaα2,3Galβ1,4GlcNAc"

Production of Compound b1 (in the Case of n1=16 and n2=9 in the General Formula 2)

[Chemical Formula 18]

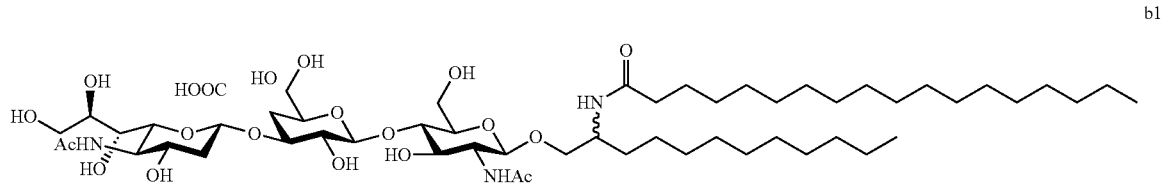

b1

The compound b1 was synthesized in the same method as the above described compound a1 except for using α2,3-sialyltransferase in place of α2,6-sialyltransferase in the above described reaction formula (5).

The compound b1 was purified by normal phase silica gel column chromatography (ethyl acetate:ethanol:water=7:2:1), and mass spectrometry by MALDI-TOF was conducted to confirm the obtained compound.

(S) form: MALDI-TOFMS: $C_{55}H_{101}N_3O_{20}$ $[M+Na]^+$ calcd. (m/z) 1146.69. found. (m/z) 1146.40.

(R) form: MALDI-TOFMS: $C_{55}H_{101}N_3O_{20}$ $[M+Na]^+$ calcd. (m/z) 1146.69. found. (m/z) 1145.42.

(1-3) Production of Immunity Inducer Having Carbohydrate Structure, "Galβ1,4GlcNAc"

Production of Compound c1 (in the Case of n1=16 and n2=9 in the General Formula 3)

[Chemical Formula 19]

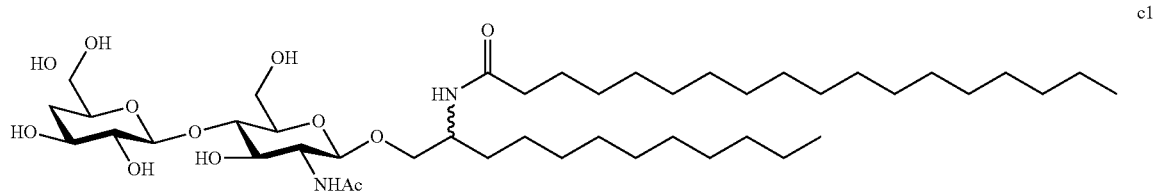

c1

The compound c1 was synthesized in the same method as the above described compound a1 except for supplying to an enzyme reaction using β1,4-galactosyltransferase and elongating the sugar chain to convert into LacNAc-CH$_2$CH(NH$_2$)(CH$_2$)$_9$CH$_3$, thereafter condensing the side chain amino group and stearic acid in the above described reaction formula (5).

The compound c1 was purified by normal phase thin-layer silica gel column chromatography (chloroform:methanol:water=5:4:1), and mass spectrometry by MALDI-TOF was conducted to confirm the obtained compound.

(S) form: MALDI-TOFMS: $C_{44}H_{84}N_2O_{12}$ $[M+Na]^+$ calcd. (m/z) 855.59. found. (m/z) 855.24.

(R) form: MALDI-TOFMS: $C_{44}H_{84}NO_{12}$ $[M+Na]^+$ calcd. (m/z) 855.59. found. (m/z) 855.13.-

(1-4) Production of Immunity Inducer Having Carbohydrate Structure, "Sialyl-Lewis$^x$ (Siaα2,3Galβ1,4(Fucα1,3)GlcNAc)"

Production of Compound sLe$^x$-C12L (Sialyl-Lewis$^x$ (Siaα2,3Galβ1,4(Fucα1,3)GlcNAc)-C12L)

[Chemical Formula 20]

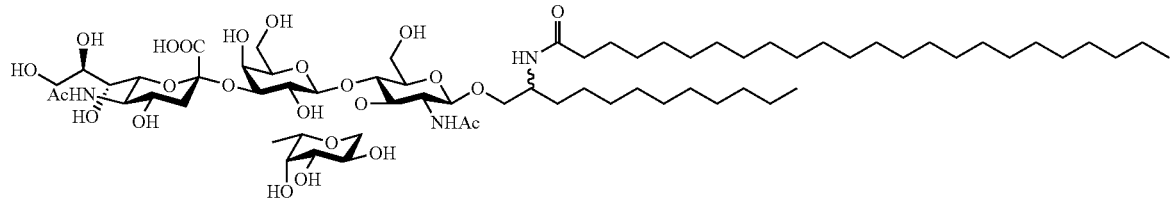

The compound sLe$^x$-C12L was synthesized in the same method as the above described compound a3-1 except for supplying to an enzyme reaction using α1,3-fucosyltransferase after the α2,3-sialyltransferase reaction and elongating the sugar chain to convert into sLe$^x$-CH$_2$CH(NH$_2$)(CH$_2$)$_9$CH$_3$ in the above described reaction formula (5).

The compound sLe$^x$-C12L was purified by normal phase thin-layer silica gel column chromatography, and mass spectrometry by MALDI-TOF was conducted to confirm the obtained compound.

MALDI-TOFMS: C$_{67}$H$_{123}$N$_3$O$_{24}$ [M+Na]$^+$ calcd. (m/z) 1376.84. found. (m/z) 1376.91.

(1-5) Production of Immunity Inducer Having Carbohydrate Structure, "Lewis$^x$ (Galβ1,4(Fucα1,3)GlcNAc)"

Production of Le$^x$-C12L (Galβ1,4(Fucα1,3)GlcNAc-C12L)

[Chemical Formula 21]

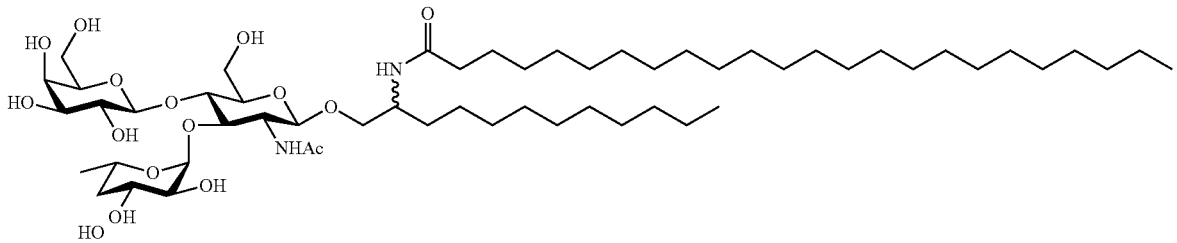

The compound Le$^x$-C12L was synthesized in the same method as the above described compound a3-1 except for supplying to an enzyme reaction using α1,3-fucosyltransferase after the β1,4-galactosyltransferase reaction and elongating the sugar chain to convert into sLe$^x$-CH$_2$CH(NH$_2$)(CH$_2$)$_9$CH$_3$ in the above described reaction formula (5).

MALDI-TOFMS: C$_{56}$H$_{106}$N$_2$O$_{16}$[M+Na]$^+$ calcd. (m/z) 1085.74. found. (m/z) 1085.96.

Example 2

Evaluation of Immunity Inducing Ability by Various Immunity Inducers (a1, b1, c1)

Next, each of racemic forms of various immunity inducers (a1, b1 and c1) synthesized in Examples (1-1), (1-2) and (1-3) was dissolved into s lipid containing cholesterol and phospholipid with an adjuvant (Lipid-A), and immunized a mouse being a host generally producing a monoclonal antibody (C3H/HeN strain) in a liposome method (Eur. J. Immunol., 16, 951-956, 1986) to evaluate the immunity inducing ability.

Each of the immunity inducers was subcutaneously immunized and additionally abdominally immunized after 2 weeks. After the additional immunization, the blood was collected after 3 days and 7 days, and the serum was examined. The antibody titer in the obtained serum was evaluated by ELISA method. In ELISA method, using two types of antigens of an immunogen and a glycoprotein (Fetuin) containing 6'-Sialyl-LacNAc, 3'-Sialyl-LacNAc and LacNAc structures, they were evaluated as an antibody titer to the immunogen and an antibody titer to the objective carbohydrate, respectively.

In addition, in order to evaluate subclasses (IgM and IgG) of immunoglobulin, an antibody specific to IgM and IgG was used as a secondary antibody to evaluate the subclasses. The antibody titer was evaluated as an activity of peroxidase that is a labeling enzyme of a secondary antibody. TMB was used for a chromogenic substrate of peroxidase, and an intensity of an absorbance at 450 nm after adding 2 N-sulfuric acid after the reaction was evaluated. The antibody titer of the IgM subclass is shown in FIGS. 1 and 2.

In all of the used compounds (a1, b1 and c1), significant increases of antibody titers in the case of $p<0.05$, $p<0.01$ and $p<0.001$ were confirmed respectively by ELISA using an immunogen (FIG. 1) and a glycoprotein (FIG. 2) as antigens. On the other hand, a significant antibody titer in the IgG subclass was not observed in the immunity inducers a1, b1 and c1 (not shown). In addition, a significant difference in immunity enhancing abilities between the (S) form and the (R) form was not confirmed in each of the compounds (not shown).

Example 3

Evaluation of Immunity Inducing Ability Due to Structural Change of Carrier Compound (3-1) Regarding Immunity Inducer Having Carbohydrate Structure "6'-Sialyl-LacNAcβ1 (CDw75)"

Next, in order to select a carrier compound having a higher activity, immunity inducing abilities were evaluated on 5 types of candidate compounds (a1, a2, a3-1, a3-2 and a3-3) each obtained by changing a structure of a carrier compound having the compound a1 synthesized in Example (1-1) as the basic structure in the same manner as described above.

Each of the immunity inducers was subcutaneously immunized on the first day, and the carrier compound was additionally abdominally immunized after 2 weeks. After the additional immunization, the blood was collected after 3 days and 7 days to prepare serums. Antibody titers of the obtained serums were evaluated by ELISA method. In ELISA method, using two types of antigens of an immunogen and a glycoprotein (Fetuin) containing a 6'-Sialyl-LacNAc structure, they were evaluated as an antibody titer to the immunogen and an antibody titer to the objective sugar chain, respectively. In addition, in order to evaluate subclasses (IgM and IgG) of produced immunoglobulin, an antibody specific to IgM and IgG was used as the secondary antibody to evaluate the subclasses. The antibody titer was evaluated as an activity of peroxidase that is a labeling enzyme of the secondary antibody. TMB was used for a chromogenic substrate of peroxidase, and an intensity of an absorbance at 450 nm after adding 2 N-sulfuric acid after the reaction was evaluated. The antibody titer of the IgM subclass is shown in FIG. 3. In all of the compounds (a1, a2, a3-1 and a3-2), significant increases of antibody titers were confirmed respectively by ELISA using an immunogen and Fetuin as antigens. Although a3-3 was in short of the individual number necessary for a significant difference test, tendency of increasing an antibody titer was confirmed. Among the evaluated compounds, the antibody titer of a2 was the lowest, and the activity of a3-1 was the highest in the examined compounds. As a fatty acid had a longer chain, immunogenicity tended to increase more, and as compared to the compound a2 containing the shortest chain fatty acid, the antibody titer to the immunogen in the serum was approximately 12 times, and immunogenicity to Fetuin was 8 time or higher. Even though class switching to IgG was insufficient because of only primary additional immunization, in the serums after 7 days from immunization by a3-1 and a3-2 each containing a very long chain fatty acid (lignoceric acid), a significant increase of the antibody titer was confirmed when an immunogen itself was used as the antigen also in a fraction of the IgG subclass (FIG. 4). It is found from this result that an IgG class antibody to an immunogen is produced by class switching only by primary additional immunization and functions as a thymus-dependent antigen.

(3-2) Regarding Immunity Inducing Ability of Ceramide being Natural Substance

As a result of the above described examination, an intensive immunogenicity enhancement action was found in a ceramide analog containing a long chain fatty acid (very long chain fatty acid). In the case of a ceramide being a natural substance, it is structurally different from the immunity inducer of the present invention, which is a ceramide analog, in the point of having a hydroxyl group in an alkyl group of the amino group side and also having an unsaturated bond; however, even a ceramide being a natural substance also contains such a very long chain fatty acid in cases. Thus, considering a possibility that a very long chain fatty acid-containing ceramide itself that is a natural substance has high immunogenicity, the degree of the immunogenicity was examined. The examined natural substance ceramide is the following globoside having a fatty acid with 24 carbon atoms (corresponding to n1=22).

[Chemical Formula 22]

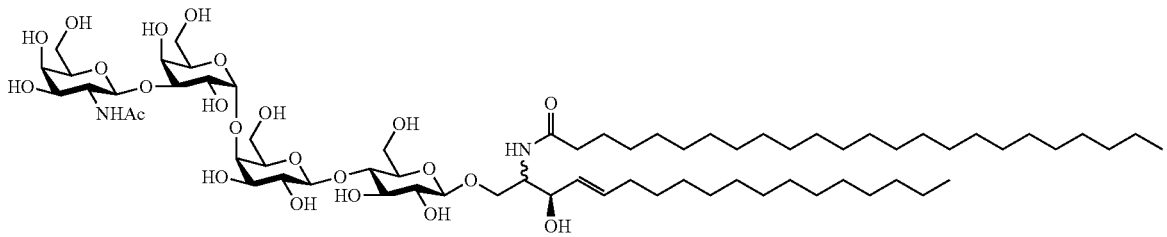

Globoside (C24) (GalNAcβ1, 3Galα1, 4Galβ1, 4Gicβ1-Ceramide)

Globoside used in the examination is a purified product derived from human erythrocytes, and is obtained by bonding a ceramide containing a very long chain fatty acid (lignoceric acid) to a P antigen carbohydrate of the human P blood group. (Okuda T., et al., Glycoconjugate journal, 27, 287-296, 2010)

As compared to the a3-1 structure having the highest immunogenicity among developed ceramide analogs, this structure is different in the points that the length of an alkyl chain in an aminoalkyl moiety (sphingosine) is C18, a hydroxyl group is contained at the third position, and an unsaturated bond is contained at the fourth position; however, the entire structure is similar.

Figure 5:
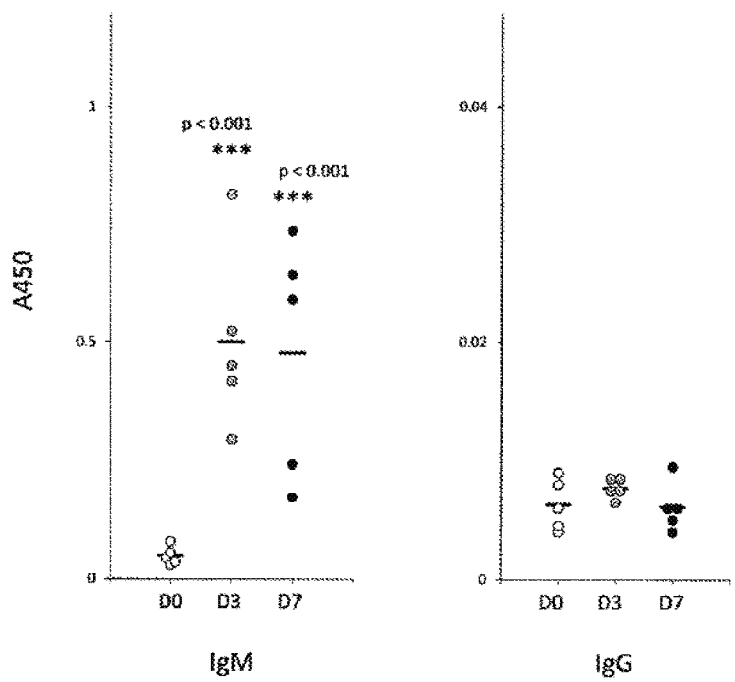
FIG. 5 illustrates serum antibody titers after immunity induction by Globoside: a serum antibody titer of a mouse when immunized with a natural glycosphingolipid (Globoside) is shown for comparison. Antibody titers of the IgM subclass (left figure) and antibody titers of IgG subclass (right figure) in mouse serums after immunity induction were evaluated as reactivity to a target sugar chain epitope by ELISA. White circles denote antibody titers in unimmunized mouse serums (D0), gray circles denote antibody titers in mouse serums after 3 days from the final immunization (D3), black circles denote antibody titers in mouse serums after 7 days from the final immunization (D7); and the antibody titers in mouse serums were individually plotted in the graphs (n=5). It was confirmed that, as compared to the serum antibody titers in unimmunized mice, each of the serum antibody titers of D3 and D7 significantly increased by a Student's t test. ($***p<0.001$)

FIG. 5 illustrates a serum antibody of a mouse when immunized with globoside in a liposome method. In the IgM subclass in the mouse serum after immunity induction (FIG. 5, left view), a significant increase of the antibody titer to the immunogen (globoside) was confirmed in the serums after 3 days and 7 days from the immunization. On the other hand, an increase of the antibody titer was not confirmed in the IgG subclass (FIG. 5, right view).

This result suggests that a glycolipid compound bound with a ceramide being a natural substance has immunogenicity, but cannot exert a sufficient activity as a thymus-dependent antigen even though the glycolipid compound is a molecular species containing a very long chain fatty acid.

Example 4

Evaluation of Immunity Inducers Having Carbohydrate Structures of "Sialyl-Lewis$^X$ (Siaα2,3Galβ1,4(Fucα1,3)GlcNAc)" and "Lewis$^X$ (Galβ1,4(Fucα1,3)GlcNAc)"

As a result of the examination in the above described (Example 3) (3-1), in order to examine general versatility of the C12L compound in which the highest immunogenicity was confirmed to a fucosylated carbohydrate, immunity inducing ability to an objective oligosaccharide antigen in conjugates (sLe$^X$-C12L and Le$^X$-C12L) with a Sialyl Lewis$^X$ (sLe$^X$) oligosaccharide, which was produced in Example 1 (1-4) and is a typical fucosylated carbohydrate, and a Lewis$^X$ (Le$^X$) oligosaccharide, which was produced in Example 1 (1-5) and is a typical asialo carbohydrate, were verified. sLe$^X$ and Le$^X$ are oligosaccharide antigens useful as a tumor marker and a stem cell marker as described above.

Figure 9:
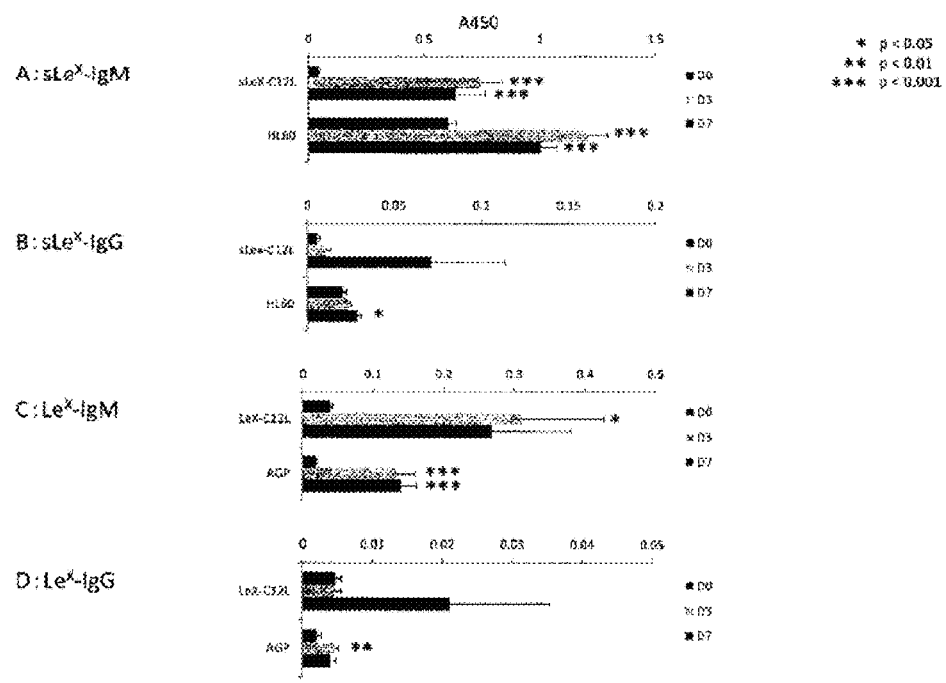
FIG. 9 illustrates serum antibody titers after immunity inductions with sLe$^x$-C12L and Le$^x$-C12L: after immunizing a mouse using each of the sLe$^x$-C12L and Le$^x$-C12L compounds as an immunity inducer, an antibody titer of each subclass (IgM and IgG) of immunoglobulin in the serum was evaluated by ELISA. A and B show serum antibody titers of a mouse immunized with sLe$^x$-C12L, C and D show serum antibody titers of a mouse immunized with Le$^x$-C12. A and C: Evaluations on an immunogen used as an antigen by ELISA. B: Evaluation on a cell extract (HL60) containing a glycoprotein including an epitope of a target carbohydrate used as an antigen by ELISA. D: Evaluation on a glycoprotein (AGP) containing an epitope of a target carbohydrate as an antigen by ELISA. Regarding D0, serum antibody titers before immunization; D3, serum antibody titers after 3 days from the final immunization; and D7, serum antibody titers after 7 days from the final immunization, respective antibody titers in mouse serums were shown in graphs. It was confirmed that, as compared to the serum antibody titers in unimmunized mice, each of the serum antibody titers of D3 and D7 significantly increased by a Student's t test. (*$p<0.05$, $p<0.01$, *$p<0.001$, $n=8$)

FIG. 9 illustrates a serum antibody titer of a mouse when immunized with each compound. In the IgM subclass in a mouse serum immunized with sLe$^X$-C12L (FIG. 9, A), significant increases of antibody titers to an immunogen and a glycoprotein (HL60) containing an objective oligosaccharide antigen were confirmed in the serums after 3 days and 7 days from the immunization. Even in the case of the IgG subclass (FIG. 9, B), sufficient IgG class switching occurred regardless of only primary additional immunization, tendency of an increase of an antibody titer to an immunogen was confirmed after 7 days from the immunization, and a significant increase of an antibody titer to a glycoprotein (HL60) was also confirmed.

In the IgM subclass in a mouse serum immunized with Le$^X$-C12L (FIG. 9, C), significant increases of antibody titers to an immunogen and a glycoprotein (AGP) containing an objective oligosaccharide antigen were confirmed in the serums after 3 days and 7 days from immunization. Even in the case of the IgG subclass (FIG. 9, D), tendency of an increase of an antibody titer to an immunogen was confirmed after 7 days from immunization, and a significant increase of an antibody titer to a glycoprotein (AGP) was also confirmed after 3 days from immunization.

The above described results testified that the carrier compound (C12L) developed in the present invention can impart an intensive immunity inducing activity to any of typical oligosaccharide antigens each classified into a fucosylated carbohydrate, and also a sialylated carbohydrate and an asialo (non-sialylated) carbohydrate. That is, it was able to be confirmed that the carrier compound of the present invention is a techniques applicable to all of a sialylated carbohydrate, an asialo (non-sialylated) carbohydrate and a fucosylated carbohydrate, which are oligosaccharide antigens each contained in an N-linked sugar chain that exists in a mammalian glycoprotein.

Example 5

Production of Monoclonal Antibody

It was confirmed that, using a3-1 (CDw75-C12L) having the most intensive immunogenicity confirmed in the above described Example 3, a specific antibody to an objective carbohydrate epitope was actually produced. Specifically, a monoclonal antibody was produced as described below.

(5-1) Production of Anti-CDw75 Monoclonal Antibody Producing Hybridoma

100 μg of a glycolipid antigen "CDw75-C12L" was mixed in a methanol solution with a phospholipid, cholesterol, and Lipid-A according to the liposome method (method by Brodin, et al.; Eur. J. Immunol., 16, 951-956, 1986) and evaporated, thereafter dissolving into a PBS buffer solution at 50° C. to thus form a liposome, and a mouse (C3H/HeN strain) was immunized with this liposome as an immunity inducer.

The immunity inducer was subcutaneously immunized 4 times at the interval of 2 weeks, and abdominally immunized after 2 weeks, the spleen cell was then collected after 3 days, and hybridoma cells were prepared by cell fusion with a myeloma cell Sp1 strain.

The antibody titer in the culture supernatant was evaluated by ELISA method, and a hybridoma was selected based on 0.1 or more of an absorbance at 450 nm as the index. The antibody titer (absorbance) was evaluated as an activity of peroxidase that is a labeling enzyme of an anti-mouse immunoglobulin antibody used as a secondary antibody. TMB was used for a chromogenic substrate of peroxidase, and an intensity of an absorbance at 450 nm after adding 2 N-sulfuric acid after the reaction was evaluated.

First, culture supernatants of hybridoma cells cultured in eight 96-well plates so as to have the colony number 1/well (totally 768 wells) were collected in an amount of 0.05 ml each, and a monoclonal antibody producing hybridoma cell which recognizes a glycoprotein (Fetuin) containing a 6'-Sialyl-LacNAc (CDw75) carbohydrate structure was selected based on the index of 0.1 or more of an absorbance at 450 nm by ELISA as an antibody titer to thus obtain positive clones in 131 wells (appearance ratio of 17.1%).

On the other hand, in the conventional technique (Non Patent Literature 8), a phospholipid (phosphatidylethanolamine) was used as a carrier compound, an antibody having a CDw75 carbohydrate as an epitope was induced in the same manner, and an appearance ratio of positive clones in this stage was, however, only 8 wells out of selected 581 wells (appearance ratio of 1.3%).

Subsequently, a monoclonal antibody-producing hybridoma cell having no reactivity to a glycolipid antigen "CDw75-C12L" to be an immunogen, "Galβ1,4GlcNAc" of the general formula (5) to be a precursor, glycolipids (b1 and c1 in Table 1) each having the carbohydrate structure of "Siaα2,3Galβ1,4GlcNAc" of the general formula (4), which is the most similar to the objective oligosaccharide in the structure among and carbohydrates existing in a mammalian body, and a glycoprotein (Fetuin-a) were selected, and two cell lines were finally isolated as clones having high affinity.

Monoclonal antibodies obtained from these hybridomas are all anti-CDw75 monoclonal antibodies having high specificity to the "CDw75" carbohydrate structure, and each is the anti-CDw75 monoclonal antibody of the present invention.

Between these two hybridomas, "hybridoma FR9" which produces an anti-CDw75 monoclonal antibody having the highest antibody titer and more excellent specificity and affinity was deposited to NITE Patent Microorganisms Depositary dated on Jan. 21,2013. "Accession number: NITE P-1516" was given dated on Mar. 13, 2013, and the hybridoma FR9 was then transferred to the international depositary as "NITE BP-01516" dated on Apr. 15, 2014.

(5-2) Evaluation of Monoclonal Antibody Produced by Hybridoma FR9

When affinity to CDw75 of the monoclonal antibody (hereinafter also referred to as the "FR9 antibody") contained in a culture supernatant of FR9 cells was evaluated by determining a dissociation constant (Kd value) using Fetuin containing CDw75 as the antigen, the Kd value was 8.86× 10$^{-7}$ M. Since Kd values of an antibody bonding to a carbohydrate and lectin are generally from $1\times10^{-3}$ to $1\times10^{-6}$ M, the developed antibody has intensive affinity to a CDw75 carbohydrate (FIG. 6A).

In the measurement result of detection limits of Fetuin and CDw75-C12L by ELISA method, a trace amount of Fetuin (about 15 ng) was detectable in the FR9 antibody (FIG. 6B). On the other hand, an antibody induced in the conventional technique (Non Patent Literature 8) requires 50 μg or more of Fetuin for detection, and it is therefore found that the FR9 antibody has 3000 times or higher detection sensitivity than the antibody prepared in the known technique.

Figure 7:
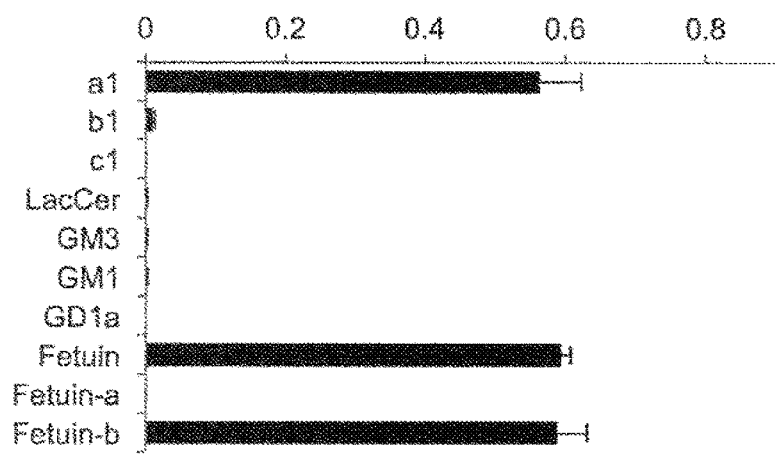
FIG. 7 illustrates a specificity analysis on the developed monoclonal antibody FR9 by ELISA method: the antigen recognition specificity of the FR9 antibody was analyzed in the ELISA method using various carbohydrate antigen compounds shown in Table 1.

Then, antigen recognition specificity of the FR9 antibody was evaluated by ELISA (FIG. 7). A sugar chain structure of a used antigen is shown in Table 1. The FR9 antibody strictly identifies epitopes only in a glycolipid and a glycoprotein each of which has the CDw75 structure as the antigen and does not react to a 3'-Sialyl-LacNAc structure having a similar structure and a LacNAc structure being a precursor; therefore, the developed antibody has high specificity to CDw75 carbohydrates.

Figure 8:
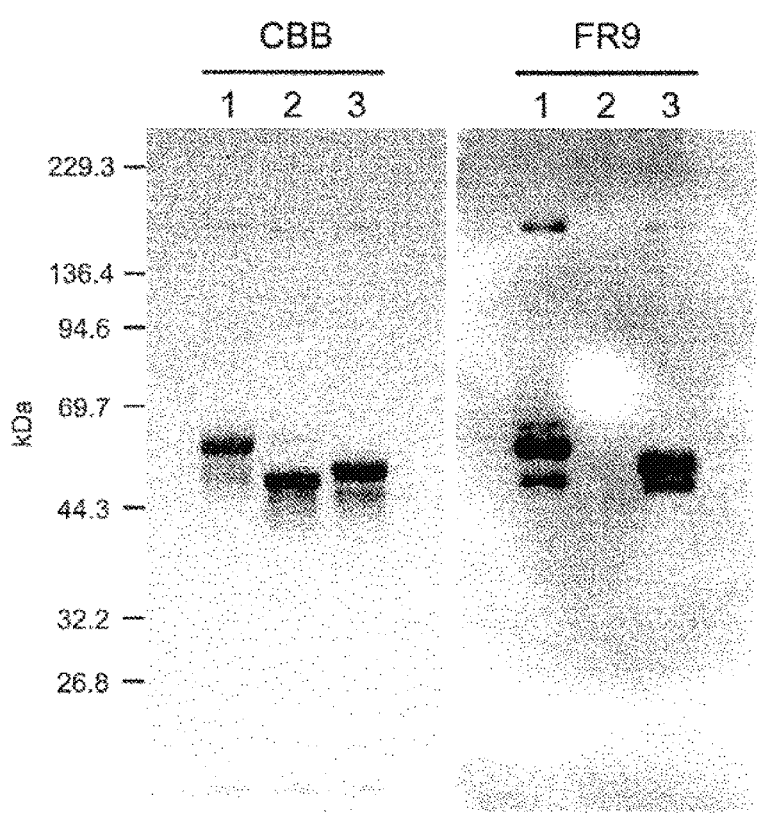
FIG. 8 illustrates a specificity analysis on a monoclonal antibody FR9 by a western blot method: applicability of the FR9 antibody to the western blot method was evaluated. The left figure shows a CBB staining image of the used Fetuin glycoprotein, and the right figure shows its western blot image. 1: Fetuin glycoprotein, 2: Fetuin glycoprotein (Fetuin-a) in which all sialic acids are decomposed with an enzyme, and 3: Fetuin glycoprotein (Fetuin-b) in which α2,3-linked sialic acids are only selectively decomposed with an enzyme.

Subsequently, applicability of the FR9 antibody to a western blot method generally applied for detection of a specific protein was examined (FIG. 8).

When materials obtained by treating a Fetuin glycoprotein containing the 6'-Sialyl-LacNAc structure as the antigen with two types of sialidases were prepared and an analysis of specificity was carried out in parallel, the FR9 antibody detected a Fetuin glycoprotein, and did not react to a material with a CDw75 carbohydrate allowed to disappear by an enzyme reaction and, on the other hand, react to a Fetuin glycoprotein in which a 3'-Sialyl-LacNAc carbohydrate was allowed to selectively disappear in the same level as untreated Fetuin.

Therefore, it was testified that the immunity inducer developed by the present invention produces a specific antibody to an objective carbohydrate epitope, and the produced antibody has high activity and performance applicable to various uses. On the other hand, specificity and affinity were examined also in a commercially available anti-CDw75 antibody (LN-1) in the same technique for comparison, which were however detection limits or less by ELISA, and specificity and affinity to the CDw75 carbohydrate itself were confirmed to be very low.

Figure 10:
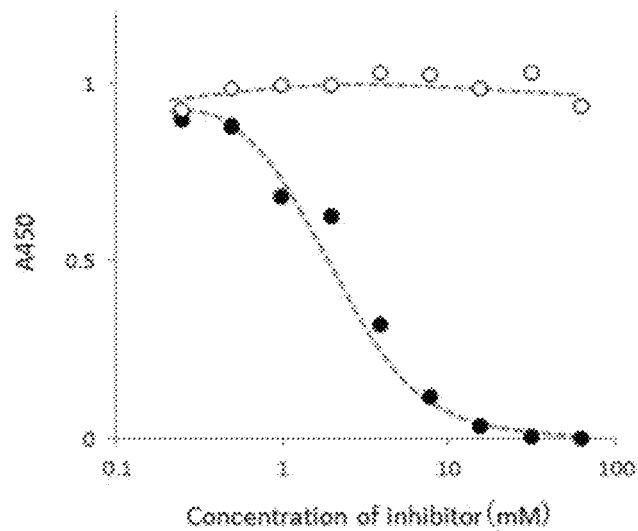
FIG. 10 illustrates a specificity analysis on a monoclonal antibody FR9 by a competitive inhibition assay: affinity of the FR9 antibody to sialyllactose (Siaα2,6Galβ1,4Glc) was analyzed by a competitive inhibition assay. Sialyllactose (white circle) or a CDw75 oligosaccharide chain (black circle) was added as an antagonist, and its effect was evaluated by ELISA. The concentrations of the antagonists are shown in the x axis, and the bonding amounts of the FR9 antibody are shown in the y axis.

Furthermore, in order to verify high recognition specificity of the anti-CDw75 antibody (FR9 antibody) of the present invention, 6'-Sialyllactose having a carbohydrate structure that is very similar to CDw75 was confirmed by a competitive inhibition assay with Fetuin formed into a solid phase (FIG. 10). A reaction between the FR9 antibody and Fetuin is inhibited by adding a CDw75 carbohydrate, and it is found that 6'-Sialyllactose is not reacted with the FR9 antibody since the reaction is not inhibited even when 6'-Sialyllactose is added.

Figure 11:
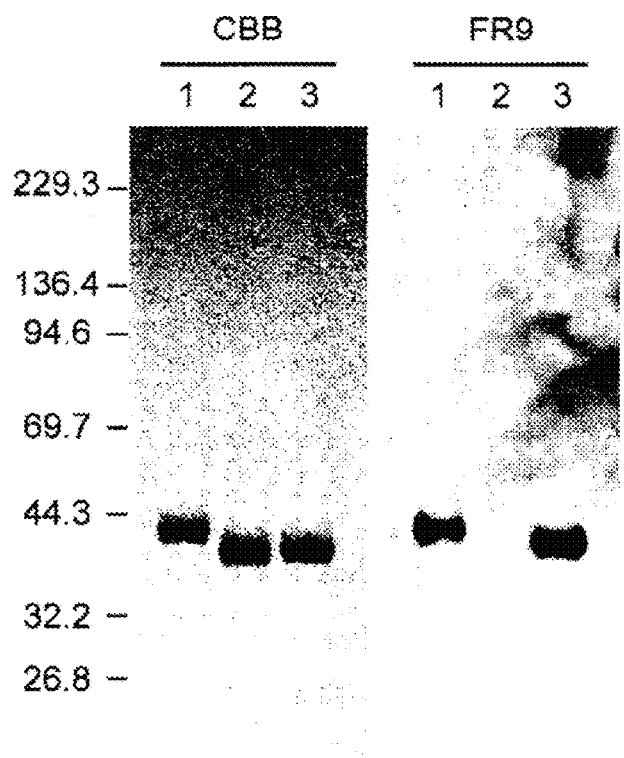
FIG. 11 illustrates a specificity analysis-2 on a monoclonal antibody FR9 by a western blot method: applicability of the FR9 antibody to the western blot method was evaluated. The left figure shows a CBB chromatic image of a used α1-acid glycoprotein (AGP), and the right figure shows its western blot image. 1: AGP, 2: AGP (AGP-a) in which all sialic acids are decomposed with an enzyme, and 3: AGP (AGP-b) in which α2,3-linked sialic acids are only selectively decomposed with an enzyme.

In addition, it was confirmed from a western blot analysis using an AGP glycoprotein that the anti-CDw75 antibody (FR9 antibody) of the present invention has similar reactivity to the case of Fetuin even when a CDw75 carbohydrate is contained in a glycoprotein other than a Fetuin glycoprotein and, at the same time, the reactivity is selective recognition specificity (FIG. 11). Here, it was confirmed that, since an AGP glycoprotein contains "3'-Sialyl-LacNAc (Siaα2,3Galβ1,4GlcNAc)" as a carbohydrate structure with "CDw75 (Siaα2,6Galβ1,4GlcNAc)" in the same manner as a Fetuin glycoprotein, an antibody titer observed to AGP lacks to AGP (AGP-a) in which sialic acid was removed and an antibody titer was not changed to AGP (AGP-b) in which the "3'-Sialyl-LacNAc" structure was selectively removed. Main carbohydrate structures of AGP, AGP-a and AGP-b are shown in Table 2. R represents the basic structure of AGP (AGP carbohydrate which constitutes the reducing side of the carbohydrate structure shown in the table and the core protein moiety).

TABLE 2

| Antigen | Structure |
|---------|-----------|
| AGP | Siaα2,6(3)Galβ1,4GlcNAcβ1-R |
|  | Galβ1,4(Fucα1,3)GlcNAcβ1-R |
| AGP-a | Galβ1,4GlcNAcβ1-R |
|  | Galβ1,4(Fucα1,3)GlcNAcβ1-R |
| AGP-b | Siaα2,6Galβ1,4GlcNAcβ1-R |
|  | Galβ1,4GlcNAcβ1-R |
|  | Galβl,4(Fucα1,3)GlcNAcβ1-R |

Figure 12:
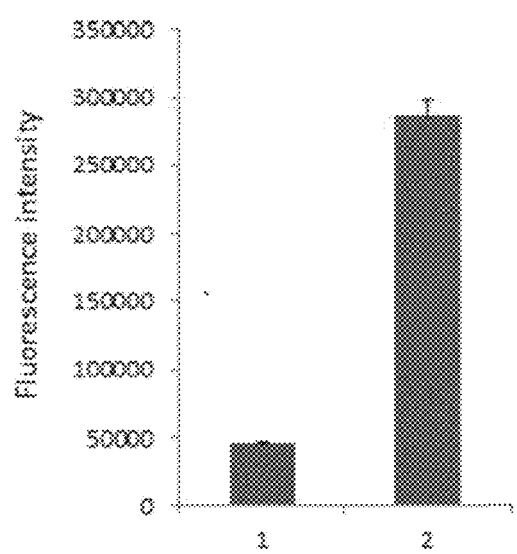
FIG. 12 illustrates detection of CDw75 expressed on a surface layer of a cancer cell (B-cell tumor cell): CDw75 expressed on a cellular surface layer of a B-cell tumor cell (Burkitt lymphoma cell line: Raji cell) was detected using the FR9 antibody. 1: negative control, 2: FR9 antibody.

(5-3) Regarding Capability of Detecting CDw75 Existing in Cancer Cell Surface Layer A CDw75 sugar chain is expressed as a cell surface layer antigen in the form of a glycoprotein or a glycolipid, and the cell surface layer antigen is a molecular target of cell diagnosis and malignant tumors. The FR9 antibody was confirmed to react with CDw75 in a cell surface layer by a cell fluorescence stain method. Highly malignant B-cell tumor cells expressing CDw75 (Raji cells of Burkitt lymphoma) were incubated with the FR9 antibody, and the antibody reaction was then labeled with a fluorescent labeling secondary antibody to detect CDw75 with a fluorescence detector (FIG. 12). As compared to a negative control without adding the FR9 antibody, it was found that since an apparent increase of fluorescence was detected, the FR9 antibody is reacted to CDw75 in a Raji cell surface layer.

(5-4) Comparison with CDw75 Carbohydrate Antigen-recognizing Monoclonal Antibody Described in Conventional Technique Document (Non Patent Literature 8)

Since a monoclonal antibody (241-5-2 antibody) which recognizes a CDw75 carbohydrate antigen was also obtained in the conventional technique document (Non Patent Literature 8), its specificity and affinity are compared with the result of the anti-CDw75 antibody (FR9 antibody) of the present invention.

According to the description in Non Patent Literature 8, even though the obtained 241-5-2 antibody reacts with a Fetuin glycoprotein containing a CDw75 carbohydrate, an epitope that the 241-5-2 antibody recognizes is assumed to be the "Siaα2,6 structure" that is a partial structure in the CDw75 carbohydrate, "6'-Sialyl-LacNAc (Siaα2,6Galβ1,4GlcNAc)" (p. 303 in the same document). That is, the 241-5-2 antibody cannot be regarded as an antibody specific to the CDw75 carbohydrate, and reacts with a carbohydrate as long as the carbohydrate has the "Siaα2,6 structure".

On the other hand, the FR9 antibody of the present invention is an antibody that recognizes even a fine structure of a CDw75 carbohydrate, and "6'-Sialyl-LacNAc (Siaα2, 6Galβ1,4GlcNAc)" containing, not only the Siaα2,6 structure, but also even the whole length of the GlcNAc structure in the reducing end is an epitope. The FR9 antibody has rigorous epitope recognition specificity of not reacting when GlcNAc is Glc (FIG. 10), and it is considered that very high specificity could be attained as compared to an existing antibody.

In addition, according to the result of a measurement on the 241-5-2 antibody by ELISA in Non Patent Literature 8 (p. 302), 50 μg or more Fetuin is required for detecting Fetuin. On the other hand, the FR9 antibody of the present invention is capable of detecting a trace amount (about 15 ng) of Fetuin (FIG. 6B). It is found in view of the fact that the FR9 antibody of the present invention could also attain 3000 times or higher affinity to the CDw75 carbohydrate antigen as compared to the 241-5-2 antibody.

As described above, a monoclonal antibody obtained by applying the immunity inducing method of the present invention is a monoclonal antibody having high specificity and affinity to an objective oligosaccharide antigen.

INDUSTRIAL APPLICABILITY

An immunity inducer to a carbohydrate can be utilized in development of a polyclonal antibody or a monoclonal antibody, which recognizes a specific carbohydrate structure. The developed antibody can be applied to a basic research relating to a carbohydrate function and research development for industrial applications, and a demand as a reagent for research is expected. A molecular species specifically expressing in pathologic cells such as cancer cells among carbohydrates is expected in applications as a diagnostic drug and an antibody pharmaceutical product by development of a specific antibody. The developed immunity inducer is also expected in applications as a vaccine in various diseases such as cancer and virus infection which relate to carbohydrates.

The invention claimed is:
1. An immunity inducer comprising an artificial glycolipid or a salt thereof as an effective component, wherein the artificial glycolipid has the chemical formula (2) and includes the target oligosaccharide antigen R:

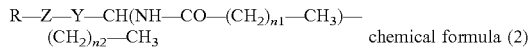

chemical formula (2)

wherein, in the chemical formula (2), R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —(CH$_2$)$_m$—, n1 represents an integer from 2 to 40, n2 represents an integer from 1 to 27, and m represents an integer from 1 to 30, and wherein the target oligosaccharide antigen R is selected from the group consisting of an oligosaccharide antigen included in a mammal-derived glycoprotein N-linked sugar chain selected from the group consisting of Siaα2,6Galβ1,4GlcNAc, Siaα2,3Galβ1,4GlcNAc, Galβ1,4GlcNAc, Galβ1,3GlcNAc, Siaα2,3Galβ1,4(Fucα1,3)GlcNAc, Galβ1,4(Fucα1,3)GlcNAc, Siaα2,3Galβ1,3(Fucα1,4)GlcNAc, Siaα2,3Galβ1,3GlcNAc, Galβ1,3(Fucα1,4)GlcNAc, Siaα2,3Galβ1,3 (Siaα2,6)GlcNAc, Siaα2,3Galβ1,3 (Fucα1,4)(Siaα2,6)GlcNAc, Fucα1,2Galβ1,3(Fucα1,4)GlcNAc, Fucα1,2Galβ1,4GlcNAc, Fucα1,2Galβ1,4(Fucα1,3)GlcNAc, Fucα1,6GlcNAc, GlcNAcβ1,4(Fucα1,6)GlcNAc, Manβ1,4GlcNAcβ1,4(Fucα1,6)GlcNAc, Manα1,6(Manα1,3)Manβ1,4GlcNAcβ1,4(Fucα1,6)GlcNAc, Manα1,6(GlcNAcβ1,4)(Manα1,3)Manβ1,4GlcNAcβ1,4GlcNAc, Manα1,6(GlcNAcβ1,4)(Manα1,3)Manβ1,4GlcNAcβ1,4(Fucα1,6)GlcNAc, GlcNAcβ1,4GlcNAc, Manβ1,4GlcNAcβ1,4GlcNAc, GlcNAcβ1,2Man, GlcNAcβ1,4Man, GlcNAcβ1,6Man, Galβ1,3GlcNAcβ1,2Man, Galβ1,3GlcNAcβ1,4Man, Galβ1,3GlcNAcβ1,6Man, Galβ1,4GlcNAcβ1,2Man, Galβ1,4GlcNAcβ1,4Man, Galβ1,4GlcNAcβ1,6Man, Siaα2,3Galβ1,4GlcNAcβ1,2Man, Siaα2,3Galβ1,4GlcNAcβ1,4Man, Siaα2,3Galβ1,4GlcNAcβ1,6Man, Siaα2,3Galβ1,3GlcNAcβ1,2Man, Siaα2,3Galβ1,3GlcNAcβ1,4Man, Siaα2,3Galβ1,3GlcNAcβ1,6Man, Siaα2,6Galβ1,4GlcNAcβ1,2Man, Siaα2,6Galβ1,4GlcNAcβ1,4Man, Siaα2,6Galβ1,4GlcNAcβ1,6Man, GalNAcβ1,4GlcNAc, GalNAcβ1,4GlcNAcβ1,2Man, GalNAc(4SO$_4$)β1,4GlcNAc, GalNAc(4SO$_4$)β1,4GlcNAcβ1,2Man, GalNAc(4SO$_4$)β1,4GlcNAcβ1,4Man, GalNAc(4SO$_4$)β1,4GlcNAcβ1,6Man, GlcAβ1,3Galβ1,4GlcNAc, GlcA(3SO$_4$)β1,3Galβ1,4GlcNAc, Siaα2,3Galβ1,4(Fucα1,3)GlcNAc(6 SO$_4$), Siaα2,3Galβ1,4GlcNAc(6SO$_4$), Galβ1,4GlcNAc(6SO$_4$), Galβ1,4(Fucα1,3) GlcNAc(6SO$_4$), Siaα2,3Gal(6SO$_4$)β1,4(Fucα1,3)GlcNAc, Siaα2,3Gal(6SO$_4$)β1,4GlcNAc, Gal(6SO$_4$)β1,4GlcNAc, Gal(6SO$_4$)β1,4GlcNAc(6SO$_4$), Galβ1,4GlcNAcβ1,3Gal, GlcNAcβ1,3Galβ1,4GlcNAc, Galβ1,4GlcNAc(6SO$_4$)β1,3Gal, GlcNAc(6SO$_4$)β1,3Galβ1,4GlcNAc, Gal(6SO$_4$)β1,4GlcNAc(6SO$_4$)β1,3Gal, GlcNAc(6SO$_4$)β1,3Gal(6SO$_4$)β1,4GlcNAc, Siaα2,3Galβ1,4GlcNAcβ1,3Galβ1,4(Fucα1,3)GlcNAc, Fucα1,2Galβ1,3GlcNAc, Galα1,3(Fucα1,2)Galβ1,3GlcNAc, Galα1,3(Fucα1,2)Galβ1,4GlcNAc, GalNAcα1,3(Fucα1,2)Galβ1,3GlcNAc, GalNAcα1,3(Fucα1,2)Galβ1,4GlcNAc, Fucα1,2Galβ1,4(Fucα1,3)GlcNAcβ1,3Gal, Gal(3SO$_4$)β1,4GlcNAc, Gal(3SO$_4$)β1,4(Fucα1,3)GlcNAc, Gal(3SO$_4$)β1,3GlcNAc, Gal(3SO$_4$)β1,3(Fucα1,4)GlcNAc, Gal(3SO$_4$)β1,4GlcNAc(6SO$_4$), Gal(3SO$_4$)β1,4(Fucα1,3)GlcNAc(6SO$_4$), Siaα2,8Siaα2,8Sia, Siaα2,6GalNAcβ1,4GlcNAc, Siaα2,3Galβ1,4(Fucα1,3)GlcNAcβ1,3Galβ1,4(Fucα1,3)GlcNAc, Galβ1,4GlcNAcβ1,3(Galβ1,4GlcNAcβ1,6)Gal, and Siaα2,3Galβ1,4GlcNAcβ1,3(Siaα2,3Galβ1,4GlcNAcβ1,6)Gal, an oligosaccharide antigen included in a mammal-derived glycoprotein O-linked sugar chain selected from the group consisting of Siaα2,3Galβ1,3GalNAc, Galβ1,3GalNAc, Siaα2,3Galβ1,3(GlcNAcβ1,6)GalNAc, GalNAcα1,3GalNAc, GlcNAcβ1,3(Siaα2,6)GalNAc, GalNAcα1,6GalNAc, GlcNAcβ1,6GalNAc, Fucα1,2GalNAc, Galβ1,3(GlcNAcβ1,6)GalNAc, Siaα2,6GalNAc, Siaα2,6(GlcNAcβ1,6)GalNAc, Siaα2,3Galβ1,3(Siaα2,6)GalNAc, Galβ1,4GalNAc, Siaα2,3Galβ1,4GalNAc, GlcNAcα1,4Gal, GlcNAcα1,4Galβ1,4GlcNAc, GlcNAcα1,4Galβ1,4GalNAc, GlcNAcα1,4Galβ1,4(GlcNAcα1,4Galβ1,4GlcNAcβ1,6)GalNAc, Siaα2,3Galβ1,4(Fucα1,3)GlcNAc(6SO$_4$)β1,6GalNAc, Gal(3SO$_4$)β1,4GlcNAcβ1,6(Siaα2,3Galβ1,3)GalNAc, Siaα2,3Galβ1,4(Fucα1,3)GlcNAc(6SO$_4$)β1,3Galβ1,3GalNAc, Siaα2,3Galβ1,4(Fucα1,3)GlcNAc(6SO$_4$)β1,3Galβ1,3(Siaα2,3Galβ1,4(Fucα1,3)GlcNAc(6SO$_4$)β1,6)GalNAc, Siaα2,3Gal(6SO$_4$)β1,4GlcNAcβ1,3Galβ1,3GalNAc, Gal(3SO$_4$)β1,3GalNAc(6SO$_4$), Siaα2,3Galβ1,3GalNAc(6SO$_4$), Gal(3SO$_4$)β1,3(Siaα2,6)GalNAc, and Gal(3SO$_4$)β1,3GalNAc, and an oligosaccharide antigen included in a mammal-derived glycosaminoglycan type sugar chain selected from the group consisting of Galβ1,4Xyl, Galβ1,3Galβ1,4Xyl, GlcAβ1,3Galβ1,3Galβ1,4Xyl, GalNAcβ1,4IdoAα1,3Galβ1,3Galβ1,4Xyl, GalNAcβ1,4GlcAβ1,3Galβ1,3Galβ1,4Xyl, GlcNAcα1,4GlcAβ1,3Galβ1,3Galβ1,4Xyl, GlcAβ1,3GalNAcβ1,4GlcA, GalNAcβ1,4GlcAβ1,3GalNAc, GlcAβ1,3GalNAc(4SO₄)β1,4GlcA, GalNAc(4SO₄)β1,4GlcAβ1,3GalNAc, GlcAβ1,3GalNAc(6SO₄)β1,4GlcA, GalNAc(6SO₄)β1,4GlcAβ1,3GalNAc, GlcA(2SO₄)β1,3(6SO₄)GalNAcβ1,4GlcA, GalNAc(6SO₄)β1,4GlcA(2SO₄)β1,3GalNAc, GlcAβ1,3GalNAc(4,6SO₄)β1,4GlcA, GalNAc(4,6SO₄)β1,4GlcAβ1,3GalNAc, GalNAc(4,6SO₄)β1,4GlcA(2SO₄)β1,3GalNAc(6SO₄), IdoAα1,3GalNAcβ1,4IdoA, GalNAcβ1,4IdoAα1,3GalNAc, IdoAα1,3GalNAc(4SO₄)β1,4IdoA, GalNAc(4SO₄)β1,4IdoAα1,3GalNAc, GlcAβ1,4GlcNAcα1,4GlcA, GlcNAcα1,4GlcAβ1,4GlcNAc, GlcA(2SO₄)β1,4GlcNAcα1,4GlcA, GlcNAcα1,4GlcA(2SO₄)β1,4GlcNAc, IdoA(2SO₄)α1,4GlcNAcα1,4GlcA, GlcNAcα1,4IdoA(2SO₄)α1,4GlcNAc, GlcA(2SO₄)β1,4GlcNSO₃α1,4GlcA, GlcNSO₃α1,4GlcA(2SO₄)β1,4GlcNAc, IdoA(2SO₄)α1,4GlcNSO₃Hα1,4GlcA, GlcNSO₃α1,4IdoA(2SO₄)α1,4GlcNAc, GlcAβ1,4GlcNα1,4GlcA, GlcAβ1,4GlcNSO₃α1,4GlcA, GlcNSO₃α1,4GlcAβ1,4GlcNAc, IdoAα1,4GlcNSO₃α1,4GlcA, GlcNSO₃α1,4IdoAα1,4GlcNAc, GlcAβ1,4GlcNSO₃(6SO₄)α1,4GlcA, GlcNSO₃(6SO₄)α1,4GlcAβ1,4GlcNAc, IdoAα1,4GlcNSO₃(6SO₄)α1,4GlcA, GlcNSO₃(6SO₄)α1,4IdoAα1,4GlcNAc, IdoA(2SO₄)α1,4GlcNSO₃(6SO₄)α1,4GlcA, GlcNSO₃(6SO₄)α1,4IdoA(2SO₄)α1,4GlcNAc, IdoAα1,4GlcNSO₃α1,4IdoA, GlcAβ1,3GlcNAcβ1,4GlcA, GlcNAcβ1,4GlcAβ1,3GlcNAc, IdoAα1,4GlcNSO₃, IdoAα1,4GlcNSO₃(6SO₄), IdoA(2SO₄)α1,4GlcNSO₃, IdoA(2SO₄)α1,4GlcNSO₃(6SO₄), IdoA(2SO₄)α1,4GlcNSO₃(3SO₄), GlcAβ1,4GlcNSO₃, GlcAβ1,4GlcNSO₃(6SO₄), GlcA(2SO₄)β1,4GlcNAc, GlcA(2SO₄)β1,4GlcNSO₃(3SO₄), GlcAβ1,4GlcNSO₃(3,6SO₄), and GlcAβ1,4GlcNSO₃(3SO₄)).

2. The immunity inducer according to claim 1, wherein the target oligosaccharide antigen R is an oligosaccharide antigen included in a mammal-derived glycoprotein N-linked sugar chain selected from the group consisting of Siaα2,6Galβ1,4GlcNAc, Siaα2,3Galβ1,4GlcNAc, Galβ1,4GlcNAc, Galβ1,3GlcNAc, Siaα2,3Galβ1,4(Fucα1,3)GlcNAc, Galβ1,4 (Fucα1,3)GlcNAc, Siaα2,3Galβ1,3(Fucα1,4)GlcNAc, Siaα2,3Galβ1,3GlcNAc, Galβ1,3(Fucα1,4)GlcNAc, Siaα2,3Galβ1,3 (Siaα2,6)GlcNAc, Siaα2,3Galβ1,3(Fucα1,4)(Siaα2,6)GlcNAc, Fucα1,2Galβ1,3(Fucα1,4)GlcNAc, Fucα1,2Galβ1,4GlcNAc, Fucα1,2Galβ1,4(Fucα1,3)GlcNAc, Fucα1,6GlcNAc, GlcNAcβ1,4 (Fucα1,6)GlcNAc, Manβ1,4GlcNAcβ1,4(Fucα1,6)GlcNAc, Manα1,6(Manα1,3)Manβ1,4GlcNAcβ1,4(Fucα1,6)GlcNAc, Manα1,6(GlcNAcβ1,4) (Manα1,3)Manβ1,4GlcNAcβ1,4GlcNAc, Manα1,6 (GlcNAcβ1,4) (Manα1,3)Manβ1,4GlcNAcβ1,4(Fucα1,6)GlcNAc, GlcNAcβ1,4GlcNAc, Manβ1,4GlcNAcβ1,4GlcNAc, GlcNAcβ1,2Man, GlcNAcβ1,4Man, GlcNAcβ1,6Man, Galβ1,3GlcNAcβ1,2Man, Galβ1,3GlcNAcβ1,4Man, Galβ1,3GlcNAcβ1,6Man, Galβ1,4GlcNAcβ1,2Man, Galβ1,4GlcNAcβ1,4Man, Galβ1,4GlcNAcβ1,6Man, Siaα2,3Galβ1,4GlcNAcβ1,2Man, Siaα2,3Galβ1,4GlcNAcβ1,4Man, Siaα2,3Galβ1,4GlcNAcβ1,6Man, Siaα2,3Galβ1,3GlcNAcβ1,2Man, Siaα2,3Galβ1,3GlcNAcβ1,4Man, Siaα2,3Galβ1,3GlcNAcβ1,6Man, Siaα2,6Galβ1,4GlcNAcβ1,2Man, Siaα2,6Galβ1,4GlcNAcβ1,4Man, Siaα2,6Galβ1,4GlcNAcβ1,6Man, GalNAcβ1,4GlcNAc, GalNAcβ1,4GlcNAcβ1,2Man, GalNAc(4SO₄)β1,4GlcNAc, GalNAc(4SO₄)β1,4GlcNAcβ1,2Man, GalNAc(4SO₄)β1,4GlcNAcβ1,4Man, GalNAc(4SO₄)β1,6Man, GlcAβ1,3Galβ1,4GlcNAc, GlcA(3SO₄)β1,3Galβ1,4GlcNAc, Siaα2,3Galβ1,4 (Fucα1,3)GlcNAc(6SO₄), Siaα2,3Galβ1,4GlcNAc(6SO₄), Galβ1,4GlcNAc(6SO₄), Galβ1,4(Fucα1,3) GlcNAc(6SO₄), Siaα2,3Gal(6SO₄)β1,4 (Fucα1,3)GlcNAc, Siaα2,3Gal(6SO₄)β1,4GlcNAc, Gal(6SO₄)β1,4GlcNAc, Gal(6SO₄)β1,4GlcNAc(6SO₄), Galβ1,4GlcNAcβ1,3Gal, GlcNAcβ1,3Galβ1,4GlcNAc, Galβ1,4GlcNAc(6SO₄)β1,3Gal, GlcNAc(6SO₄)β1,3Galβ1,4GlcNAc, Gal(6SO₄)β1,4GlcNAc(6SO₄)β1,3Gal, GlcNAc(6SO₄)β1,3Gal(6SO₄)β1,4GlcNAc, Siaα2,3Galβ1,4GlcNAcβ1,3Galβ1,4(Fucα1,3)GlcNAc, Fucα1,2Galβ1,3GlcNAc, Galα1,3(Fucα1,2)Galβ1,3GlcNAc, Galα1,3(Fucα1,2)Galβ1,4GlcNAc, GalNAcα1,3(Fucα1,2)Galβ1,3GlcNAc, GalNAcα1,3(Fucα1,2)Galβ1,4GlcNAc, Fucα1,2Galβ1,4(Fucα1,3)GlcNAcβ1,3Gal, Gal(3SO₄)β1,4GlcNAc, Gal(3SO₄)β1,4(Fucα1,3)GlcNAc, Gal(3SO₄)β1,3GlcNAc, Gal(3SO₄)β1,3(Fucα1,4)GlcNAc, Gal(3SO₄)β1,4GlcNAc(6SO₄), Gal(3SO₄)β1,4(Fucα1,3)GlcNAc(6SO₄), Siaα2,8Siaα2,8Sia, Siaα2,6GalNAcβ1,4GlcNAc, Siaα2,3Galβ1,4(Fucα1,3)GlcNAcβ1,3Galβ1,4(Fucα1,3)GlcNAc, Galβ1,4GlcNAcβ1,3(Galβ1,4GlcNAcβ1,6)Gal, and Siaα2,3Galβ1,4GlcNAcβ1,3(Siaα2,3Galβ1,4GlcNAcβ1,6)Gal.

3. The immunity inducer according to claim 1, wherein the target oligosaccharide antigen R is an oligosaccharide antigen included in a mammal-derived glycoprotein O-linked sugar chain selected from the group consisting of Siaα2,3Galβ1,3GalNAc, Galβ1,3GalNAc, Siaα2,3Galβ1,3(GlcNAcβ1,6)GalNAc, GalNAcα1,3GalNAc, GlcNAcβ1,3(Siaα2,6)GalNAc, GalNAcα1,6GalNAc, GlcNAcβ1,6GalNAc, Fucα1,2GalNAc, Galβ1,3(GlcNAcβ1,6)GalNAc, Siaα2,6GalNAc, Siaα2,6(GlcNAcβ1,6)GalNAc, Siaα2,3Galβ1,3(Siaα2,6)GalNAc, Galβ1,4GalNAc, Siaα2,3Galβ1,4GalNAc, GlcNAcα1,4Gal, GlcNAcα1,4Galβ1,4GlcNAc, GlcNAcα1,4Galβ1,4GalNAc, GlcNAcα1,4Galβ1,4(GlcNAcα1,4Galβ1,4GlcNAcβ1,6)GalNAc, Siaα2,3Galβ1,4(Fucα1,3)GlcNAc(6SO₄)β1,6GalNAc, Gal(3SO₄)β1,4GlcNAcβ1,6(Siaα2,3Galβ1,3)GalNAc, Siaα2,3Galβ1,4(Fucα1,3)GlcNAc(6SO₄)β1,3GalNAc, Siaα2,3Galβ1,4(Fucα1,3)GlcNAc(6SO₄)β1,3Galβ1,3 (Siaα2,3Galβ1,4(Fucα1,3)GlcNAc(6SO₄)β1,6)GalNAc, Siaα2,3Gal(6SO₄) β1,4GlcNAcβ1,3Galβ1,3GalNAc, Gal(3SO₄)β1,3GalNAc(6SO₄), Siaα2,3Galβ1,3GalNAc(6SO₄), Gal(3SO₄)β1,3(Siaα2,6)GalNAc, and Gal(3SO₄)β1,3GalNAc.

4. The immunity inducer according to claim 1, wherein the target oligosaccharide antigen R is an oligosaccharide antigen included in a mammal-derived glycosaminoglycan type sugar chain selected from the group consisting of Galβ1,4Xyl, Galβ1,3Galβ1,4Xyl, GlcAβ1,3Galβ1,3Galβ1,4Xyl, GalNAcβ1,4IdoAα1,3Galβ1,3Galβ1,4Xyl, GalNAcβ1,4GlcAβ1,3Galβ1,3Galβ1,4Xyl, GlcNAcα1,4GlcAβ1,3Galβ1,3Galβ1,4Xyl, GlcAβ1,3GalNAcβ1,4GlcA, GalNAcβ1,4GlcAβ1,3GalNAc, GlcAβ1,3GalNAc (4SO₄)β1,4GlcA, GalNAc(4SO₄)β1,4GlcAβ1,3GalNAc, GlcAβ1,3GalNAc(6SO₄)β1,4GlcA, GalNAc(6SO₄)β1,4GlcAβ1,3GalNAc, GlcA(2SO₄)β1,3(6SO₄)GalNAcβ1,4GlcA, GalNAc(6SO₄)β1,4GlcA(2SO₄)β1,3GalNAc, GlcAβ1,3GalNAc(4,6SO₄)β1,4GlcA, GalNAc(4,6SO₄)β1,4GlcAβ1,3GalNAc, GalNAc(4,6SO₄)β1,4GlcA(2SO₄)β1,3GalNAc(6SO₄), IdoAα1,3GalNAcβ1,4IdoA, GalNAcβ1,4IdoAα1,3GalNAc, IdoAα1,3GalNAc(4SO₄)β1,4IdoA, GalNAc(4SO₄)β1,4IdoAα1,3GalNAc, GlcAβ1,4GlcNAcα1,4GlcA, GlcNAcα1,4GlcAβ1,4GlcNAc, GlcA(2SO₄)β1,4GlcNAcα1,4GlcA, GlcNAcα1,4GlcA(2SO₄)β1,4GlcNAc, IdoA(2SO₄)α1,4GlcNAcα1,4GlcA, GlcNAcα1,4IdoA(2SO₄)α1,4GlcNAc, GlcA(2SO₄)β1,4GlcNSO₃α1, 4GlcA, GlcNSO₃α1,4GlcA(2SO₄)β1,4GlcNAc, IdoA(2SO₄)α1,4GlcNSO₃Hα1,4GlcA, GlcNSO₃α1,4IdoA(2SO₄)α1,4GlcNAc, GlcAβ1,4GlcNα1,4GlcA, GlcAβ1,4GlcNSO₃α1,4GlcA, GlcNSO₃α1,4GlcAβ1,4GlcNAc, IdoAα1,4GlcNSO₃α1,4GlcA, GlcNSO₃α1,4IdoAα1,4GlcNAc, GlcAβ1,4GlcNSO₃(6SO₄)α1,4GlcA, GlcNSO₃(6SO₄)α1,4GlcAβ1,4GlcNAc, IdoAα1,4GlcNSO₃(6SO₄)α1,4GlcA, GlcNSO₃(6SO₄)α1,4IdoAα1,4GlcNAc, IdoA(2SO₄)α1,4GlcNSO₃(6SO₄)α1,4GlcA, GlcNSO₃(6SO₄)α1,4IdoA(2SO₄)α1,4GlcNAc, IdoAα1,4GlcNSO₃α1,4IdoA, GlcAβ1,3GlcNAcβ1,4GlcA, GlcNAcβ1,4GlcAβ1,3GlcNAc, IdoAα1,4GlcNSO₃, IdoAα1,4GlcNSO₃(6SO₄), IdoA(2SO₄)α1,4GlcNSO₃, IdoA(2SO₄)α1,4GlcNSO₃(6SO₄), IdoA(2SO₄)α1,4GlcNSO₃(3SO₄), GlcAβ1,4GlcNSO₃, GlcAβ1,4GlcNSO₃(6SO₄), GlcA(2SO₄)β1,4GlcNAc, GlcA(2SO₄)β1,4GlcNSO₃(3SO₄), GlcAβ1,4GlcNSO₃(3,6SO₄), and GlcAβ1,4GlcNSO₃(3SO₄).

5. An artificial glycolipid having chemical formula (2) or a salt thereof:

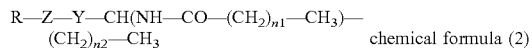
$$R-Z-Y-CH(NH-CO-(CH_2)_{n1}-CH_3)-(CH_2)_{n2}-CH_3 \qquad \text{chemical formula (2)}$$

wherein, in the chemical formula (2), R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —$(CH_2)_m$—, n1 represents an integer from 20 to 40, n2 represents an integer from 1 to 27, and m represents an integer from 1 to 30, and wherein R is an oligosaccharide antigen selected from the group consisting of an oligosaccharide antigen included in a mammal-derived glycoprotein N-linked sugar chain selected from the group consisting of Siaα2,6Galβ1,4GlcNAc, Siaα2,3Galβ1,4GlcNAc, Galβ1,4GlcNAc, Galβ1,3GlcNAc, Siaα2,3Galβ1,4(Fucα1,3)GlcNAc, Galβ1,4 (Fucα1,3)GlcNAc, Siaα2,3Galβ1,3(Fucα1,4)GlcNAc, Siaα2,3Galβ1,3GlcNAc, Galβ1,3(Fucα1,4)GlcNAc, Siaα2,3Galβ1,3 (Siaα2,6)GlcNAc, Siaα2,3Galβ1,3 (Fucα1,4)(Siaα2,6)GlcNAc, Fucα1,2Galβ1,3(Fucα1,4)GlcNAc, Fucα1,2Galβ1,4GlcNAc, Fucα1,2Galβ1,4(Fucα1,3)GlcNAc, Fucα1,6GlcNAc, GlcNAcβ1,4(Fucα1,6)GlcNAc, Manβ1,4GlcNAcβ1,4(Fucα1,6)GlcNAc, Manα1,6(Manα1,3)Manβ1,4GlcNAcβ1,4(Fucα1,6)GlcNAc, Manα1,6 (GlcNAcβ1,4)(Manα1,3)Manβ1,4GlcNAcβ1,4GlcNAc, Manα1,6 (GlcNAcβ1,4) (Manα1,3)Manβ1,4GlcNAcβ1,4(Fucα1,6)GlcNAc, GlcNAcβ1,4GlcNAc, Manβ1,4GlcNAcβ1,4 GlcNAc, GlcNAcβ1,2Man, GlcNAcβ1,4Man, GlcNAcβ1,6Man, Galβ1,3GlcNAcβ1,2Man, Galβ1,3GlcNAcβ1,4Man, Galβ1,3GlcNAcβ1,6Man, Galβ1,4GlcNAcβ1,2Man, Galβ1,4GlcNAcβ1,4Man, Galβ1,4GlcNAcβ1,6Man, Siaα2,3Galβ1,4GlcNAcβ1,2Man, Siaα2,3Galβ1,4GlcNAcβ1,4Man, Siaα2,3Galβ1,4GlcNAcβ1,6Man, Siaα2,3Galβ1,3GlcNAcβ1,2Man, Siaα2,3Galβ1,3GlcNAcβ1,4Man, Siaα2,3Galβ1,3GlcNAcβ1,6Man, Siaα2,6Galβ1,4GlcNAcβ1,2Man, Siaα2,6Galβ1,4GlcNAcβ1,4Man, Siaα2,6Galβ1,4GlcNAcβ1,6Man, GalNAcβ1,4GlcNAc, GalNAcβ1,4GlcNAc, GalNAcβ1,4GlcNAc, GalNAc(4SO₄)β1,4GlcNAc, GalNAc(4SO₄)β1,4GlcNAcβ1,2Man, GalNAc(4SO₄)β1,4GlcNAcβ1,4Man, GalNAc(4SO₄)β1,4GlcNAcβ1,6Man, GlcAβ1,3Galβ1,4GlcNAc, GlcA(3SO₄)β1,3Galβ1,4GlcNAc, Siaα2,3Galβ1,4(Fucα1,3)GlcNAc(6SO₄), Siaα2,3Galβ1,4GlcNAc(6SO₄), Galβ1,4GlcNAc(6SO₄), Galβ1,4(Fucα1,3)GlcNAc(6SO₄), Siaα2,3Gal(6SO₄)β1,4(Fucα1,3)GlcNAc, Siaα2,3Gal(6SO₄)β1,4GlcNAc, Gal(6SO₄)β1,4GlcNAc, Gal(6SO₄)β1,4GlcNAc(6SO₄), Galβ1,4GlcNAcβ1,3Gal, GlcNAcβ1,3Galβ1,4GlcNAc, Galβ1,4GlcNAc(6SO₄)β1,3Gal, GlcNAc(6SO₄)β1,3Galβ1,4GlcNAc, Gal(6SO₄)β1,4GlcNAc(6SO₄)β1,3Gal, GlcNAc(6SO₄)β1,3Gal(6SO₄)β1,4GlcNAc, Siaα2,3Galβ1,4GlcNAcβ1,3Galβ1,4(Fucα1,3)GlcNAc, Fucα1,2Galβ1,3GlcNAc, Galα1,3(Fucα1,2)Galβ1,3GlcNAc, Galα1,3(Fucα1,2)Galβ1,4GlcNAc, GalNAcα1,3(Fucα1,2)Galβ1,3GlcNAc, GalNAcα1,3(Fucα1,2)Galβ1,4GlcNAc, Fucα1,2Galβ1,4(Fucα1,3)GlcNAcβ1,3Gal, Gal(3SO₄)β1,4GlcNAc, Gal(3SO₄)β1,4(Fucα1,3)GlcNAc, Gal(3SO₄)β1,3GlcNAc, Gal(3SO₄)β1,3(Fucα1,4)GlcNAc, Gal(3SO₄)β1,4GlcNAc(6SO₄), Gal(3SO₄)β1,4(Fucα1,3)GlcNAc(6SO₄), Siaα2,8Siaα2,8Sia, Siaα2,6GalNAcβ1,4GlcNAc, Siaα2,3Galβ1,4(Fucα1,3)GlcNAcβ1,3Galβ1,4(Fucα1,3)GlcNAc, Galβ1,4GlcNAcβ1,3(Galβ1,4GlcNAcβ1,6)Gal, and Siaα2,3Galβ1,4GlcNAcβ1,3(Siaα2,3Galβ1,4GlcNAcβ1,6)Gal, an oligosaccharide antigen included in a mammal-derived glycoprotein O-linked sugar chain selected from the group consisting of Siaα2,3Galβ1,3GalNAc, Galβ1,3GalNAc, Siaα2,3Galβ1,3(GlcNAcβ1,6)GalNAc, GalNAcα1,3GalNAc, GlcNAcβ1,3(Siaα2,6)GalNAc, GalNAcα1,6GalNAc, GlcNAcβ1,6GalNAc, Fucα1,2GalNAc, Galβ1,3(GlcNAcβ1,6)GalNAc, Siaα2,6GalNAc, Siaα2,6(GlcNAcβ1,6)GalNAc, Siaα2,3Galβ1,3(Siaα2,6)GalNAc, Galβ1,4GalNAc, Siaα2,3Galβ1,4GalNAc, GlcNAcα1,4Gal, GlcNAcα1,4Galβ1,4GlcNAc, GlcNAcα1,4Galβ1,4GalNAc, GlcNAcα1,4Galβ1,4(GlcNAcα1,4Galβ1,4GlcNAcβ1,6)GalNAc, Siaα2,3Galβ1,4(Fucα1,3)GlcNAc(6SO₄)β1,6GalNAc, Gal(3SO₄)β1,4GlcNAcβ1,6(Siaα2,3Galβ1,3)GalNAc, Siaα2,3Galβ1,4(Fucα1,3)GlcNAc(6SO₄)β1,3Galβ1,3GalNAc, Siaα2,3Galβ1,4(Fucα1,3)GlcNAc(6SO₄)β1,3Galβ1,3(Siaα2,3Galβ1,4(Fucα1,3)GlcNAc(6SO₄)β1,6)GalNAc, Siaα2,3Gal(6SO₄)β1,4GlcNAcβ1,3Galβ1,3GalNAc, Gal(3SO₄)β1,3GalNAc(6SO₄), Siaα2,3Galβ1,3GalNAc(6SO₄), Gal(3SO₄)β1,3(Siaα2,6)GalNAc, and Gal(3SO₄)β1,3GalNAc, and an oligosaccharide antigen included in a mammal-derived glycosaminoglycan type sugar chain selected from the group consisting of Galβ1,4Xyl, Galβ1,3Galβ1,4Xyl, GlcAβ1,3Galβ1,3Galβ1,4Xyl, GalNAcβ1,4IdoAα1,3Galβ1,3Galβ1,4Xyl, GalNAcβ1,4GlcAβ1,3Galβ1,3Galβ1,4Xyl, GlcNAcα1,4GlcAβ1,3Galβ1,3Galβ1,4Xyl, GlcAβ1,3GalNAcβ1,4GlcA, GalNAcβ1,4GlcAβ1,3GalNAc, GlcAβ1,3GalNAc(4SO₄)β1,4GlcA, GalNAc(4SO₄)β1,4 GlcAβ1,3GalNAc, GlcAβ1,3GalNAc(6SO₄)β1,4GlcA, GalNAc(6SO₄)β1,4 GlcAβ1,3GalNAc, GlcA(2SO₄)β1,3(6SO₄)GalNAcβ1,4GlcA, GalNAc(6SO₄)β1,4GlcA(2SO₄)β1,3GalNAc, GlcAβ1,3GalNAc(4,6SO₄)β1,4GlcA, GalNAc(4,6SO₄)β1,4GlcAβ1,3GalNAc, GalNAc(4,6SO₄)β1,4GlcA(2SO₄)β1,3GalNAc(6SO₄), IdoAα1,3GalNAcβ1,4IdoA, GalNAcβ1,4IdoAα1,3GalNAc, IdoAα1,3GalNAc(4SO₄)β1,4IdoA, GalNAc(4SO₄)β1,4IdoAα1,3GalNAc, GlcAβ1, 4GlcNAcα1,4GlcA, GlcNAcα1,4GlcAβ1, 4GlcNAc, GlcA(2SO$_4$)β1,4GlcNAcα1,4GlcA, GlcNAcα1,4GlcA(2SO$_4$)β1,4GlcNAc, IdoA(2SO$_4$) α1,4GlcNAcα1,4GlcA, GlcNAcα1,4IdoA(2SO$_4$) α1,4GlcNAc, GlcA(2SO$_4$)β1,4GlcNSO$_3$α1,4GlcA, GlcNSO$_3$α1,4GlcA(2SO$_4$)β1,4GlcNAc, IdoA (2SO$_4$)α1,4GlcNSO$_3$Hα1,4GlcA, GlcNSO$_3$α1, 4IdoA(2SO$_4$)α1,4GlcNAc, GlcAβ1,4GlcNα1, 4GlcA, GlcAβ1,4GlcNSO$_3$α1,4GlcA, GlcNSO$_3$α1, 4GlcAβ1,4GlcNAc, IdoAα1,4GlcNSO$_3$α1,4GlcA, GlcNSO$_3$α1,4IdoAα1,4GlcNAc, GlcAβ1,4GlcNSO$_3$(6SO$_4$)α1,4GlcA, GlcNSO$_3$(6SO$_4$)α1, 4GlcAβ1,4GlcNAc, IdoAα1,4GlcNSO$_3$(6SO$_4$)α1, 4GlcA, GlcNSO$_3$(6SO$_4$)α1,4IdoAα1,4GlcNAc, IdoA(2SO$_4$)α1,4GlcNSO$_3$(6SO$_4$)α1,4GlcA, GlcNSO$_3$(6SO$_4$)α1,4IdoA(2SO$_4$)α1,4GlcNAc, IdoAα1,4 GlcNSO$_3$α1,4IdoA, GlcAβ1,3GlcNAcβ1, 4GlcA, GlcNAcβ1,4GlcAβ1,3GlcNAc, IdoAα1, 4GlcNSO$_3$, IdoAα1,4GlcNSO$_3$(6SO$_4$), IdoA(2SO$_4$) α1,4GlcNSO$_3$, IdoA(2SO$_4$)α1,4GlcNSO$_3$(6SO$_4$), IdoA(2SO$_4$)α1,4GlcNSO$_3$(3SO$_4$), GlcAβ1,4GlcNSO$_3$, GlcAβ1,4GlcNSO$_3$(6SO$_4$), GlcA(2SO$_4$)β1, 4GlcNAc, GlcA(2SO$_4$)β1,4GlcNSO$_4$(3SO$_4$), GlcAβ1,4GlcNSO$_3$(3,6SO$_4$), and GlcAβ1,4GlcNSO$_3$(3SO$_4$).

6. The glycolipid or the salt thereof according to claim 5, wherein R is an oligosaccharide antigen included in a mammal-derived glycoprotein N-linked sugar chain selected from the group consisting of Siaα2,6Galβ1,4GlcNAc, Siaα2,3Galβ1,4GlcNAc, Galβ1,4GlcNAc, Galβ1,3GlcNAc, Siaα2,3Galβ1,4(Fucα1,3)GlcNAc, Galβ1,4 (Fucα1, 3)GlcNAc, Siaα2,3Galβ1,3(Fucα1,4)GlcNAc, Siaα2, 3Galβ1,3GlcNAc, Galβ1,3(Fucα1,4)GlcNAc, Siaα2, 3Galβ1,3 (Siaα2,6GlcNAc, Siaα2,3Galβ1,3 (Fucα1,4) (Siaα2,6)GlcNAc, Fucα1,2Galβ1,3(Fucα1,4)GlcNAc, Fucα1,2Galβ1,4GlcNAc, Fucα1,2Galβ1,4(Fucα1,3)GlcNAc, Fucα1,6GlcNAc, GlcNAcβ1,4 (Fucα1,6)GlcNAc, Manβ1,4GlcNAcβ1,4(Fucα1,6)GlcNAc, Manα1,6(Manα1, 3)Manβ1,4GlcNAcβ1,4(Fucα1,6)GlcNAc, Manα1,6 (GlcNAcβ1,4) (Manα1,3)Manβ1,4GlcNAcβ1,4GlcNAc, Manα1,6 (GlcNAcβ1,4) (Manα1,3)Manβ1,4GlcNAcβ1,4 (Fucα1,6)GlcNAc, GlcNAcβ1,4GlcNAc, Manβ1, 4GlcNAcβ1,4GlcNAc, GlcNAcβ1,2Man, GlcNAcβ1, 4Man, GlcNAcβ1,6Man, Galβ1,3GlcNAcβ1,2Man, Galβ1, 3GlcNAcβ1,4Man, Galβ1,3GlcNAcβ1,6Man, Galβ1, 4GlcNAcβ1,2Man, Galβ1,4GlcNAcβ1,4Man, Galβ1, 4GlcNAcβ1,6Man, Siaα2,3Galβ1,4GlcNAcβ1,2Man, Siaα2,3Galβ1,4GlcNAcβ1,4Man, Siaα2,3Galβ1, 4GlcNAcβ1,6Man, Siaα2,3Galβ1,3GlcNAcβ1,2Man, Siaα2,3Galβ1,3GlcNAcβ1,4Man, Siaα2,3Galβ1, 3GlcNAcβ1,6Man, Siaα2,6Galβ1,4GlcNAcβ1,2Man, Siaα2,6Galβ1,4GlcNAcβ1,4Man, Siaα2,6Galβ1, 4GlcNAcβ1,6Man, GalNAcβ1,4GlcNAc, GalNAcβ1, 4GlcNAcβ1,2Man, GalNAc(4SO$_4$)β1,4GlcNAc, GalNAc (4SO$_4$)β1,4GlcNAcβ1,2Man, GalNAc(4SO$_4$)β1, 4GlcNAcβ1,4Man, GalNAc(4SO$_4$)β1,4GlcNAcβ1,6Man, GlcAβ1,3Galβ1,4GlcNAc, GlcA(3SO$_4$)β1,3Galβ1,4GlcNAc, Siaα2,3Galβ1,4(Fucα1,3)GlcNAc(6SO$_4$), Siaα2, 3Galβ1,4GlcNAc(6SO$_4$), Galβ1,4GlcNAc(6SO$_4$), Galβ1,4 (Fucα1,3) GlcNAc(6SO$_4$), Siaα2,3Gal(6SO$_4$)β1,4(Fucα1, 3)GlcNAc, Siaα2,3Gal(6SO$_4$)β1,4GlcNAc, Gal(6SO$_4$)β1, 4GlcNAc, Gal(6SO$_4$)β1,4GlcNAc(6SO$_4$), Galβ1, 4GlcNAcβ1,3Gal, GlcNAcβ1,3Galβ1,4GlcNAc, Galβ1, 4GlcNAc(6SO$_4$)β1,3Gal, GlcNAc(6SO$_4$)β1,3Galβ1, 4GlcNAc, Gal(6SO$_4$)β1,4GlcNAc(6SO$_4$)β1,3Gal, GlcNAc (6SO$_4$)β1,3Gal(6SO$_4$)β1,4GlcNAc, Siaα2,3Galβ1, 4GlcNAcβ1,3Galβ1,4(Fucα1,3)GlcNAc, Fucα1,2Galβ1, 3GlcNAc, Galα1,3(Fucα1,2)Galβ1,3GlcNAc, Galα1,3 (Fucα1,2)Galβ1,4GlcNAc, GalNAcα1,3(Fucα1,2)Galβ1, 3GlcNAc, GalNAcα1,3(Fucα1,2)Galβ1,4GlcNAc, Fucα1, 2Galβ1,4(Fucα1,3)GlcNAcβ1,3Gal, Gal(3SO$_4$)β1, 4GlcNAc, Gal(3SO$_4$)β1,4(Fucα1,3)GlcNAc, Gal(3SO$_4$)β1, 3GlcNAc, Gal(3SO$_4$)β1,3(Fucα1,4)GlcNAc, Gal(3SO$_4$)β1, 4GlcNAc(6SO$_4$), Gal(3SO$_4$)β1,4(Fucα1,3)GlcNAc(6SO$_4$), Siaα2,8Siaα2,8Sia, Siaα2,6GalNAcβ1,4GlcNAc, Siaα2, 3Galβ1,4(Fucα1,3)GlcNAcβ1,3Galβ1,4(Fucα1,3)GlcNAc, Galβ1,4GlcNAcβ1,3(Galβ1,4GlcNAcβ1,6)Gal, and Siaα2, 3Galβ1,4GlcNAcβ1,3(Siaα2,3Galβ1,4GlcNAcβ1,6)Gal.

7. The glycolipid or the salt thereof according to claim 5, wherein R is an oligosaccharide antigen included in a mammal-derived glycoprotein O-linked sugar chain selected from the group consisting of Siaα2,3Galβ1,3GalNAc, Galβ1,3GalNAc, Siaα2,3Galβ1,3(GlcNAcβ1,6)GalNAc, GalNAcα1,3GalNAc, GlcNAcβ1,3(Siaα2,6)GalNAc, GalNAcα1,6GalNAc, GlcNAcβ1,6GalNAc, Fucα1,2GalNAc, Galβ1,3(GlcNAcβ1,6)GalNAc, Siaα2,6GalNAc, Siaα2,6(GlcNAcβ1,6)GalNAc, Siaα2,3Galβ1,3(Siaα2,6) GalNAc, Galβ1,4GalNAc, Siaα2,3Galβ1,4GalNAc, GlcNAcα1,4Gal, GlcNAcα1,4Galβ1,4GlcNAc, GlcNAcα1,4Galβ1,4GalNAc, GlcNAcα1,4Galβ1,4 (GlcNAcα1,4Galβ1,4GlcNAcβ1,6)GalNAc, Siaα2,3Galβ1, 4(Fucα1,3)GlcNAc(6SO$_4$)β1,6GalNAc, Galβ SO$_4$)β1, 4GlcNAcβ1,6(Siaα2,3Galβ1,3)GalNAc, Siaα2,3Galβ1,4 (Fucα1,3)GlcNAc(6SO$_4$)β1,3Galβ1,3GalNAc, Siaα2, 3Galβ1,4(Fucα1,3)GlcNAc(6SO$_4$)β1,3Galβ1,3(Siaα2, 3Galβ1,4(Fucα1,3)GlcNAc(6SO$_4$)β1,6)GalNAc, Siaα2, 3Gal(6SO$_4$) β1,4GlcNAcβ1,3Galβ1,3GalNAc, Gal(3SO$_4$) β1,3GalNAc(6SO$_4$), Siaα2,3Galβ1,3GalNAc(6SO$_4$), Gal (3SO$_4$)β1,3(Siaα2,6)GalNAc, and Gal(3SO$_4$)β1,3GalNAc.

8. The glycolipid or the salt thereof according to claim 5, wherein R is an oligosaccharide antigen included in a mammal-derived glycosaminoglycan type sugar chain selected from the group consisting of Galβ1,4Xyl, Galβ1, 3Galβ1,4Xyl, GlcAβ1,3Galβ1,3Galβ1,4Xyl, GalNAcβ1, 4IdoAα1,3Galβ1,3Galβ1,4Xyl, GalNAcβ1,4GlcAβ1, 3Galβ1,3Galβ1,4Xyl, GlcNAcα1,4GlcAβ1,3Galβ1, 3Galβ1,4Xyl, GlcAβ1,3GalNAcβ1,4GlcA, GalNAcβ1, 4GlcAβ1,3GalNAc, GlcAβ1,3GalNAc(4SO$_4$)β1,4GlcA, GalNAc(4SO$_4$)β1,4 GlcAβ1,3GalNAc, GlcAβ1,3GalNAc (6SO$_4$)β1,4GlcA, GalNAc(6SO$_4$)β1,4GlcAβ1,3GalNAc, GlcA(2SO$_4$)β1,3(6SO$_4$)GalNAcβ1,4GlcA, GalNAc(6SO$_4$) β1,4GlcA(2SO$_4$)β1,3GalNAc, GlcAβ1,3GalNAc(4,6SO$_4$) β1,4GlcA, GalNAc(4,6SO$_4$)β1,4GlcAβ1,3GalNAc, GalNAc(4,6SO$_4$)β1,4GlcA(2SO$_4$)β1,3GalNAc(6SO$_4$), IdoAα1,3GalNAcβ1,4IdoA, GalNAcβ1,4IdoAα1,3GalNAc, IdoAα1,3GalNAc(4SO$_4$)β1,4IdoA, GalNAc(4SO$_4$) β1,4IdoAα1,3GalNAc, GlcAβ1,4GlcNAcα1,4GlcA, GlcNAcα1,4GlcAβ1,4GlcNAc, GlcA(2SO$_4$)β1, 4GlcNAcα1,4GlcA, GlcNAcα1,4GlcA(2SO$_4$)β1,4GlcNAc, IdoA(2SO$_4$)α1,4GlcNAcα1,4GlcA, GlcNAcα1,4IdoA (2SO$_4$)α1,4GlcNAc, GlcA(2SO$_4$)β1,4GlcNSO$_3$α1,4GlcA, GlcNSO$_3$α1,4GlcA(2SO$_4$)β1,4GlcNAc, IdoA(2SO$_4$)α1, 4GlcNSO$_3$Hα1,4GlcA, GlcNSO$_3$α1,4IdoA(2SO$_4$)α1,4GlcNAc, GlcAβ1,4GlcNα1,4GlcA, GlcAβ1,4GlcNSO$_3$α1, 4GlcA, GlcNSO$_3$α1,4GlcAβ1,4GlcNAc, IdoAα1, 4GlcNSO$_3$α1,4GlcA, GlcNSO$_3$α1,4IdoAα1,4GlcNAc, GlcAβ1,4GlcNSO$_3$(6SO$_4$)α1,4GlcA, GlcNSO$_3$(6SO$_4$)α1, 4GlcAβ1,4GlcNAc, IdoAα1,4GlcNSO$_3$(6SO$_4$)α1,4GlcA, GlcNSO$_3$(6SO$_4$)α1,4IdoAα1,4GlcNAc, IdoA(2SO$_4$)α1, 4GlcNSO$_3$(6SO$_4$)α1,4GlcA, GlcNSO$_3$(6SO$_4$)α1,4IdoA (2SO$_4$)α1,4GlcNAc, IdoAα1,4 GlcNSO$_3$α1,4IdoA, GlcAβ1,3GlcNAcβ1,4GlcA, GlcNAcβ1,4GlcAβ1,3GlcNAc, IdoAα1,4GlcNSO$_3$, IdoAα1,4GlcNSO$_3$(6SO$_4$), IdoA (2SO$_4$)α1,4GlcNSO$_3$, IdoA(2SO$_4$)α1,4GlcNSO$_3$(6SO$_4$), IdoA(2SO₄)α1,4GlcNSO₃(3SO₄), GlcAβ1,4GlcNSO₃, GlcAβ1,4GlcNSO₃(6SO₄), GlcA(2SO₄)β1,4GlcNAc, GlcA (2SO₄)β1,4GlcNSO₃(3SO₄), GlcAβ1,4GlcNSO₃(3,6SO₄), and GlcAβ1,4GlcNSO₃(3SO₄).

9. A vaccine comprising an artificial glycolipid or a salt thereof as an effective component, wherein the artificial glycolipid has the chemical formula (2) and includes the target oligosaccharide antigen R:

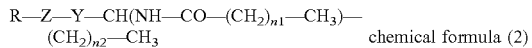    chemical formula (2)

wherein, in the chemical formula (2), R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —(CH$_2$)$_m$—, n1 represents an integer from 2 to 40, n2 represents an integer from 1 to 27, and m represents an integer from 1 to 30, and wherein the target oligosaccharide antigen R is selected from the group consisting of an oligosaccharide antigen included in a mammal-derived glycoprotein N-linked sugar chain, an oligosaccharide antigen included in a mammal-derived glycoprotein O-linked sugar chain, and an oligosaccharide antigen included in a mammal-derived glycosaminoglycan type sugar chain.

10. The vaccine according to claim 9, wherein the target oligosaccharide antigen R is an oligosaccharide antigen included in a mammal-derived glycoprotein N-linked sugar chain selected from the group consisting of Siaα2,6Galβ1,4GlcNAc, Siaα2,3Galβ1,4GlcNAc, Galβ1,4GlcNAc, Galβ1,3GlcNAc, Siaα2,3Galβ1,4(Fucα1,3)GlcNAc, Galβ1,4 (Fucα1,3)GlcNAc, Siaα2,3Galβ1,3(Fucα1,4)GlcNAc, Siaα2,3Galβ1,3GlcNAc, Galβ1,3(Fucα1,4)GlcNAc, Siaα2,3Galβ1,3 (Siaα2,6)GlcNAc, Siaα2,3Galβ1,3(Fucα1,4)(Siaα2,6)GlcNAc, Fucα1,2Galβ1,3(Fucα1,4)GlcNAc, Fucα1,2Galβ1,4GlcNAc, Fucα1,2Galβ1,4(Fucα1,3)GlcNAc, Fucα1,6GlcNAc, GlcNAcβ1,4 (Fucα1,6)GlcNAc, Manβ1,4GlcNAcβ1,4(Fucα1,6)GlcNAc, Manα1,6(Manα1,3)Manβ1,4GlcNAcβ1,4(Fucα1,6)GlcNAc, Manα1,6(GlcNAcβ1,4) (Manα1,3)Manβ1,4GlcNAcβ1,4GlcNAc, Manα1,6(GlcNAcβ1,4) (Manα1,3)Manβ1,4GlcNAcβ1,4(Fucα1,6)GlcNAc, GlcNAcβ1,4GlcNAc, Manβ1,4GlcNAcβ1,4GlcNAc, GlcNAcβ1,2Man, GlcNAcβ1,4Man, GlcNAcβ1,6Man, Galβ1,3GlcNAcβ1,2Man, Galβ1,3GlcNAcβ1,4Man, Galβ1,3GlcNAcβ1,6Man, Galβ1,4GlcNAcβ1,2Man, Galβ1,4GlcNAcβ1,4Man, Galβ1,4GlcNAcβ1,6Man, Siaα2,3Galβ1,4GlcNAcβ1,2Man, Siaα2,3Galβ1,4GlcNAcβ1,4Man, Siaα2,3Galβ1,4GlcNAcβ1,6Man, Siaα2,3Galβ1,3GlcNAcβ1,2Man, Siaα2,3Galβ1,3GlcNAcβ1,4Man, Siaα2,3Galβ1,3GlcNAcβ1,6Man, Siaα2,6Galβ1,4GlcNAcβ1,2Man, Siaα2,6Galβ1,4GlcNAcβ1,4Man, Siaα2,6Galβ1,4GlcNAcβ1,6Man, GalNAcβ1,4GlcNAc, GalNAcβ1,4GlcNAcβ1,2Man, GalNAc(4SO₄)β1,4GlcNAc, GalNAc(4SO₄)β1,4GlcNAcβ1,2Man, GalNAc(4SO₄)β1,4GlcNAcβ1,4Man, GalNAc(4SO₄)β1,4GlcNAcβ1,6Man, GlcAβ1,3Galβ1,4GlcNAc, GlcA(3SO₄)β1,3Galβ1,4GlcNAc, Siaα2,3Galβ1,4 (Fucα1,3)GlcNAc(6SO₄), Siaα2,3Galβ1,4GlcNAc(6SO₄), Galβ1,4 GlcNAc(6SO₄), Galβ1,4 (Fucα1,3) GlcNAc(6SO₄), Siaα2,3Gal(6SO₄)β1,4 (Fucα1,3)GlcNAc, Siaα2,3Gal(6SO₄)β1,4GlcNAc, Gal(6SO₄)β1,4GlcNAc, Gal(6SO₄)β1,4GlcNAc(6SO₄), Galβ1,4GlcNAcβ1,3Gal, GlcNAcβ1,3Galβ1,4GlcNAc, GlcNAc(6SO₄)β1,3Gal, GlcNAc(6SO₄)β1,3Galβ1,4GlcNAc, Gal(6SO₄)β1,4GlcNAc(6SO₄)β1,3Gal, GlcNAc (6SO₄)β1,3Gal(6SO₄)β1,4GlcNAc, Siaα2,3Galβ1,4GlcNAcβ1,3Galβ1,4(Fucα1,3)GlcNAc, Fucα1,2Galβ1,3GlcNAc, Galα1,3(Fucα1,2)Galβ1,3GlcNAc, Galα1,3(Fucα1,2)Galβ1,4GlcNAc, GalNAcα1,3(Fucα1,2)Galβ1,3GlcNAc, GalNAcα1,3(Fucα1,2)Galβ1,4GlcNAc, Fucα1,2Galβ1,4(Fucα1,3)GlcNAcβ1,3Gal, Gal(3SO₄)β1,4GlcNAc, Gal(3SO₄)β1,4(Fucα1,3)GlcNAc, Gal(3SO₄)β1,3GlcNAc, Gal(3SO₄)β1,3(Fucα1,4)GlcNAc, Gal(3SO₄)β1,4GlcNAc(6SO₄), Gal(3SO₄)β1,4(Fucα1,3)GlcNAc(6SO₄), Siaα2,8Siaα2,8Sia, Siaα2,6GalNAcβ1,4GlcNAc, Siaα2,3Galβ1,4(Fucα1,3)GlcNAcβ1,3Galβ1,4(Fucα1,3)GlcNAc, Galβ1,4GlcNAcβ1,3(Galβ1,4GlcNAcβ1,6)Gal, and Siaα2,3Galβ1,4GlcNAcβ1,3(Siaα2,3Galβ1,4GlcNAcβ1,6)Gal.

11. The vaccine according to claim 9, wherein the target oligosaccharide antigen R is an oligosaccharide antigen included in a mammal-derived glycoprotein O-linked sugar chain selected from the group consisting of Siaα2,3Galβ1,3GalNAc, Galβ1,3GalNAc, Siaα2,3Galβ1,3(GlcNAcβ1,6)GalNAc, GalNAcα1,3GalNAc, GlcNAcβ1,3(Siaα2,6)GalNAc, GalNAcα1,6GalNAc, GlcNAcβ1,6GalNAc, Fucα1,2GalNAc, Galβ1,3(GlcNAcβ1,6)GalNAc, Siaα2,6GalNAc, Siaα2,6(GlcNAcβ1,6)GalNAc, Siaα2,3Galβ1,3(Siaα2,6)GalNAc, Galβ1,4GalNAc, Siaα2,3Galβ1,4GalNAc, GlcNAcα1,4Gal, GlcNAcα1,4Galβ1,4GlcNAc, GlcNAcα1,4Galβ1,4GalNAc, GlcNAcα1,4Galβ1,4 (GlcNAcα1,4Galβ1,4GlcNAcβ1,6)GalNAc, Siaα2,3Galβ1,4(Fucα1,3)GlcNAc(6SO₄)β1,6GalNAc, Galβ(SO₄)β1,4GlcNAcβ1,6(Siaα2,3Galβ1,3)GalNAc, Siaα2,3Galβ1,4(Fucα1,3)GlcNAc(6SO₄)β1,3Galβ1,3GalNAc, Siaα2,3Galβ1,4(Fucα1,3)GlcNAc(6SO₄)β1,3Galβ1,3(Siaα2, 3Galβ1,4(Fucα1,3)GlcNAc(6SO₄)β1,6)GalNAc, Siaα2,3Gal(6SO₄)β1,4GlcNAcβ1,3Galβ1,3GalNAc, Gal(3SO₄)β1,3GalNAc(6SO₄), Siaα2,3Galβ1,3GalNAc(6SO₄), Gal (3SO₄)β1,3(Siaα2,6)GalNAc, and Gal(3SO₄)β1,3GalNAc.

12. The vaccine according to claim 9, wherein the target oligosaccharide antigen R is an oligosaccharide antigen included in a mammal-derived glycosaminoglycan type sugar chain selected from the group consisting of Galβ1,4Xyl, Galβ1,3Galβ1,4Xyl, GlcAβ1,3Galβ1,3Galβ1,4Xyl, GalNAcβ1,4IdoAα1,3Galβ1,3Galβ1,4Xyl, GalNAcβ1,4GlcAβ1,3Galβ1,3Galβ1,4Xyl, GlcNAcα1,4GlcAβ1,3Galβ1,3Galβ1,4Xyl, GlcAβ1,3GalNAcβ1,4GlcA, GalNAcβ1,4GlcAβ1,3GalNAc, GlcAβ1,3GalNAc(4SO₄)β1,4GlcA, GalNAc(4SO₄)β1,4GlcAβ1,3GalNAc, GlcAβ1,3GalNAc(6SO₄)β1,4GlcA, GalNAc(6SO₄)β1,4GlcAβ1,3GalNAc, GlcA(2SO₄)β1,3(6SO₄)GalNAcβ1,4GlcA, GalNAc(6SO₄)β1,4GlcA(2SO₄)β1,3GalNAc, GlcAβ1,3GalNAc(4,6SO₄)β1,4GlcA, GalNAc(4,6SO₄)β1,4GlcAβ1,3GalNAc, GalNAc(4,6SO₄)β1,4GlcA(2SO₄)β1,3GalNAc(6SO₄), IdoAα1,3GalNAcβ1,4IdoA, GalNAcβ1,4IdoAα1,3GalNAc, IdoAα1,3GalNAc(4SO₄)β1,4IdoA, GalNAc(4SO₄)β1,4IdoAα1,3GalNAc, GlcAβ1,4GlcNAcα1,4GlcA, GlcNAcα1,4GlcAβ1,4GlcNAc, GlcA(2SO₄)β1,4GlcNAcα1,4GlcA, GlcNAcα1,4GlcA(2SO₄)β1,4GlcNAc, IdoA(2SO₄)α1,4GlcNAcα1,4GlcA, GlcNAcα1,4IdoA(2SO₄)β1,4GlcNAc, GlcA(2SO₄)β1,4GlcNSO₃α1,4GlcA, GlcNSO₃α1,4GlcA(2SO₄)β1,4GlcNAc, IdoA(2SO₄)α1,4GlcNSO₃Hα1,4GlcA, GlcNSO₃α1,4IdoA(2SO₄)α1,4GlcNAc, GlcAβ1,4GlcNα1,4GlcA, GlcAβ1,4GlcNSO₃α1,4GlcA, GlcNSO₃α1,4GlcAβ1,4GlcNAc, IdoAα1,4GlcNSO₃α1,4GlcA, GlcNSO₃α1,4IdoAα1,4GlcNAc, GlcAβ1,4GlcNSO₃(6SO₄)α1,4GlcA, GlcNSO₃(6SO₄)α1,4GlcAβ1,4GlcNAc, IdoAα1,4GlcNSO₃(6SO₄)α1,4GlcA, GlcNSO₃(6SO₄)α1,4IdoAα1,4GlcNAc, IdoA(2SO₄)α1,4GlcNSO₃(6SO₄)α1,4GlcA, GlcNSO₃(6SO₄)α1,4GlcA, GlcNSO₃(6SO₄)α1,4GlcA, GlcNSO₃(6SO₄)α1,4IdoA, IdoA(2SO₄)α1,4GlcNAc, IdoAα1,4GlcNSO₃α1,4IdoA, GlcAβ1,3GlcNAcβ1,4GlcA, GlcNAcβ1,4GlcAβ1,3GlcNAc, IdoAα1,4GlcNSO₃, IdoAα1,4GlcNSO₃(6SO₄), IdoA (2SO$_4$)α1,4GlcNSO$_3$, IdoA(2SO$_4$)α1,4GlcNSO$_3$(6SO$_4$), IdoA(2SO$_4$)α1,4GlcNSO$_3$(3SO$_4$), GlcAβ1,4GlcNSO$_3$, GlcAβ1,4GlcNSO$_3$(6SO$_4$), GlcA(2SO$_4$)β1,4GlcNAc, GlcA (2SO$_4$)β1,3Gal(6SO$_4$)β1,4GlcNAc, GlcAβ1,4GlcNSO$_3$(3,6SO$_4$), and GlcAβ1,4GlcNSO$_3$(3SO$_4$).

13. An immunity inducing method antigen-specific to a target oligosaccharide antigen R in a mammal, comprising: administering an immunity inducer comprising an artificial glycolipid or a salt thereof as an effective component to the mammal, wherein the artificial glycolipid has the chemical formula (2) and includes the target oligosaccharide antigen R:

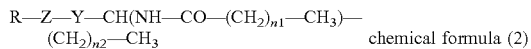

chemical formula (2)

wherein, in the chemical formula (2), R represents a linear chain or branched oligosaccharide constituted with 2 to 30 of one type or plural types of monosaccharides, Z represents a single bond, O, S or NH, a linker bound to thiomethyl, or an aminomethylated sugar alcohol, Y represents —(CH$_2$)$_m$—, n1 represents an integer from 2 to 40, n2 represents an integer from 1 to 27, and m represents an integer from 1 to 30, and wherein the target oligosaccharide antigen R is selected from the group consisting of an oligosaccharide antigen included in a mammal-derived glycoprotein N-linked sugar chain, an oligosaccharide antigen included in a mammal-derived glycoprotein O-linked sugar chain, and an oligosaccharide antigen included in a mammal-derived glycosaminoglycan type sugar chain.

14. The immunity inducing method according to claim 13, wherein the target oligosaccharide antigen R is an oligosaccharide antigen included in a mammal-derived glycoprotein N-linked sugar chain selected from the group consisting of Siaα2,6Galβ1,4GlcNAc, Siaα2,3Galβ1,4GlcNAc, Galβ1, 4GlcNAc, Galβ1,3GlcNAc, Siaα2,3Galβ1,4(Fucα1,3)GlcNAc, Galβ1,4 (Fucα1,3)GlcNAc, Siaα2,3Galβ1,3(Fucα1,4)GlcNAc, Siaα2,3Galβ1,3GlcNAc, Galβ1,3(Fucα1,4)GlcNAc, Siaα2,3Galβ1,3(Siaα2,6)GlcNAc, Siaα2,3Galβ1,3(Fucα1,4)(Siaα2,6)GlcNAc, Fucα1,2Galβ1,3(Fucα1,4)GlcNAc, Fucα1,2Galβ1,4GlcNAc, Fucα1,2Galβ1,4(Fucα1,3)GlcNAc, Fucα1,6GlcNAc, GlcNAcβ1,4 (Fucα1,6)GlcNAc, Manβ1,4GlcNAcβ1,4(Fucα1,6)GlcNAc, Manα1,6(Manα1,3)Manβ1,4GlcNAcβ1,4(Fucα1,6)GlcNAc, Manα1,6 (GlcNAcβ1,4) (Manα1,3)Manβ1, 4GlcNAcβ1,4GlcNAc, Manα1,6(GlcNAcβ1,4) (Manα1,3) Manβ1,4GlcNAcβ1,4(Fucα1,6)GlcNAc, GlcNAcβ1, 4GlcNAc, Manβ1,4GlcNAcβ1,4GlcNAc, GlcNAcβ1, 2Man, GlcNAcβ1,4Man, GlcNAcβ1,6Man, Galβ1, 3GlcNAcβ1,2Man, Galβ1,3GlcNAcβ1,4Man, Galβ1, 3GlcNAcβ1,6Man, Galβ1,4GlcNAcβ1,2Man, Galβ1, 4GlcNAcβ1,4Man, Galβ1,4GlcNAcβ1,6Man, Siaα2, 3Galβ1,4GlcNAcβ1,2Man, Siaα2,3Galβ1,4GlcNAcβ1, 4Man, Siaα2,3Galβ1,4GlcNAcβ1,6Man, Siaα2,3Galβ1, 3GlcNAcβ1,2Man, Siaα2,3Galβ1,3GlcNAcβ1,4Man, Siaα2,3Galβ1,3GlcNAcβ1,6Man, Siaα2,6Galβ1, 4GlcNAcβ1,2Man, Siaα2,6Galβ1,4GlcNAcβ1,4Man, Siaα2,6Galβ1,4GlcNAcβ1,6Man, GalNAcβ1,4GlcNAc, GalNAcβ1,4GlcNAcβ1,2Man, GalNAc(4SO$_4$)β1,4GlcNAc, GalNAc(4SO$_4$)β1,4GlcNAcβ1,2Man, GalNAc(4SO$_4$) β1,4GlcNAcβ1,4Man, GalNAc(4SO$_4$)β1,4GlcNAcβ1, 6Man, GlcAβ1,3Galβ1,4GlcNAc, GlcA(3SO$_4$)β1,3Galβ1, 4GlcNAc, Siaα2,3Galβ1,4 (Fucα1,3)GlcNAc(6SO$_4$), Siaα2,3Galβ1,4GlcNAc(6SO$_4$), Galβ1,4GlcNAc(6SO$_4$), Galβ1,4(Fucα1,3) GlcNAc(6SO$_4$), Siaα2,3Gal(6SO$_4$)β1,4 (Fucα1,3)GlcNAc, Siaα2,3Gal(6SO$_4$)β1,4GlcNAc, Gal (6SO$_4$)β1,4GlcNAc, Gal(6SO$_4$)β1,4GlcNAc(6SO$_4$), Galβ1, 4GlcNAcβ1,3Gal, GlcNAcβ1,3Galβ1,4GlcNAc, Galβ1, 4GlcNAc(6SO$_4$)β1,3Gal, GlcNAc(6SO$_4$)β1,3Galβ1, 4GlcNAc, Gal(6SO$_4$)β1,4GlcNAc(6SO$_4$)β1,3Gal, GlcNAc (6SO$_4$)β1,3Gal(6SO$_4$)β1,4GlcNAc, Siaα2,3Galβ1, 4GlcNAcβ1,3Galβ1,4(Fucα1,3)GlcNAc, Fucα1,2Galβ1, 3GlcNAc, Galα1,3(Fucα1,2)Galβ1,3GlcNAc, Galα1,3 (Fucα1,2)Galβ1,4GlcNAc, GalNAcα1,3(Fucα1,2)Galβ1, 3GlcNAc, GalNAcα1,3(Fucα1,2)Galβ1,4GlcNAc, Fucα1, 2Galβ1,4(Fucα1,3)GlcNAcβ1,3Gal, Gal(3SO$_4$)β1, 4GlcNAc, Gal(3SO$_4$)β1,4(Fucα1,3)GlcNAc, Gal(3SO$_4$)β1, 3GlcNAc, Gal(3SO$_4$)β1,3(Fucα1,4)GlcNAc, Gal(3SO$_4$)β1, 4GlcNAc(6SO$_4$), Gal(3SO$_4$)β1,4(Fucα1,3)GlcNAc(6SO$_4$), Siaα2,8Siaα2,8Sia, Siaα2,6GalNAcβ1,4GlcNAc, Siaα2, 3Galβ1,4(Fucα1,3)GlcNAcβ1,3Galβ1,4(Fucα1,3)GlcNAc, Galβ1,4GlcNAcβ1,3(Galβ1,4GlcNAcβ1,6)Gal, and Siaα2, 3Galβ1,4GlcNAcβ1,3(Siaα2,3Galβ1,4GlcNAcβ1,6)Gal.

15. The immunity inducing method according to claim 13, wherein the target oligosaccharide antigen R is an oligosaccharide antigen included in a mammal-derived glycoprotein O-linked sugar chain selected from the group consisting of Siaα2,3Galβ1,3GalNAc, Galβ1,3GalNAc, Siaα2,3Galβ1,3 (GlcNAcβ1,6)GalNAc, GalNAcα1,3GalNAc, GlcNAcβ (Siaα2,6)GalNAc, GalNAcα1,6GalNAc, GlcNAcβ1,6GalNAc, Fucα1,2GalNAc, Galβ1,3(GlcNAcβ1,6)GalNAc, Siaα2,6GalNAc, Siaα2,6(GlcNAcβ1,6)GalNAc, Siaα2, 3Galβ1,3(Siaα2,6)GalNAc, Galβ1,4GalNAc, Siaα2, 3Galβ1,4GalNAc, GlcNAcα1,4Gal, GlcNAcα1,4Galβ1, 4GlcNAc, GlcNAcα1,4Galβ1,4GalNAc, GlcNAcα1, 4Galβ1,4(GlcNAcα1,4Galβ1,4GlcNAcβ1,6)GalNAc, Siaα2,3Galβ1,4(Fucα1,3)GlcNAc(6SO$_4$)β1,6GalNAc, Gal(β3SO$_4$)β1,4GlcNAcβ1,6(Siaα2,3Galβ1,3)GalNAc, Siaα2,3Galβ1,4(Fucα1,3)GlcNAc(6SO$_4$)β1,3Galβ1,3GalNAc, Siaα2,3Galβ1,4(Fucα1,3)GlcNAc(6SO$_4$)β1,3Galβ1,3 (Siaα2,3Galβ1,4(Fucα1,3)GlcNAc(6SO$_4$)β1,6)GalNAc, Siaα2,3Gal(6SO$_4$) β1,4GlcNAcβ1,3Galβ1,3GalNAc, Gal (3SO$_4$)β1,3GalNAc(6SO$_4$), Siaα2,3Galβ1,3GalNAc (6SO$_4$), Gal(3SO$_4$)β1,3(Siaα2,6)GalNAc, and Gal(3SO$_4$) β1,3GalNAc.

16. The immunity inducing method according to claim 13, wherein the target oligosaccharide antigen R is an oligosaccharide antigen included in a mammal-derived glycosaminoglycan type sugar chain selected from the group consisting of Galβ1,4Xyl, Galβ1,3Galβ1,4Xyl, GlcAβ1, 3Galβ1,3Galβ1,4Xyl, GalNAcβ1,4IdoAα1,3Galβ1,3Galβ1, 4Xyl, GalNAcβ1,4GlcAβ1,3Galβ1,3Galβ1,4Xyl, GlcNAcα1,4GlcAβ1,3Galβ1,3Galβ1,4Xyl, GlcAβ1, 3GalNAcβ1,4GlcA, GalNAcβ1,4GlcAβ1,3GalNAc, GlcAβ1,3GalNAc(4SO$_4$)β1,4GlcA, GalNAc(4SO$_4$)β1,4 GlcAβ1,3GalNAc, GlcAβ1,3GalNAc(6SO$_4$)β1,4GlcA, GalNAc(6SO$_4$)β1,4GlcAβ1,3GalNAc, GlcA(2SO$_4$)β1,3 (6SO$_4$)GalNAcβ1,4GlcA, GalNAc(6SO$_4$)β1,4GlcA(2SO$_4$) β1,3GalNAc, GlcAβ1,3GalNAc(4,6SO$_4$)β1,4GlcA, GalNAc(4,6SO$_4$)β1,4GlcAβ1,3GalNAc, GalNAc(4,6SO$_4$)β1, 4GlcA(2SO$_4$)β1,3GalNAc(6SO$_4$), IdoAα1,3GalNAcβ1, 4IdoA, GalNAcβ1,4IdoAα1,3GalNAc, IdoAα1,3GalNAc (4SO$_4$)β1,4IdoA, GalNAc(4SO$_4$)β1,4IdoAα1,3GalNAc, GlcAβ1,4GlcNAcα1,4GlcA, GlcNAcα1,4GlcAβ1,4GlcNAc, GlcA(2SO$_4$)β1,4GlcNAcα1,4GlcA, GlcNAcα1, 4GlcA(2SO$_4$)β1,4GlcNAc, IdoA(2SO$_4$)α1,4GlcNAcα1, 4GlcA, GlcNAcα1,4IdoA(2SO$_4$)α1,4GlcNAc, GlcA(2SO$_4$) β1,4GlcNSO$_3$α1,4GlcA, GlcNSO$_3$α1,4GlcA(2SO$_4$)β1, 4GlcNAc, IdoA(2SO$_4$)α1,4GlcNSO$_3$Hα1,4GlcA, GlcNSO$_3$α1,4IdoA(2SO$_4$)α1,4GlcNAc, GlcAβ1,4GlcNα1, 4GlcA, GlcAβ1,4GlcNSO$_3$α1,4GlcA, GlcNSO$_3$α1, 4GlcAβ1,4GlcNAc, IdoAα1,4GlcNSO$_3$α1,4GlcA, GlcNSO$_3$α1,4IdoAα1,4GlcNAc, GlcAβ1,4GlcNSO$_3$ (6SO$_4$)α1,4GlcA, GlcNSO$_3$(6SO$_4$)α1,4GlcAβ1,4GlcNAc, IdoAα1,4GlcNSO$_3$(6SO$_4$)α1,4GlcA, GlcNSO$_3$(6SO$_4$α1,4IdoAα1,4GlcNAc, IdoA(2SO$_4$)α1,4GlcNSO$_3$(6SO$_4$)α1,4GlcA, GlcNSO$_3$(6SO$_4$)α1,4IdoA(2SO$_4$)α1,4GlcNAc, IdoAα1,4 GlcNSO$_3$α1,4IdoA, GlcAβ1,3GlcNAcβ1,4GlcA, GlcNAcβ1,4GlcAβ1,3GlcNAc, IdoAα1,4GlcNSO$_3$, IdoAα1,4GlcNSO$_3$(6SO$_4$), IdoA(2SO$_4$)α1,4GlcNSO$_3$, IdoA(2SO$_4$)α1,4GlcNSO$_3$(6SO$_4$), IdoA(2SO$_4$)α1,4GlcNSO$_3$(3SO$_4$), GlcAβ1,4GlcNSO$_3$, GlcAβ1,4GlcNSO$_3$(6SO$_4$), GlcA(2SO$_4$)β1,4GlcNAc, GlcA(2SO$_4$)β1,4GlcNSO$_3$(3SO$_4$), GlcAβ1,4GlcNSO$_3$(3,6SO$_4$), and GlcAβ1,4GlcNSO$_3$(3SO$_4$).

\* \* \* \* \*